(12) United States Patent
Jung et al.

(10) Patent No.: US 8,754,038 B2
(45) Date of Patent: Jun. 17, 2014

(54) TEMPLATE-FIXED PEPTIDOMIMETICS WITH CCR10 ANTAGONISTIC ACTIVITY

(75) Inventors: Françoise Jung, Huningue (FR); Frank Otto Gombert, Basel (CH); Daniel Obrecht, Bättwil (CH); Christian Bisang, Basel (CH); Sophie Barthélémy, Folgensbourg (FR); Alexander Lederer, Basel (CH); Eric Chevalier, Steinbrunn-le-Bas (FR)

(73) Assignee: Polyphor AG, Allschwil (CH)

( * ) Notice: Subject to any disclaimer, the term of this patent is extended or adjusted under 35 U.S.C. 154(b) by 0 days.

(21) Appl. No.: 13/510,864

(22) PCT Filed: Nov. 18, 2010

(86) PCT No.: PCT/EP2010/007016
§ 371 (c)(1),
(2), (4) Date: Jul. 27, 2012

(87) PCT Pub. No.: WO2011/060937
PCT Pub. Date: May 26, 2011

(65) Prior Publication Data
US 2012/0283168 A1    Nov. 8, 2012

(30) Foreign Application Priority Data
Nov. 20, 2009 (EP) .................. PCT/EP2009/065572

(51) Int. Cl.
*A61K 38/00* (2006.01)
*A61P 11/06* (2006.01)
*C07K 7/06* (2006.01)
*C07K 7/08* (2006.01)

(52) U.S. Cl.
CPC . *A61K 38/00* (2013.01); *C07K 7/06* (2013.01); *C07K 7/08* (2013.01)

USPC .......................................................... 514/1.7

(58) Field of Classification Search
CPC ............. A61K 38/00; C07K 7/06; C07K 7/08
See application file for complete search history.

(56) References Cited

FOREIGN PATENT DOCUMENTS

| | | |
|---|---|---|
| EP | 0 444 898 A1 | 9/1991 |
| WO | WO 2008/092281 A1 | 8/2008 |
| WO | WO 2008092281 A1 * | 8/2008 |

* cited by examiner

*Primary Examiner* — Marcela M Cordero Garcia
*Assistant Examiner* — Kaipeen Yang
(74) *Attorney, Agent, or Firm* — Birch, Stewart, Kolasch & Birch, LLP

(57) ABSTRACT

Novel template-fixed β-hairpin peptidomimetics of the general formula (I) wherein the single elements T or P are α-amino acid residues connected in either direction which, depending on their positions in the chain, are as defined in the description and the claims, and salts thereof, have the property to antagonize the receptor CCR10. They can be used as medicaments to treat or prevent diseases or conditions in the area of dermatological and cutaneous disorders, inflammation, allergic disorders, respiratory diseases, diseases of the gastro-intestinal tract, ophthalmic diseases, haematology and cancer. These β-hairpin peptidomimetics can be manufactured by a process which is based on a mixed solid- and solution phase synthetic strategy.

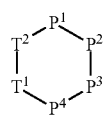

(I)

19 Claims, No Drawings

TEMPLATE-FIXED PEPTIDOMIMETICS WITH CCR10 ANTAGONISTIC ACTIVITY

The present invention provides peptidomimetics incorporating a chain of 4 α-amino acid residues as defined below attached to a template which provides specific structural constraints for a β-hairpin like conformation. These template-fixed β-hairpin mimetics have an antagonizing activity against the CCR10 receptor and are thus useful in the treatment of a variety of diseases and disorders such as inflammatory skin diseases, allergic asthma, gastro-intestinal/colon diseases, certain melanomas, cutaneous lymphoma, or other conditions mediated or sustained through the activity of CCR10. The present invention also relates to methods of using these compounds in the treatment of the various diseases and disorders stated above, to pharmaceutical compositions and forms comprising these compounds and efficient processes for the preparation and production of these compounds and their intermediates.

Many medically relevant biological processes are mediated by signal transduction that involves chemokines and their receptors, for instance the tissue specific recruitment of leukocytes to sites of inflammation. Within the blood there is a subset of memory T cells, morphologically characterized by the expression of the cutaneous lymphocyte antigen (CLA), which homes preferentially to dermal endothelial cells and associated tissue. There are recent studies showing that $CLA^+$ memory T cells as well express the chemokine receptor CCR10 and in addition that a specific ligand for this receptor, CCL27, is markedly up-regulated in tissue where an enrichment of these CCR10 expressing cells could be detected. This suggests, that the CCR10/CCL27 interaction plays a significant role in the tissue specific trafficking of $CLA^+$ memory T cells to e.g. inflammatory skin lesions. Besides on $CLA^+$ T cells, expression of CCR10 has been shown on melanocytes, dermal fibroblasts, skin keratinocytes, microvascular endothelial cells, Langerhans cells, and certain tissue types, e.g. human heart or colon. Abundant expression of CCL27, tightly regulated by proinflammatory mediators, such as TNF-α and IL-1β, was observed in the epidermis, predominantly by keratinocytes. While expressed in keratinocytes, CCL27 has a high affinity to extracellular matrix proteins, therefore, after extracellular diffusion, being as well presented on cutaneous vascular epithelium cells to participate in the leukocyte arrest.

An increasing number of studies are providing evidence that the CCR10/CCL27 interaction is instrumental for the migration and localization of T cell subsets during physiological responses in inflamed or infected skin or mucosal tissue (J. Morales et al., *Proc. Nat. Acad. Sci.*, 1999, 96, 14470-14475; B. Homey et al., *J. Immunol.*, 2000, 164, 3465-3470; B. Homey et al., *Nature Medicine*, 2002, 8, 157-165; B. Eksteen et al., *J. Immunol.*, 2006, 177, 593-603). Under pathological conditions such as psoriatic, atopic dermatitis or graft versus host disease the expression of CCL27 was found dramatically up-regulated in comparison to normal skin or tissue biopsy. Consequently a marked accumulation of recruited $CCR10^+$ lymphocytes could be observed (B. Homey, *Current Drug Targets—Inflammation &Allergy*, 2004, 3, 169-174; B. Homey et al., *J. Allergy Clin. Immunol.*, 2006, 118, 178-189; N. Annels et al., *Brit. J. of Haematology*, 2006, 133, 538-549). The same effect was noted in nickel-allergic humans after cutaneous challenge with nickel. In two separate in vivo proof of concept studies using a DNFB-induction and an ovalbumin DTH model in wild-type mice, respectively, the same authors could show a significant reduction in leukocyte recruitment along with lower swelling upon treatment with a function blocking antibody against CCL27.

More recent findings strongly suggest the significant contribution of a second ligand/receptor interaction of CCR10, in this case with the mucosa-associated epithelial chemokine CCL28, to the pathogeneses of inflammatory respiratory tract and skin diseases as demonstrated for allergic asthma in murine models and atopic dermatitis in human children (B. P. Mahon, *Immunology Letters*, 2006, 103, 92-100; M. H. M. Ezzat et al., *Int. J. of Dermatology*, 2009, 48, 822-829; A. Zlotnik et al., *J. of Biological. Chem.*, 2000, 275, 22313-22323).

Other studies in the field are indicating an increased expression of CCR10 in melanoma specimen up to 800-fold based on RNA quantification when compared with healthy skin. This resulted in mouse B16 melanoma cells not only in growth advantage, but also in a striking increase in metastasis to the draining lymph node in comparison to B16 cells without CCR10 expression. In vitro, activation of CCR10 by CCL27 leads to the activation of PI3K with the overall downstream effect of protection of CCR10-expressing B16 cells from tumor-specific cytotoxic T cells (T. Murakami et al., *J. Exp. Med.*, 2003, 198, 1337-1347; X. Wu et al., *Curr. Pharm. Design*, 2009, 15, 742-757; 0. Simonetti et al., *Eur. J. of Cancer*, 2006, 42, 1181-1187).

Proof of concept studies, such as those described above, highly recommend the trans-membrane G-protein coupled receptor (GPCR)CCR10 as an attractive target for the treatment of various disease conditions. Although over the past 15 years, nearly 350 therapeutic agents targeting GPCR receptors have been successfully introduced into the market (Th. Klabunde, G. Hessler, *ChemBioChem* 2002, 3, 928-44; G. Vauquelin et al. *Fundam. Clin. Pharmacol.* 2005, 19, 45-56), several toxicological problems, which arose from mainly lack of selectivity of some of those drugs, need to be further addressed. Clearly there is a need for a different concept in the design of these agents to solve the current issues and lead to effective and save drugs for treating or preventing the target associated diseases or disorders.

The present invention provides now new chemical entities for a potential use as potent, selective and drugable ligands for the GPC receptor CCR10. In the compounds described below, a new strategy is utilized to stabilize β-hairpin conformations in backbone-cyclic peptidomimetics exhibiting selective antagonizing activity against the CCR10 receptor. This involves transplanting a loop sequence of a natural or unnatural biopolymer onto a template, whose function is to restrain the peptide loop backbone into a hairpin geometry.

Template-bound hairpin mimetic peptides have been described in the literature (D, Obrecht, M. Altorfer, J. A. Robinson, *Adv. Med. Chem.* 1999, 4, 1-68; J. A. Robinson, *Syn. Lett.* 2000, 4, 429-441) and the ability to generate β-hairpin peptidomimetics using combinatorial and parallel synthesis methods has now been established (L. Jiang, K. Moehle, B. Dhanapal, D. Obrecht, J. A. Robinson, *Helv. Chim. Acta.* 2000, 83, 3097-3112). These methods allow the synthesis and screening of large hairpin mimetic libraries, which in turn considerably facilitates structure-activity studies and hence the discovery of new molecules with potent and, especially, selective agonizing or antagonizing activity.

There are few studies in the field describing tetrameric peptides linked to a template as agonist and/or antagonists of GPCR's and, among others, as well for CCR10 (WO2008092281). The present invention is now providing, as an alternative, novel compounds which differ significantly in structure and, surprisingly, exhibit a substantial improvement of key pharmaceutical parameters, e.g. biological potency, stability or selectivity.

β-Hairpin peptidomimetics obtained by the approach described here are useful as antagonist of CCR10 and therefore as agents in the chemotherapy of e.g. psoriasis, atopic dermatitis, contact sensitivity and allergic dermatitis, Stevens-Johnson syndrome, bullous cutaneous diseases, systemic lupus erythematosis, systemic and multiple sclerosis, allergic asthma, arthritis, graft versus host disease, certain melanoma and cutaneous lymphoma, thyroiditis, as well as inflammatory processes of the gastro-intestinal tract and the eye.

The present invention relates to novel β-hairpin peptidomimetics of formula (I),

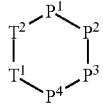

(I)

wherein the single elements T or P are connected in either direction from the carbonyl (C=O) point of attachment to the nitrogen (N) of the next element and wherein $T^1$ and $T^2$ are independently an L or D α-amino acid of one of the formulae

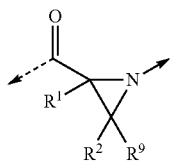

AA1

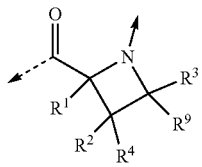

AA2

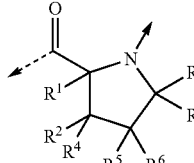

AA3

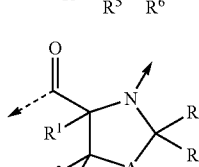

AA4

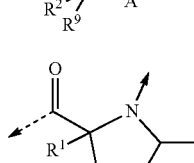

AA5

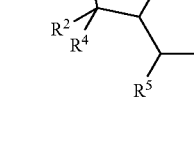

-continued

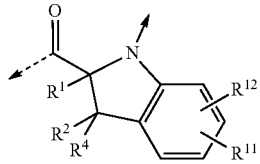

AA6

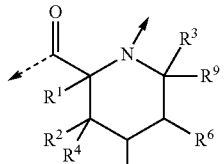

AA7

AA8

$P^1$ and $P^3$ are independently
  —$NR^1CH(R^{19})CO$—;
$P^2$ is —$NR^1C(R^{20})(R^{21})CO$—; or —$NR^1C(Z)CO$—;
$P^4$ is —$NR^1CH(R^{24})CO$—;
A is O; $NR^9$; S; SO; or $SO_2$
$R^1$, $R^2$ and $R^3$ are independently
  H; $CF_3$; lower alkyl; lower alkenyl; aryl-lower alkyl; or heteroaryl-lower alkyl;
$R^4$, $R^5$, $R^6$, $R^7$ and $R^8$ are independently
  H; F; $CF_3$; lower alkyl; lower alkenyl; cycloalkyl; heterocycloalkyl; aryl; heteroaryl; aryl-lower alkyl; heteroaryl-lower alkyl; —$(CHR^{13})_oOR^{15}$; —$(CHR^{13})_oSR^{15}$; —$(CHR^{13})_oNR^{15}R^{16}$; —$(CHR^{13})_oOCONR^{15}R^{16}$; —$(CHR^{13})_oNR^1CONR^{15}R^{16}$; —$(CHR^{13})_oNR^1COR^{15}$; —$(CHR^{13})_oCOOR^{15}$; —$(CHR^{13})_oCONR^{15}R^{16}$; —$(CHR^{13})_oPO(OR^1)_2$; —$(CHR^{13})_oSO_2R^{15}$; —$(CHR^{13})_oNR^1SO_2R^{15}$; —$(CHR^{13})_oSO_2NR^{15}R^{16}$; —$(CR^1R^{13})_oR^{30}$; or —$(CHR^1)_nO(CHR^2)_mR^{30}$; or
$R^4$ and $R^2$ taken together can form:
  =O; —$(CHR^{19})_p$—; —$(CH_2)_nO(CH_2)_m$; —$(CH_2)_nS(CH_2)_m$—; or —$(CH_2)_nNR^1(CH_2)_m$—; or
$R^4$ and $R^5$; $R^5$ and $R^6$; $R^6$ and $R^7$; $R^7$ and $R^8$; or $R^6$ and $R^9$ taken together can form: —$(CHR^{19})_p$—; —$(CH_2)_nO(CH_2)_m$; —$(CH_2)_nS(CH_2)_m$; or —$(CH_2)_nNR^1(CH_2)_m$—;
$R^9$ and Rw are independently
  H; F; $CF_3$; lower alkyl; lower alkenyl; cycloalkyl; heterocycloalkyl; aryl; heteroaryl; aryl-lower alkyl; heteroaryl-lower alkyl; —$(CHR^{13})_rOR^{15}$; —$(CHR^{13})_rSR^{15}$; —$(CHR^{10})_rNR^{15}R^{16}$; —$(CHR^{13})_rOCONR^{15}R^{16}$; —$(CHR^{13})_rNR^1CONR^{15}R^{16}$; —$(CHR^{13})_rNR^1COR^{15}$; —$(CHR^{13})_oCOOR^{15}$; —$(CHR^{13})_oCONR^{15}R^{16}$; —$(CHR^{13})_rPO(OR^1)_2$; —$(CHR^{13})_rSO_2R^{15}$; —$(CHR^{13})_rNR^1SO_2R^{15}$; —$(CHR^{13})_rSO_2NR^{15}R^{16}$; —$CR^1R^{13})_oR^{30}$; or —$(CHR^1)_rO(CHR^1)_oR^{30}$;
$R^{11}$ and $R^{12}$ are independently
  H; F; Cl; Br; $CF_3$; $OCF_3$; $OCHF_2$; CN; $NO_2$; lower alkyl; lower alkenyl; aryl; heteroaryl; aryl-lower alkyl; heteroaryl-lower alkyl; —$(CHR^{13})_oR^{15}$; —$(CHR^{13})_oSR^{15}$;

—(CHR$^{13}$)$_o$NR$^{15}$R$^{16}$; —(CHR$^{13}$)$_o$OCONR$^{15}$R$^{16}$;
—(CHR$^{13}$)$_o$NR$^1$CONR$^{15}$R$^{16}$; —(CHR$^{13}$)$_o$NR$^1$COR$^{15}$;
—(CHR$^{13}$)$_o$COOR$^{15}$; —(CHR$^{13}$)$_o$CONR$^{15}$R$^{16}$;
—(CHR$^{13}$)$_o$PO(OR$^1$)$_2$; —(CHR$^{13}$)$_o$SO$_2$R$^{15}$;
—(CHR$^{13}$)$_o$NR$^1$SO$_2$R$^{15}$; —(CHR$^{13}$)$_o$SO$_2$NR$^{15}$R$^{16}$; or
—(CR$^1$R$^{13}$)$_o$R$^{30}$;

R$^{13}$ is H; F; CF$_3$; lower alkyl; lower alkenyl; cycloalkyl; heterocycloalkyl; cycloalkyl-lower alkyl; heterocycloalkyl-lower alkyl; aryl; heteroaryl; aryl-lower alkyl; heteroaryl-lower alkyl; —(CHR$^1$)$_o$OR$^{15}$; —(CHR$^1$)$_o$SR$^{15}$; —(CHR$^1$)$_o$NR$^{15}$R$^{16}$; —(CHR$^1$)$_o$NC(=NR$^{17}$)NR$^{15}$R$^{16}$; —(CHR$^1$)$_o$COOR$^{15}$; —(CHR$^1$)$_o$CONR$^{15}$R$^{16}$; —(CHR$^1$)$_o$SO$_2$R$^{15}$; or —(CHR$^1$)$_o$SO$_2$NR$^{15}$R$^{16}$;

R$^{14}$ is H; CF$_3$; lower alkyl; lower alkenyl; cycloalkyl; heterocycloalkyl; cycloalkyl-lower alkyl; heterocycloalkyl-lower alkyl; aryl; heteroaryl; aryl-lower alkyl; heteroaryl-lower alkyl; cycloalkyl-aryl; heterocycloalkyl-aryl; cycloalkyl-heteroaryl; heterocycloalkyl-heteroaryl; aryl-cycloalkyl; aryl-heterocycloalkyl; heteroaryl-cycloalkyl; heteroaryl-heterocycloalkyl; —(CHR$^1$)$_o$OR$^{15}$; —(CHR$^1$)$_o$SR$^{15}$; —(CHR$^1$)$_o$NR$^{15}$R$^{16}$; —(CHR$^1$)$_o$COOR$^{15}$; —(CHR$^1$)$_o$CONR$^{15}$R$^{16}$; or —(CHR$^1$)$_o$SO$_2$R$^{15}$;

R$^{15}$, R$^{16}$, R$^{17}$ and 11$^{18}$ are independently

H; lower alkyl; lower alkenyl; lower alkoxy; cycloalkyl; heterocycloalkyl; cycloalkyl-lower alkyl; heterocycloalkyl-lower alkyl; aryl; heteroaryl; aryl-lower alkyl; heteroaryl-lower alkyl; cycloalkyl-aryl; heterocycloalkyl-aryl; cycloalkyl-heteroaryl; heterocycloalkyl-heteroaryl; aryl-cycloalkyl; aryl-heterocycloalkyl; heteroaryl-cycloalkyl; or heteroaryl-heterocycloalkyl; or the structural elements —NR$^{15}$R$^{16}$ and —NR$^{17}$R$^{18}$ can independently form:

heterocycloalkyl; aryl-heterocycloalkyl; or heteroaryl-heterocycloalkyl; or a group of one of the following formulae C1
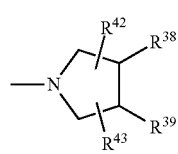

C2
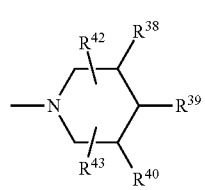

C3
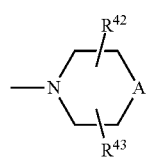

C4
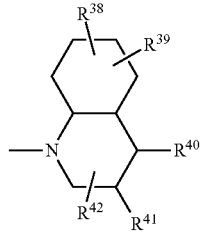

C5
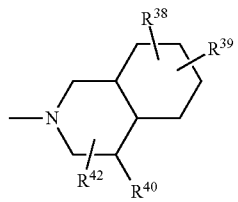

C6
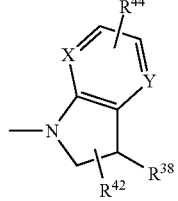

C7
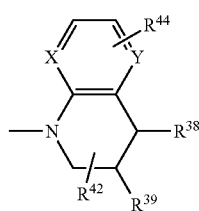

C8
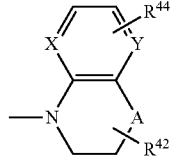

X and Y are independently
—CR$^{45}$; or N;

R$^{19}$ is alkyl; alkenyl; cycloalkyl-lower alkyl; heterocycloalkyl-lower alkyl;
—(CR$^1$R$^4$)$_n$R$^{30}$; —(CH$_2$)$_n$O(CH$_2$)$_m$R$^{30}$; —(CH$_2$)$_n$S(CH$_2$)$_m$R$^{30}$; or —(CH$_2$)$_n$NR$^{14}$(CH$_2$)$_m$R$^{30}$;

R$^{20}$ and R$^{21}$ are independently
alkyl; alkenyl; —(CHR$^4$)$_o$OR$^{15}$; —(CHR$^4$)$_o$SR$^{15}$; or —(CHR$^4$)$_r$NR$^{15}$R$^{16}$;

Z is —(CR$^{22}$R$^{23}$)$_{(n+m+1)}$—; —(CR$^{22}$R$^{23}$)$_n$NR$^{15}$(CR$^{22}$R$^{23}$)$_m$; —(CR$^{22}$R$^{23}$)$_n$O(CR$^{22}$R$^{23}$)$_m$—; —(CR$^{22}$R$^{23}$)$_n$S(CR$^{22}$R$^{23}$)$_m$—; —O(CR$^{22}$R$^{23}$)$_r$O—;

or a group of one of the formulae

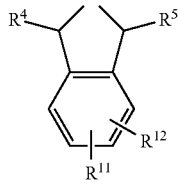
Z1

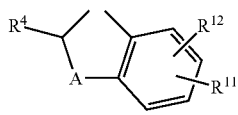
Z2

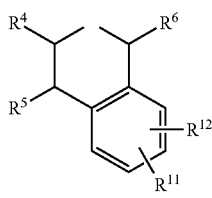
Z3

$R^{22}$ and $R^{23}$ are independently
H; F; $CF_3$; alkyl; alkenyl; cycloalkyl; heterocycloalkyl; aryl; heteroaryl; aryl-lower alkyl; or heteroaryl-lower alkyl; —$(CR^1R^{13})_oOR^{15}$; —$(CR^1R^{13})_oSR^{15}$; —$(CR^1R^{13})_oNR^{15}R^{16}$; —$(CR^1R^{13})_oCOOR^{15}$; —$CONR^{15}R^{16}$ or —$(CR^1R^{13})_oSO_2R^{15}$; or $R^{22}$ and $R^{23}$ taken together can form:
=O; =$NR^1$; =$NOR^1$; =$NOCF_3$; —$(CHR^1)_p$—; or —$O(CR^1R^2)_rO$—;

$R^{24}$ is alkyl; alkenyl; —$(CR^1R^{13})_qNR^{15}R^{16}$; —$(CR^1R^{13})_qNR^{25}R^{26}$; —$(CR^1R^{13})_qNR^{14}R^{27}$; —$(CH_2)_qC(=NR^{13})NR^{15}R^{16}$; —$(CH_2)_qC(=NOR^{17})NR^{15}R^{16}$; —$(CH_2)_qC(=NNR^{15}R^{16})NR^{17}R^{18}$; —$(CR^1R^{13})_qNR^2C(=NR^{17})NR^{15}R^{16}$; —$(CR^1R^{13})_qN=C(NR^{15}R^{16})NR^{17}R^{18}$; —$(CR^1R^{13})_qOR^{14}$; —$(CR^1R^{13})_qOR^{25}$; —$(CR^1R^{13})_qOR^{27}$; —$(CR^1R^{13})_qSR^{15}$; —$(CR^1R^{13})_qSO_2R^{15}$; —$(CR^1R^{13})_qNR^{14}SO_2R^{15}$; —$(CR^1R^{13})_qSO_2NR^1R^{14}$; —$(CR^1R^{13})_qNR^{14}SO_2NR^{15}R^{16}$; —$(CR^1R^{13})_qSO_2NR^{15}R^{16}$; —$(CR^1R^{13})_qPO(OR^1)_2$; —$(CH_2)_nO(CH_2)_mNR^{15}R^{16}$; —$(CH_2)_nO(CH_2)_mC(=NR^{17})NR^{15}R^{16}$; —$(CH_2)_nO(CH_2)_mC(=NOR^{17})NR^{15}R^{16}$; —$(CH_2)_nO(CH_2)_m(=NNR^{15}R^{16})NR^{17}R^{18}$; —$(CH_2)_nO(CH_2)_mNR^1C(=NR^{17})NR^{15}R^{16}$; —$(CH_2)_nO(CH_2)_mN=C(NR^{15}R^{16})NR^{17}R^{18}$; —$(CH_2)_nS(CH_2)_mNR^{15}R^{16}$; —$(CH_2)_nS(CH_2)_mC(=NR^{17})NR^{15}R^{16}$; —$(CH_2)_nS(CH_2)_mC(=NOR^{17})NR^{15}R^{16}$; —$(CH_2)_nS(CH_2)_mC(=NNR^{15}R^{16})NR^{17}R^{18}$; —$(CH_2)_nS(CH_2)_mNR^1C(=NR^{17})NR^{15}R^{16}$; —$(CH_2)_nS(CH_2)_mN=C(NR^{15}R^{16})NR^{17}R^{18}$; —$(CR^1R^{13})_qCOOR^{15}$; —$(CR^1R^{13})_qCOOR^{25}$; —$(CR^1R^{13})_qCOOR^{28}$; —$(CR^1R^{13})_qCONR^{15}R^{16}$; or —$(CR^1R^{13})_qCONR^{25}R^{26}$;
or alternatively heteroaryl; or heteroarylalkyl;

$R^{25}$ and $R^{26}$ are independently
H; —$CH_3$; —$[(CH_2)_2O]_rCH_3$; or —$[(CH_2)_2O]_rCF_3$;

$R^{27}$ is —$COR^{19}$; —$CO(CR^1R^{13})_oR^{15}$; —$CO(CR^1,R^{13})_oOR^{14}$; —$CO(CR^1R^{13})_oNR^{15}R^{16}$; —$CO(CR^1R^{13})_oNR^2R^{14}$; —$CO(CR^1R^{19})NR^{15}R^{16}$; —$CO(CR^1R^{29})NR^{15}R^{16}$; —$CO(CHR^1)_oCONR^{15}R^{16}$; —$CO(CHR^1)_oCONR^2SO_2R^{15}$; —$CO(CR^1R^{13})_oNR^2SO_2R^{15}$; —$CONR^1(CHR^{15})_nNR^2(CHR^{13})_mR^{14}$; —$CO(CHR^{15})_nO(CHR^{13})_mR^{14}$; —$CONR^1(CHR^{15})_nO(CHR^{13})_mR^{14}$; —$SO_2R^{19}$; —$SO_2(CR^1R^{13})_oR^{15}$; —$SO_2(CR^1R^{13})_oNR^{15}R^{16}$; or —$SO_2(CR^1R^{13})_oNR^1R^{25}$;

$R^{28}$ is —$NR^1C(R^2)(R^{19})COOR^{15}$; —$NR^1C(R^2)(R^{19})CONR^{15}R^{16}$; —$NR^1C(R^2)(R^{29})COOR^{15}$; —$NR^1C(R^2)(R^{29})CONR^{15}R^{16}$;

$R^{29}$ is —$(CR^1R^{13})_qNR^{15}R^{16}$; —$(CH_2)_qC(=NR^{17})NR^{15}R^{16}$; —$(CH_2)_qC(=NOR^{17})NR^{15}R^{16}$; —$(CH_2)_qC(=NNR^{15}R^{16})NR^{17}R^{18}$; —$(CR^1R^{13})_qNR^2C(=NR^{16})NR^{14}R^{15}$; —$(CR^1R^{13})_qN=C(NR^{15}R^{16})NR^{17}R^{18}$; —$(CR^1R^{13})_qSR^{15}$; —$(CR^1R^{13})_qSO_2R^{15}$; —$(CR^1R^{13})_qNR^{14}SO_2R^{15}$; —$(CR^1R^{13})_qSO_2NR^1R^{14}$; —$(CR^1R^{13})_qSO_2NR^{15}R^{16}$; —$(CR^1R^{13})_qNR^2SO_2NR^{15}R^{16}$; —$(CR^1R^{13})_qPO(OR^1)_2$; —$(CH_2)_nO(CH_2)_mNR^{15}R^{16}$; —$(CH_2)_nO(CH_2)_mC(=NR^{17})NR^{15}R^{16}$; —$(CH_2)_nO(CH_2)_mC(=NOR^{17})NR^{15}R^{16}$; —$(CH_2)_nO(CH_2)_mC(=NNR^{15}R^{16})NR^{17}R^{18}$; —$(CH_2)_nO(CH_2)_mNR^{14}C(=NR^{17})NR^{15}R^{16}$; —$(CH_2)_nO(CH_2)_mN=C(NR^{15}R^{16})NR^{17}R^{18}$; —$(CH_2)_nS(CH_2)_mNR^{15}R^{16}$; —$(CH_2)_nS(CH_2)_mNR^{15}R^{16}$; —$(CH_2)_nS(CH_2)_mC(=NR^{17})NR^{15}R^{16}$; —$(CH_2)_nS(CH_2)_mC(=NOR^{17})NR^{15}R^{16}$; —$(CH_2)_nS(CH_2)_mC(=NNR^{15}R^{16})NR^{17}R^{18}$; —$(CH_2)_nS(CH_2)_mNR^{14}C(=NR^{17})NR^{15}R^{16}$; —$(CH_2)_nS(CH_2)_mN=C(NR^{15}R^{16})NR^{17}R^{18}$; —$(CR^1R^{13})_qCOOR^{15}$; or —$(CR^1R^{13})_qCONR^{15}R^{16}$;

$R^{30}$ is an aryl group of one of the formulae

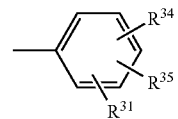
AR1

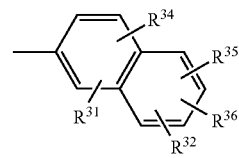
AR2

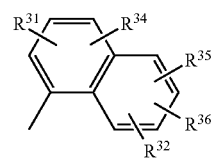
AR3 or a heteroaryl group of one of the formulae

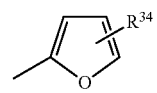
H1

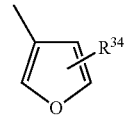
H2

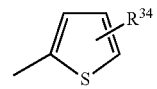
H3

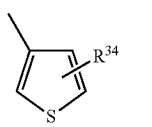 H4
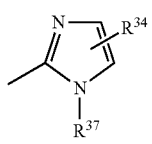 H5
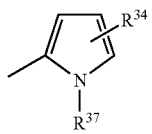 H6
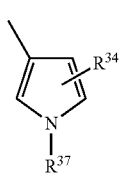 H7
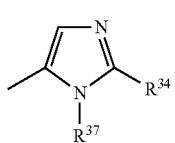 H8
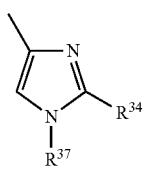 H9
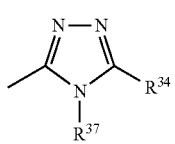 H10
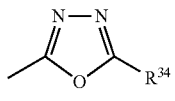 H11
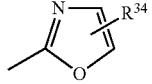 H12
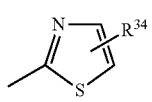 H13
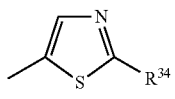 H14
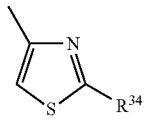 H15
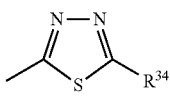 H16
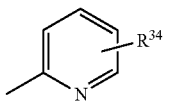 H17
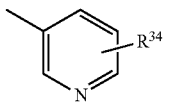 H18
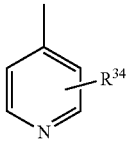 H19
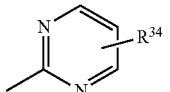 H20
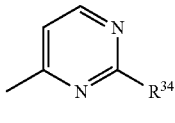 H21
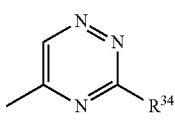 H22
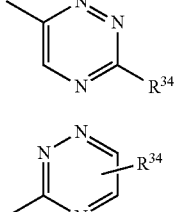 H23
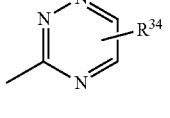 H24
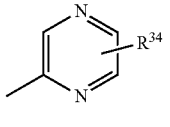 H25
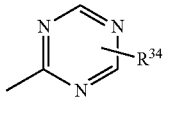 H26
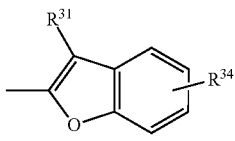 H27
H28

H29 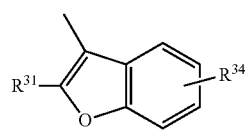
H30 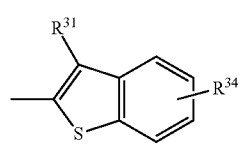
H31 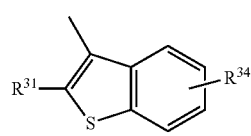
H32 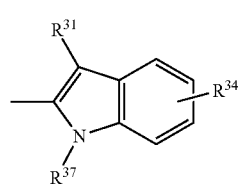
H33 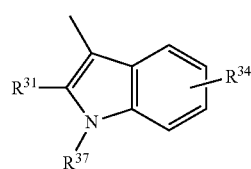
H34 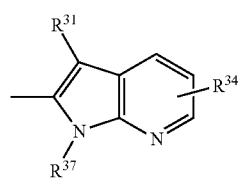
H35 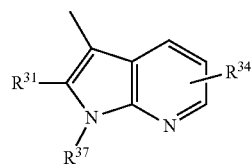
H36 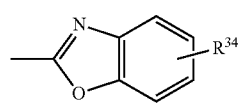
H37 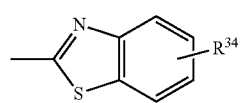
H38 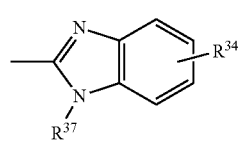
H39 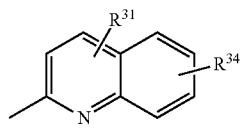
H40 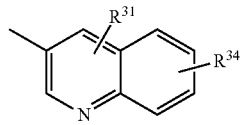
H41 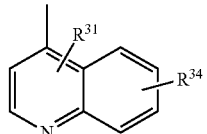
H42 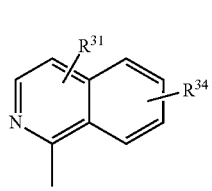
H43 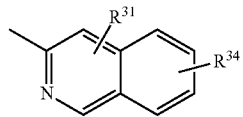
H44 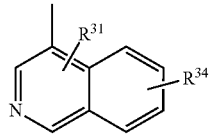
H45 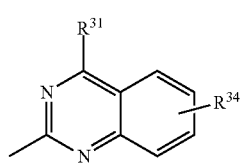
H46 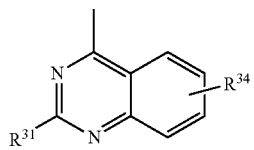
H47 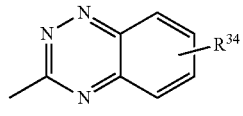
H48 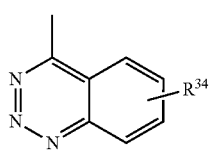

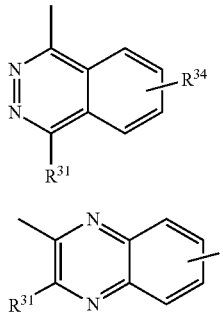

H49

H50

$R^{31}$ and $R^{32}$ are independently
  H; F; Cl; Br; $NO_2$; CN; $CF_3$; $OCHF_2$; $OCF_3$; lower alkyl; lower alkenyl; aryl-lower alkyl; aryl; heteroaryl; $-(CH_2)_oR^{33}$; $-(CH_2)_oOR^{15}$; $-O(CH_2)_oR^{33}$; $-(CH_2)_oSR^{15}$; $-(CH_2)_oNR^{15}R^{16}$; $-(CH_2)_o$ $OCONR^{15}R^{16}$; $-(CH_2)_oNR^1CONR^{15}R^{16}$; $-(CH_2)_o$ $NR^1COR^{15}$; $-(CH_2)_oCOOR^{15}$; $-(CH_2)_oCONR^{15}R^{16}$; $-(CH_2)_oPO(OR^1)_2$; $-(CH_2)_oSO_2R^{14}$; or $-(CH_2)_o$ $COR^{15}$;

$R^{33}$ is an aryl group of the formula

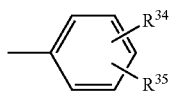

AR4

$R^{34}$, $R^{35}$ and $R^{36}$ are independently
  H; F; Cl; Br; OH; $NH_2$; $NO_2$; CN; $CF_3$; $OCHF_2$; $OCF_3$; $-NR^1R^{15}$; $-(CH_2)_oCOOR^{15}$; $-(CH_2)_oCONR^1R^{15}$; lower alkyl; lower alkoxy; or lower alkenyl;

$R^{37}$ is H; lower alkyl; or aryl-lower alkyl;

$R^{38}$, $R^{39}$, $R^{40}$ and $R^{41}$ are independently
  H; F; $CF_3$; lower alkyl; lower alkenyl; cycloalkyl; heterocycloalkyl; aryl; heteroaryl; aryl-lower alkyl; heteroaryl-lower alkyl; $-(CHR^1)_oOR^{15}$; $-(CHR^1)_oSR^{15}$; $-(CHR^1)_oNR^2R^{15}$; $-(CHR^1)_oOCONR^2R^{15}$; $-(CHR^1)_oNR^2CONR^3R^{15}$; $-(CHR^1)_oNR^2COR^{15}$; $-(CHR^1)_oCOOR^{15}$; $-(CHR^1)_oCONR^2R^{15}$; $-(CHR^1)_oPO(OR^2)_2$; $-(CHR^1)_oSO_2R^{15}$; $-(CHR^1)_o$ $NR^2SO_2R^{15}$; $-(CHR^1)_oSO_2NR^2R^{15}$; $-(CR^1R^2)_oR^{33}$; or $-(CHR^1)_nO(CHR^2)_mR^{33}$;

$R^{42}$ and $R^{43}$ are independently
  H; F; $CF_3$; lower alkyl; lower alkenyl; cycloalkyl; heterocycloalkyl; aryl; heteroaryl; aryl-lower alkyl; heteroaryl-lower alkyl; $-(CHR^1)_rOR^{15}$; $-(CHR^1)_rSR^{15}$; $-(CHR^1)_rNR^2R^{15}$; $-(CHR^1)_rOCONR^2R^{15}$; $-(CHR^1)_rNR^2CONR^3R^{15}$; $-(CHR^1)_rNR^2COR^{15}$; $-(CHR^1)_oCOOR^{15}$; $-(CHR^1)_oCONR^2R^{15}$; $-(CHR^1)_r$ $PO(OR^2)_2$; $-(CHR^1)_rSO_2R^{15}$; $-(CHR^1)_rNR^2SO_2R^{15}$; $-(CHR^1)_rSO_2NR^2R^{15}$; $-(CR^1R^2)_oR^{33}$; or $-(CHR^1)_rO(CHR^2)_oR^{33}$;

$R^{44}$ and $R^{45}$ are independently
  H; F; Cl; Br; $CF_3$; $OCF_3$; $OCHF_2$; CN; $NO_2$; lower alkyl; lower alkenyl; aryl; heteroaryl; aryl-lower alkyl; heteroaryl-lower alkyl; $-(CHR^1)_oOR^{15}$; $-(CHR^1)_oSR^{15}$; $-(CHR^1)_oNR^2R^{15}$; $-(CHR^1)_oOCONR^2R^{15}$; $-(CHR^1)_oNR^2CONR^3R^{15}$; $-(CHR^1)_oNR^2COR^{15}$; $-(CHR^1)_oCOOR^{15}$; $-(CHR^1)_oCONCR^2R^{15}$; $-(CHR^1)_oPO(OR^2)_2$; $-(CHR^1)_oSO_2R^{15}$; $-(CHR^1)_o$ $NR^2SO_2R^{15}$; $-(CHR^1)_oSO_2NR^2R^{15}$; or $-(CR^1R^2)_o$ $R^{33}$;

n and m are independently an integer of 0-5 with the proviso that n+m≤6;
o is 0-4; p is 2-6; q is 1-6; r is 1-3;
or pharmaceutically acceptable salts thereof.

Each single group "$R^x$", with the same index-number x for x=1-45 in a specific formula, is independently selected and, therefore, they are the same or different.

As used in this description, the term "alkyl", taken alone or in combinations (i.e. as part of another group, such as "arylalkyl") designates saturated, straight-chain or branched hydrocarbon radicals having up to 12, preferably up to 8, carbon atoms and may be optionally substituted. In accordance with a preferred embodiment of the present invention "alkyl" is "lower alkyl" which designated alkyl groups having up to 6 carbon atoms.

The term "alkenyl", taken alone or in combinations, designates straight chain or branched hydrocarbon radicals having up to 12, preferably up to 8, carbon atoms and containing at least one or, depending on the chain length, up to four olefinic double bonds. Such alkenyl moieties are optionally substituted and can exist as E or Z configurations, both of which are part of the invention.

The term "cycloalkyl", taken alone or in combinations, refers to a saturated or partially unsaturated alicyclic moiety having from three to ten carbon atoms and may be optionally substituted. Examples of this moiety include, but are not limited to, cyclohexyl, norbonyl, decalinyl and the like.

The term "heterocycloalkyl", taken alone or in combinations, describes a saturated or partially unsaturated mono- or bicyclic moiety having from three to nine ring carbon atoms and one or more ring heteroatoms selected from nitrogen, oxygen or sulphur. This term includes, for example, morpholino, piperazino, azetidinyl, pyrrolidinyl, tetrahydrofuranyl, piperidinyl, octahydro-1H-indolyl, 1,7-diazaspiro[4.4]nonane and the like. Said heterocycloalkyl ring(s) might be optionally substituted.

The term "aryl", taken alone or in combinations, designates aromatic carbocyclic hydrocarbon radicals containing one or two six-membered rings, such as phenyl or naphthyl, which may be optionally substituted by up to three substituents such as Br, Cl, F, $CF_3$, $OCF_3$, $OCHF_2$, $N(CH_3)_2$, $NO_2$, lower alkyl, lower alkenyl, phenyl or phenoxy.

The term "heteroaryl", taken alone or in combinations, designates aromatic heterocyclic radicals containing one or two five- and/or six-membered rings, at least one of them containing up to three heteroatoms selected from the group consisting of O, S and N and whereby the heteroaryl radicals or tautomeric forms thereof may be attached via any suitable atom. Said heteroaryl ring(s) are optionally substituted, e.g. as indicated above for "aryl".

The term "arylalkyl", as used herein, refers to an alkyl group as defined above, substituted by an aryl group, as defined above. Examples of arylalkyl moieties include, but are not limited to, benzyl, 1-phenylethyl, 2-phenylethyl, 3-phenylpropyl, 2-phenyl-propyl and the like. Similarly, the term "aryl-lower alkyl", refers to the above moiety but wherein the alkyl group is a "lower alkyl" group.

The term "heteroarylalkyl", as used herein, refers to an alkyl group as defined above, substituted by a heteroaryl group, as defined above. Analogously the term "heteroaryl-lower alkyl", refers to the above moiety but wherein the alkyl group is a "lower alkyl" group.

The term "aryl-cycloalkyl", as used herein, refers to a cycloalkyl group as defined above, substituted or annelated by an aryl group, as defined above. Examples of aryl-cycloalkyl moieties include, but are not limited to, phenylcyclopentyl, 2,3-dihydro-1H-indenyl, 1,2,3,4-tetrahydronaphthalenyl and the like.

The term "aryl-heterocycloalkyl", as used herein, refers to a heterocycloalkyl group as defined above, substituted or annelated by an aryl group, as defined above. Examples of aryl-heterocycloalkyl moieties include, but are not limited to, indolinyl, 1,2,3,4-tetrahydroquinolinyl and the like.

The term "heteroaryl-cycloalkyl", as used herein, refers to a cycloalkyl group as defined above, substituted or annelated by a heteroaryl group, as defined above. Examples of heteroaryl-cycloalkyl moieties include, but are not limited to, 5,6,7,8-tetrahydro-quinolinyl and the like.

The term "heteroaryl-heterocycloalkyl", as used herein, refers to a heterocycloalkyl group as defined above, substituted or annelated by a heteroaryl group, as defined above. Examples of heteroaryl-heterocycloalkyl moieties include, but are not limited to, 4-(thiazol-2-yl)piperazinyl, 5,6,7,8-tetrahydro-1,6-naphthyridinyl and the like.

The terms "cycloalkyl-aryl", "heterocycloalkyl-aryl", "cycloalkyl-heteroaryl", and "heterocycloalkyl-heteroaryl", as used herein, are defined analog to the terms "aryl-cycloalkyl", "aryl-heterocycloalkyl", "heteroaryl-cycloalkyl" and "heteroaryl-heterocycloalkyl", as defined above, but connected in the opposite direction, e.g. instead of 4-(thiazol-2-yl)piperazinyl the term refers to 2-(piperazin-1-yl)thiazolyl and the like.

The terms "alkoxy" and "aryloxy", taken alone or in combinations, refer to the groups of —O-Alkyl and —O-Aryl respectively, wherein an alkyl group or an aryl group is as defined above.

The term "optionally substituted" is intended to mean that a group, such as but not limited to alkyl, alkenyl, cycloalkyl, aryl, heteroaryl, heterocycloalkyl, alkoxy and aryloxy may be substituted with one or more substituents independently selected from but not limited to, e.g., amino (—NH$_2$), dimethylamino, nitro (—NO$_2$), halogen (F, Cl, Br, I), CF$_3$, cyano (—CN), hydroxy, methoxy, oxo (=O), carboxy, phenyl, phenyloxy, benzyl, sulfonic acid, sulfate, phosphonic acid, phosphate, or phosphonate etc.

The term "lower" designates radicals and compounds having up to 6 atoms. Thus, for example, the term "lower alkyl" designates saturated, straight-chain, or branched hydrocarbon radicals having up to 6 carbon atoms, such as methyl, ethyl, n-propyl, isopropyl, n-butyl, s-butyl, isobutyl, t-butyl, and the like and may be optionally substituted.

The peptidomimetics of the present invention can also be diastereomers (e.g. epimers) or enantiomers of the compounds of formula (I). These stereoisomers can be prepared by a modification of the process described below in which epimers or enantiomers of chiral starting materials are used. In case of ambiguous stereochemistry in the above description each single epimer is part of the present invention as well as a mixture of both.

A further embodiment of the present invention may also include compounds, which are identical to the compounds of formula (I), except that one or more atoms are replaced by an atom having an atomic mass number or mass different from the atomic mass number or mass usually found in nature, e.g. compounds enriched in $^2$H(D), $^3$H, $^{11}$C, $^{14}$C, $^{127}$I etc. These isotopic analogs and their pharmaceutical salts and formulations are considered useful agents in the therapy and/or diagnostic, for example, but not limited to, where a fine-tuning of in vivo half-life time could lead to an optimized dosage regimen.

A particular embodiment of the invention relates to derivatives of general formula (I), wherein specifically $T^1$ is $^D$Pro; $^D$Pip; or $^D$Aze;

$T^2$ is an L or D α-amino acid of one of the formulae

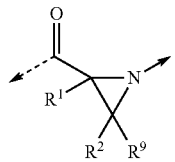

AA1

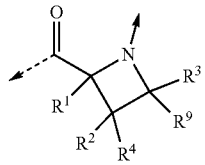

AA2

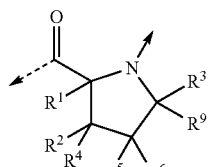

AA3

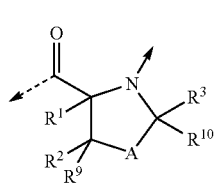

AA4

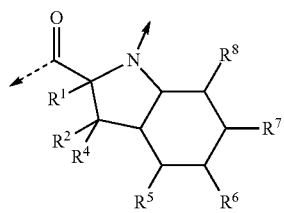

AA5

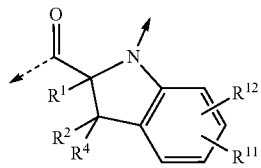

AA6

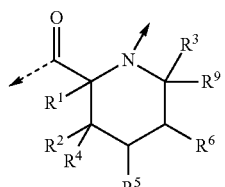

AA7

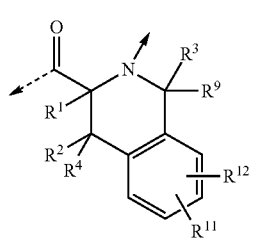

AA8

$R^{14}$ is H; $CF_3$; lower alkyl; lower alkenyl; cycloalkyl; heterocycloalkyl; cycloalkyl-lower alkyl; heterocycloalkyl-lower alkyl; aryl; heteroaryl; aryl-lower alkyl; heteroaryl-lower alkyl; —$(CHR^1)_sOR^{15}$; —$(CHR^1)_sSR^{15}$; —$(CHR^1)_sNR^{15}R^{16}$; —$(CHR^1)_oCOOR^{15}$; —$(CHR^1)_o CONR^{15}R^{16}$; or —$(CHR^1)_oSO_2R^{15}$;

$R^{15}$, $R^{16}$, $R^{17}$ and $R^{18}$ are independently

H; lower alkyl; lower alkenyl; lower alkoxy; cycloalkyl; heterocycloalkyl; cycloalkyl-lower alkyl; heterocycloalkyl-lower alkyl; aryl; heteroaryl; aryl-lower alkyl; or heteroaryl-lower alkyl; or the structural elements —$NR^{15}R^{16}$ and —$NR^{17}R^{18}$ can independently form a group of one of the formulae

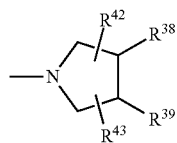

C1

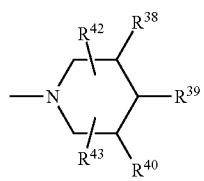

C2

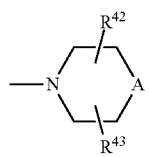

C3

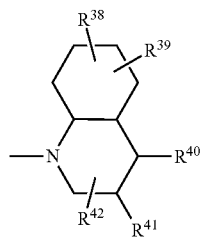

C4

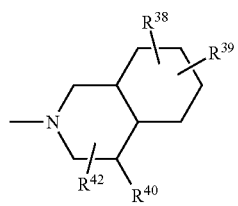

C5

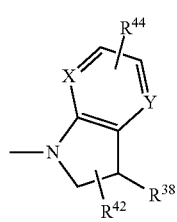

C6

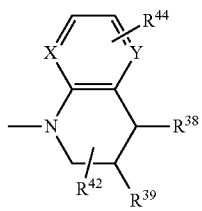

C7

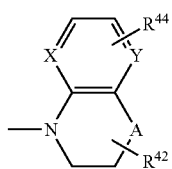

C8

$R^{24}$ is alkyl; alkenyl; —$(CR^1R^{13})_qNR^{15}R^{16}$; —$(CR^1R^{13})_q NR^{25}R^{26}$; —$(CR^1R^{13})_qNR^{14}R^{27}$; —$(CH_2)_qC(=NR^{17}) NR^{16}R^{16}$; —$(CR^1R^{13})_qNR^2C(=NR^{17})NR^{15}R^{16}$; —$(CR^1R^{13})_qOR^{15}$; —$(CR^1R^{13})_qOR^{25}$; —$(CR^1R^{13})_q OR^{27}$; —$(CR^1R^{13})_qSR^{15}$; —$(CR^1R^{13})_qSO_2R^{15}$; —$(CR^1R^{13})_qNR^{15}SO_2R^{16}$; —$(CR^1R^{13})_qSO_2NR^1R^{14}$; —$(CR^1R^{13})_qSO_2NR^{15}R^{16}$; —$(CH_2)_nO(CH_2)_mNR^{15}R^{16}$; —$(CH_2)_nO(CH_2)_mC(=NR^{17})NR^{15}R^{16}$; —$(CH_2)_nO (CH_2)_mNR^1C(=NR^{17})NR^{15}R^{16}$; —$(CH_2)_nO(CH_2)_m N=C(NR^{15}R^{16})NR^{17}R^{18}$; —$(CH_2)_nS(CH_2)_mNR^{15}R^{16}$; —$(CR^1R^{13})_qCOOR^{15}$; —$(CR^1R^{13})_qCOOR^{25}$; —$(CR^1R^{13})_qCOOR^{28}$; —$(CR^1R^{13})_qCONR^{15}R^{16}$; or —$(CR^1R^{13})_qCONR^{25}R^{26}$;

or alternatively heteroaryl; or heteroarylalkyl;

s is 2-4 with all other elements of formula (I) being as described above.

In another particular embodiment of the invention the elements of general formula (I) are defined as follows $T^1$ is $^DPro$; $^DPip$; or $^DAze$;

$T^2$ is an L or D α-amino acid of one of the formulae

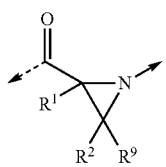

AA1

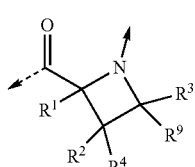

AA2

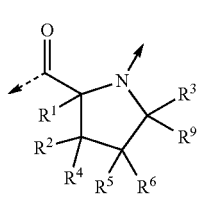

AA3

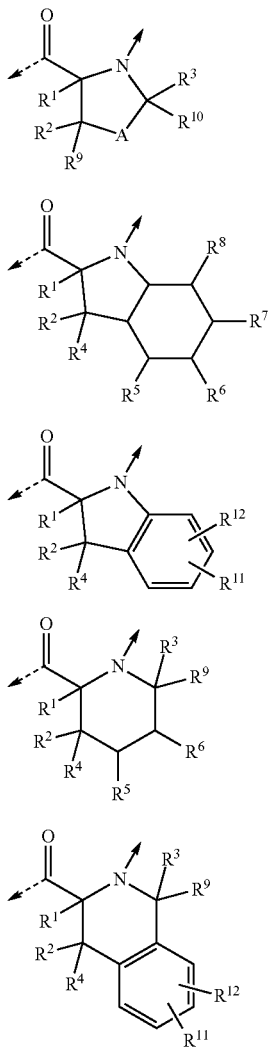

P¹ and P³ are independently
His; His(Me); His(Bn); hHis; Phe; Phe(2Cl); Phe(3Cl); Phe(4Cl); Phe(3,4Cl₂); Phe(2F); Phe(3F); Phe(4F); Phe(3,4F₂); Phe(3CN); Phe(4CN); Phe(2CF₃); Phe(3CF₃); Phe(4CF₃); Phe(3,4(CF₃)₂); Phe(4COOMe); hPhe; Thi; Tza; Trp; Trp(5OH); Trp(5Cl); Trp(6Cl); Trp(5,6Cl₂); Trp(5Br); Trp(6Br); Trp(6CF₃); Trp(7Aza); hTrp; Tyr; Tyr(Me); Tyr(Ph); Tyr(Bn); Tyr(4OHPh); Tyr(4MeO-COBn); hTyr; Thr(Bn); Ser(Bn); 2 Pal; 3 Pal; 4 Pal; Phg; Ala(2Furyl); Ala(3Furyl); Ala(2Quin); Ala(3Quin); Ala(4Quin); Ala(tBu); Gly(tBu); 1Nal; 2Nal; Nle(6OBn); Cha; hCha; Bip; Bbta; or OctG;

P² is Aib; Ac3c; Ac4c; Cyp; Chx; Chx(4-oxo); Ac7c; Ac8c; ᴰAtc; ᴸAtc; ᴰᴸAtc; Deg; or 4,4-AC-ThioTHP;

P⁴ is Arg; hArg; Ala(Ppz); Thr; alloThr; Gln; Gln(Me); Gln(Me₂); Gln(iPr); Gln(cPr); Gln(iBu); Glu(Ala); Glu(ᴰAla); Glu(Arg); Glu(ᴰArg); Glu(Glu); Glu(Gly); Glu(His); Glu(Leu); Glu(ᴰLeu); Glu(2Nal); Glu(Sar); Glu(Trp); Glu(ᴰTrp); Cys; hCys; Ser; hSer; Ser(Me); hSer(Me); Thr; Met; Met(O₂); Lys; hLys; Lys(Ac); Lys(Me); Lys(Bz); Lys(Nic); Lys(4Oxa); Lys((5R)OH); Orn; Dap; Dap(MeO(CH₂)₂); Dap(CONH₂); Dap((MeO(CH₂)₂)₂); Dab(Sar); Dab; Dab(Ac); Dab(Ala); Dab(ᴰAla); Dab(Arg); Dab(ᴰArg); Dab(Dab); Dab(Glu); Dab(Gly); Dab(His); Dab(Leu); Dab(ᴰLeu); Dab(MEMCO); Dab(4Me₂NPhSO₂); Dab(MeO(CH₂)₂NHCO); Dab((MeO(CH₂)₂)(Me)NCO); Dab(MePpzCO); Dab(MeSO₂); Dab(morphCO); Dab(2Nal); Dab(Trp); Dab(ᴰTrp); Dab(Sar); Gln(Alk1); Gln(Alk2); Gln(Alk3); Gln(Alk4); Gln(Alk5); Gln(Alk6); Gln(Alk7); Gln(Alk8); Gln(Alk9); Gln(Alk10); Gln(Alk11); Gln(Alk12); Gln(Alk13); Gln(Alk14); Gln(Alk15); Gln(Alk16); Gln(Alk17); Gln(Alk18); Gln(Alk19); Gln(Alk20); Gln(Alk21); Gln(Alk22); Gln(Alk23); Gln(Alk24); Gln(Alk25); Gln(Alk26); Gln(Alk27); Gln(Alk28); Gln(Alk29); Gln(Alk30); Gln(Alk31); Gln(Alk32); Gln(Alk33); Gln(Alk34); Glu(cN1); Glu(cN2); Glu(cN3); Glu(cN4); Glu(cN5); Glu(cN6); Glu(cN7); Glu(cN8); Glu(cN9); Glu(cN10); Glu(cN11); Glu(cN12); Glu(cN13); Glu(cN14); Glu(cN15); Glu(cN16); Glu(cN17); Sab(N1); Sab(N2); Sab(N3); Sab(N4); Sab(N5); Sab(N6); Sab(N7); Sab(N8); Sab(N9); Sab(N10); Sab(N11); Sab(N12); Sab(N13); Sab(N14); Sab(N15); Sab(N16); Sab(N17); Sab(N18); Sab(N19); Sab(N20); Sab(N21); Sab(N22); Sab(N23); Sab(N24); Sab(N25); Sab(N26); Sab(N27); Sab(N28); Sab(N29); Sab(N30); Sab(N31); Sab(N32); Sab(N33); Sab(N34); Sab(N35); Sab(N36); Sab(N37); Sab(N38); Sab(N39); Sab(N40); Sab(N41); Sab(N42); Sab(N43); Sab(N44); Sab(N45); Sab(N46); Sab(N47); Sab(N48); Sab(N49); Sab(N50); Sab(N51); Sab(N52); Sab(N53); Sab(N54); Sab(N55); Sab(N56); Sab(N57); Sab(N58); Sab(N59); Sab(N60); Sab(N61); Dab(SN1); Dab(SN2); Dab(SN3); Dab(SN4); Dab(SN5); Dab(SN6); Dab(SN7); Dab(SN8); Dab(SN9); Dab(SN10); Dab(SN11); Dab(SN12); Dab(SN13); Dab(SN14); Dab(SN15); Dab(SN16); Dab(SN17); Dab(SN18); Dab(SN19); Dab(SN20); Dab(SN21); Dab(SN22); Dab(SN23); Dab(SN24); Dab(SN25); Dab(SN26); Dab(SN27); Dab(SN28); Dab(SN29); Dab(SN30); Dab(SN31); Dab(SN32); Dab(SN33); Dab(SN34); Dab(SN35); Dab(SN36); Dab(SN37); Dab(SN38); Dab(SN39); Dab(SN40); Dab(SN41); Dab(SN42); Dab(SN43); Dab(SN44); Dab(SN45); Dab(SN46); Dab(SN47); Dab(SN48); Dab(SN49); Dab(SN50); Dab(SN51); Dab(SN52); Dab(SN53); Dab(SN54); Dab(SN55); Dab(SN56); Dab(SN57); Dab(SN58); Dab(SN59); Dab(SN60); Dab(SN61); Dab(UN1); Dab(UN2); Dab(UN3); Dab(UN4); Dab(UN5); Dab(UN6); Dab(UN7); Dab(UN8); Dab(UN9); Dab(UN10); Dab(UN11); Dab(UN12); Dab(UN13); Dab(UN14); Dab(UN15); Dab(UN16); Dab(UN17); Dab(UN18); Dab(UN19); Dab(UN20); Dab(UN21); Dab(UN22); Dab(UN23); Dab(UN24); Dab(UN25); Dab(UN26); Dab(UN27); Dab(UN28); Dab(UN29); Dab(UN30); Dab(UN31); Dab(UN32); Dab(UN33); Dab(UN34); Dab(UN35); Dab(UN36); Dab(UN37); Dab(UN38); Dab(UN39); Dab(UN40); Dab(UN41); Dab(UN42); Dab(UN43); Dab(UN44); Dab(UN45); Dab(UN46); Dab(UN47); Dab(UN48); Dab(UN49); Dab(UN50); Dab(UN51); Dab(UN52); Dab(UN53); Dab(UN54); Dab(UN55); Dab(UN56); Dab(UN57); Dab(UN58); Dab(UN59); Dab(UN60); Dab(UN61); Dab(S1); Dab(S2); Dab(S3); Dab(S4); Dab(S5); Dab(S6); Dab(S7); Dab(S8); Dab(S9); Dab(S10); Dab(S11); Dab(S12); Dab(S13); Dab(S14); Dab(S15); Dab(S16); Dab(S17); Dab(S18); Dab(A1); Dab(A2); Dab(A3); Dab(A4); Dab(A5); Dab(A6); Dab(A7); Dab(A8); Dab(A9); Dab(A10); Dab(A11); Dab(A12); Dab(A13); Dab(A14); Dab(A15); Dab(A16); Dab(A17); Dab(A18); Dab(A19); Dab(A20); Dab(A21); Dab(A22); Dab(A23); Dab(A24); Dab(A25); Dab(A26); Dab(A27); Dab(A28); Dab(A29); Dab(A30); Dab(A31); Dab(A32); Dab(A33); Dab(A34); Dab(A35); Dab(A36); Dab(A37);

Dab(A38); Dab(A39); Dab(A40); Dab(A41); Dab(A42); Dab(A43); Dab(A44); Dab(A45); Dab(A46); Dab(A47); Dab(A48); Dab(A49); Dab(A50); Dab(A51); Dab(A52); Dab(A53); Dab(A54); Dab(A55); Dab(A56); Dab(Suc1); Dab(Suc2); Dab(Suc3); Dab(Suc4); Dab(SucS); Dab (Suc6); Dab(Suc7); Dab(Suc8); Dab(Suc9); Dab(Suc10); Asn(Alk1); Asn(Alk2); Asn(Alk3); Asn(Alk4); Asn(Alk5); Asn(Alk6); Asn(Alk7); Asn(Alk8); Asn(Alk9); Asn(Alk10); Asn(Alk11); Asn(Alk12); Asn(Alk13); Asn(Alk14); Asn(Alk15); Asn(Alk16); Asn(Alk17); Asn(Alk18); Asn(Alk19); Asn(Alk20); Asn(Alk21); Asn(Alk22); Asn(Alk23); Asn(Alk24); Asn(Alk25); Asn(Alk26); Asn(Alk27); Asn(Alk28); Asn(Alk29); Asn(Alk30); Asn(Alk31); Asn(Alk32); Asn(Alk33); Asn(Alk34); Asp(cN1); Asp(cN2); Asp(cN3); Asp(cN4); Asp(cN5); Asp(cN6); Asp(cN7); Asp(cN8); Asp(cN9); Asp(cN10); Asp(cN11); Asp(cN12); Asp(cN13); Asp(cN14); Asp(cN15); Asp(cN16); Asp(cN17); Sap(N1); Sap(N2); Sap(N3); Sap(N4); Sap(N5); Sap(N6); Sap(N7); Sap(N8); Sap(N9); Sap(N10); Sap(N11); Sap(N12); Sap(N13); Sap(N14); Sap(N15); Sap(N16); Sap(N17); Sap(N18); Sap(N19); Sap(N20); Sap(N21); Sap(N22); Sap(N23); Sap(N24); Sap(N25); Sap(N26); Sap(N27); Sap(N28); Sap(N29); Sap(N30); Sap(N31); Sap(N32); Sap(N33); Sap(N34); Sap(N35); Sap(N36); Sap(N37); Sap(N38); Sap(N39); Sap(N40); Sap(N41); Sap(N42); Sap(N43); Sap(N44); Sap(N45); Sap(N46); Sap(N47); Sap(N48); Sap(N49); Sap(N50); Sap(N51); Sap(N52); Sap(N53); Sap(N54); Sap(N55); Sap(N56); Sap(N57); Sap(N58); Sap(N59); Sap(N60); Sap(N61); Dap(SN1); Dap(SN2); Dap(SN3); Dap(SN4); Dap(SN5); Dap(SN6); Dap(SN7); Dap(SN8); Dap(SN9); Dap(SN10); Dap(SN11); Dap(SN12); Dap(SN13); Dap(SN14); Dap(SN15); Dap(SN16); Dap(SN17); Dap(SN18); Dap(SN19); Dap(SN20); Dap(SN21); Dap(SN22); Dap(SN23); Dap(SN24); Dap(SN25); Dap(SN26); Dap(SN27); Dap(SN28); Dap(SN29); Dap(SN30); Dap(SN31); Dap(SN32); Dap(SN33); Dap(SN34); Dap(SN35); Dap(SN36); Dap(SN37); Dap(SN38); Dap(SN39); Dap(SN40); Dap(SN41); Dap(SN42); Dap(SN43); Dap(SN44); Dap(SN45); Dap(SN46); Dap(SN47); Dap(SN48); Dap(SN49); Dap(SN50); Dap(SN51); Dap(SN52); Dap(SN53); Dap(SN54); Dap(SN55); Dap(SN56); Dap(SN57); Dap(SN58); Dap(SN59); Dap(SN60); Dap(SN61); Dap(UN1); Dap(UN2); Dap(UN3); Dap(UN4); Dap(UN5); Dap(UN6); Dap(UN7); Dap(UN8); Dap(UN9); Dap(UN10); Dap(UN11); Dap(UN12); Dap(UN13); Dap(UN14); Dap(UN15); Dap(UN16); Dap(UN17); Dap(UN18); Dap(UN19); Dap(UN20); Dap(UN21); Dap(UN22); Dap(UN23); Dap(UN24); Dap(UN25); Dap(UN26); Dap(UN27); Dap(UN28); Dap(UN29); Dap(UN30); Dap(UN31); Dap(UN32); Dap(UN33); Dap(UN34); Dap(UN35); Dap(UN36); Dap(UN37); Dap(UN38); Dap(UN39); Dap(UN40); Dap(UN41); Dap(UN42); Dap(UN43); Dap(UN44); Dap(UN45); Dap(UN46); Dap(UN47); Dap(UN48); Dap(UN49); Dap(UN50); Dap(UN51); Dap(UN52); Dap(UN53); Dap(UN54); Dap(UN55); Dap(UN56); Dap(UN57); Dap(UN58); Dap(UN59); Dap(UN60); Dap(UN61); Dap(S1); Dap(S2); Dap(S3); Dap(S4); Dap(S5); Dap(S6); Dap(S7); Dap(S8); Dap(S9); Dap(S10); Dap(S11); Dap(S12); Dap(S13); Dap(S14); Dap(S15); Dap(S16); Dap(S17); Dap(S18); Dap(A1); Dap(A2); Dap(A3); Dap(A4); Dap(A5); Dap(A6); Dap(A7); Dap(A8); Dap(A9); Dap(A10); Dap(A11); Dap(A12); Dap(A13); Dap(A14); Dap(A15); Dap(A16); Dap(A17); Dap(A18); Dap(A19); Dap(A20); Dap(A21); Dap(A22); Dap(A23); Dap(A24); Dap(A25); Dap(A26); Dap(A27); Dap(A28); Dap(A29); Dap(A30); Dap(A31); Dap(A32); Dap(A33); Dap(A34); Dap(A35); Dap(A36); Dap(A37); Dap(A38); Dap(A39); Dap(A40); Dap(A41); Dap(A42); Dap(A43); Dap(A44); Dap(A45); Dap(A46); Dap(A47); Dap(A48); Dap(A49); Dap(A50); Dap(A51); Dap(A52); Dap(A53); Dap(A54); Dap(Suc1); Dap(Suc2); Dap(Suc3); Dap(Suc4); Dap(SucS); Dap(Suc6); Dap(Suc7); Dap(Suc8); Dap(Suc9); or Dap(Suc10); or alternatively His; His(Me); His(Bn); hHis; Lat; Trp; Trp(5OH); Trp(5Cl); Trp(6Cl); Trp(5,6Cl$_2$); Trp(5Br); Trp(6Br); Trp(6CF$_3$); Trp(7Aza); hTrp; Tza; 2 Pal; 3 Pal; 4 Pal; h2 Pal; h3 Pal; h4 Pal; Ala(1Im); Ala(2Im); hAla(1Im); hAla(2Im); Ala(Pyrazinyl); Ala(1Pyrazolyl); Ala(3Pyrazolyl); Ala(2Pyrimidin); Ala(4Pyrimidin); 1 Ala(SPyrimidin); Ala(2Quin); Ala(3Quin); or Ala(4Quin);

or pharmaceutically acceptable salts thereof.

In a further particular embodiment of the invention the elements of general formula (I) are defined as follows $T^1$ is $^D$Pro; $^D$Pip; or $^D$Aze;

$T^2$ is an L or D α-amino acid of one of the formulae

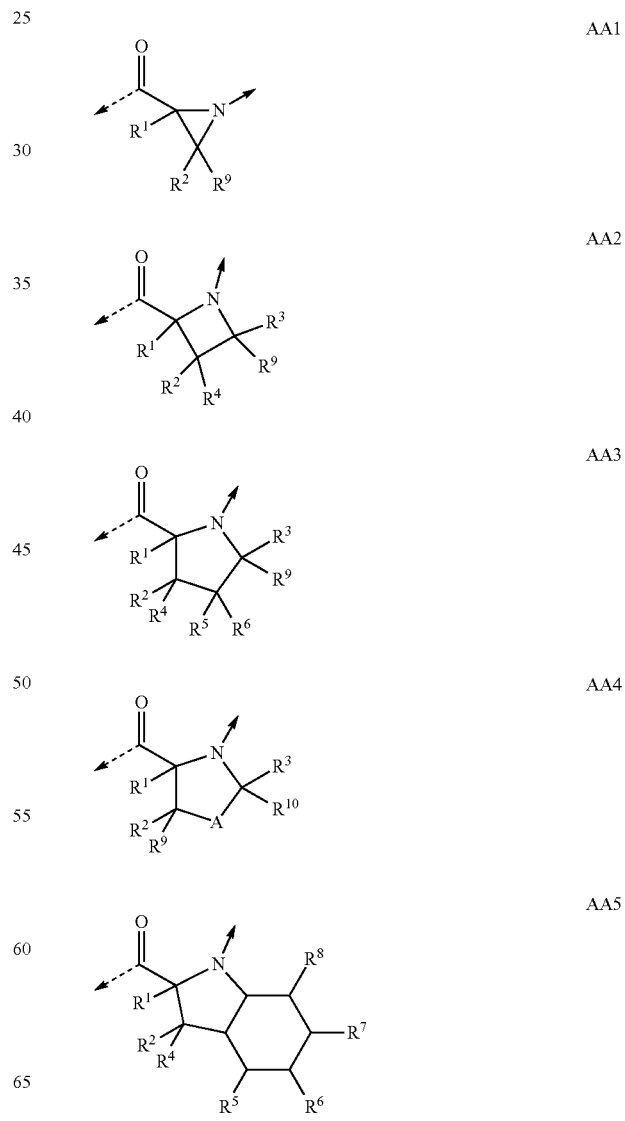

-continued

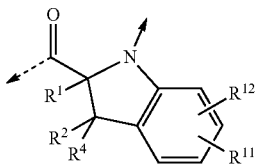
AA6

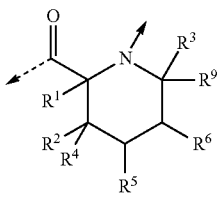
AA7

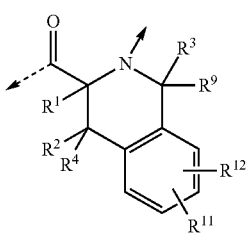
AA8

P¹ and P³ are independently
  His; His(Me); His(Bn); hHis; Phe; Phe(2Cl); Phe(3Cl); Phe(4Cl); Phe(3,4Cl₂); Phe(2F); Phe(3F); Phe(4F); Phe (3,4F₂); Phe(3CN); Phe(4CN); Phe(2CF₃); Phe(3CF₃); Phe(4CF₃); Phe(3,4(CF₃)₂); Phe(4COOMe); hPhe; Thi; Tza; Trp; Trp(5OH); Trp(5Cl); Trp(6Cl); Trp(5,6Cl₂); Trp(5Br); Trp(6Br); Trp(6CF₃); Trp(7Aza); hTrp; Tyr; Tyr(Me); Tyr(Ph); Tyr(Bn); Tyr(4OHPh); Tyr(4MeO-COBn); hTyr; Thr(Bn); Ser(Bn); 2 Pal; 3 Pal; 4 Pal; Phg; Ala(2Furyl); Ala(3Furyl); Ala(2Quin); Ala(3Quin); Ala(4Quin); Ala(tBu); Gly(tBu); 1Nal; 2Nal; Nle(6OBn); Cha; hCha; Bip; Bbta; or OctG;

P² is Aib; Ac3c; Ac4c; Cyp; Chx; Chx(4-oxo); Ac7c; Ac8c; ᴰAtc; ᴸAtc; ᴰᴸ-Atc; Deg; or 4,4-AC-ThioTHP;

P⁴ is Arg; hArg; Ala(Ppz); Thr; alloThr; Gln; Gln(Me); Gln(Me₂); Gln(iPr); Gln(cPr); Gln(iBu); Glu(Ala); Glu(ᴰAla); Glu(Arg); Glu(ᴰArg); Glu(Glu); Glu(Gly); Glu(H is); Glu(Leu); Glu(ᴰLeu); Glu(2Nal); Glu(Sar); Glu(Trp); Glu(ᴰTrp); Cys; hCys; Ser; hSer; Ser(Me); hSer(Me); Thr; Met; Met(O₂); Lys; hLys; Lys(Ac); Lys(Me); Lys(Bz); Lys(Nic); Lys(4Oxa); Lys((5R)OH); Orn; Dap; Dap(MeO(CH₂)₂); Dap(CONH₂); Dap((MeO(CH₂)₂)₂); Dab(Sar); Dab; Dab(Ac); Dab(Ala); Dab(ᴰAla); Dab(Arg); Dab(ᴰArg); Dab(Dab); Dab(Glu); Dab(Gly); Dab(H is); Dab(Leu); Dab(ᴰLeu); Dab(MEMCO); Dab(4Me₂NPhSO₂); Dab(MeO(CH₂)₂NHCO); Dab((MeO(CH₂)₂)(Me)NCO); Dab(MePpzCO); Dab(MeSO₂); Dab(morphCO); Dab(2Nal); Dab(Trp); Dab(ᴰTrp); Dab(Sar); or Dab(SN13); or alternatively His; His(Me); hHis; 2 Pal; 3 Pal; 4 Pal; h2 Pal; h3 Pal; h4 Pal; Trp; Ala(1Im); Ala(2Im); hAla(1Im); hAla(2Im); or Ala(2Pyrimidin);

or pharmaceutically acceptable salts thereof.

In an even further particular embodiment of the invention the elements of general formula (I) are defined as follows
T¹ is ᴰPro; ᴰPip; or ᴰAze;
T² is Pro; ᴰPro; Oic; Pip; Tic; Tic(7OH); Thz; Thz(5,5Me₂); Pro((4S)F); Pro(5,5Me₂); Pro((4S)cHex); Pro((4R)Ph); Pro((4R)Bn); Pro((4R)4BrBn); Pro((4R)3CNBn); Hyp(Ph); Hyp(Bn); Hyp(4BrBn); Hyp(3CNBn); Hyp(4CNBn); Hyp(CONHPh); or (4S)-Hyp(Bn);

P¹ and P³ are independently
  Phe; Phe(4Cl); Phe(4F); Phe(4CN); Phe(3CF₃); Phe(4CF₃); Phe(4COOMe); Trp; Trp(5OH); Trp(6Cl); Tyr; Tyr(Me) Tyr(Ph); Tyr(4OHPh); Tyr(4MeOCOBn); hTyr; Ala(2Furyl); Ala(2Quin); 2Nal; Nle(6OBn); ᴰᴸTrp(7Aza); Cha; Bip; Bbta; or OctG;

P² is Aib; Ac3c; Ac4c; Cyp; Chx; Chx(4oxo); Ac7c; Ac8c; ᴰᴸAtc; Deg;
  or 4,4-AC-ThioTHP;

P⁴ is Arg; hArg; Ala(Ppz); Thr; cilloThr; Gln; Gln(iPr); Gin(cPr); Glu(Ala); Glu(ᴰAla); Glu(Arg); Glu(ᴰArg); Glu(Glu); Glu(Giy); Glu(H is); Glu(Leu); Glu(ᴰLeu); Glu(2Nal); Glu(Sar); Glu(Trp); Glu(ᴰTrp); Cys; hCys; Ser; hSer; Ser(Me); hSer(Me); Thr; Met; Met(O₂); Lys; hLys; Lys(Ac); Lys(Me); Lys(Bz); Lys(Nic); Lys(4Oxa); Lys((5R)OH); Dap; Dap(MeO(CH₂)₂); Dap(CONH₂); Dap((MeO(CH₂)₂)₂); Dab; Dab(Ac); Dab(morphCO); Dab(MePpzCO); Dab(MEMCO); Dab(MeO(CH₂)₂NFICO); Dab((MeO(CH₂)₂)(Me)NCO); Dab(MeSO₂); Dab(4Me₂NPhSO₂); Dab(Dab); or Dab(SN13);
  or alternatively His; hHis; 2 Pal; 3 Pal; or 4 Pal;
or pharmaceutically acceptable salts thereof.

Hereinafter follows a list of abbreviations, corresponding to generally adopted usual practice, of amino acids which, or the residues of which, are suitable for the purposes of the present invention and referred to in this document.

In spite of this specific determination of amino acids, it is noted that, for a person skilled in the art, it is obvious that derivatives of these amino acids, resembling alike structural and physico-chemical properties, lead to functional analogs with similar biological activity, and therefore still form part of the gist of this invention.

Ala L-Alanine
Arg L-Arginine
Asn L-Asparagine
Asp L-Aspartic acid
Cit L-Citrulline
Cys L-Cysteine
Glu L-Glutamic acid
Gln L-Glutamine
Gly Glycine
H is L-Histidine
Ile L-Isoleucine
Leu L-Leucine
Lys L-Lysine
Met L-Methionine
Orn L-Ornithine
Phe L-Phenylalanine
Pro L-Proline
Ser L-Serine
Thr L-Threonine
Trp L-Tryptophan
Tyr L-Tyrosine
Val L-Valine
Ac3c 1-aminocyclopropane carboxylic acid
Ac4c 1-aminocyclobutane carboxylic acid
Ac7c 1-aminocycloheptane carboxylic acid
Ac8c 1-aminocyclooctane carboxylic acid
Ala(tBu) (S)-2-amino-4,4-dimethylpentanoic acid
Ala(2Furyl) (S)-2-amino-3-(furan-2-yl)propanoic acid
Ala(3Furyl) (S)-2-amino-3-(furan-3-yl)propanoic acid
Ala(1Im) (S)-2-amino-3-(1H-imidazol-1-yl)propanoic acid
Ala(2Im) (S)-2-amino-3-(1H-imidazol-2-yl)propanoic acid
Ala(Ppz) (S)-2-amino-3-(piperazin-1-yl)propanoic acid
Ala(Pyrazinyl) (S)-2-amino-3-(pyrazin-2-yl)propanoic acid
Ala(1Pyrazolyl) (S)-2-amino-3-(1H-pyrazol-1-yl)propanoic acid Ala(3Pyrazolyl) (S)-2-amino-3-(1H-pyrazol-3-yl)propanoic acid
Ala(2Pyrimidin) (S)-2-amino-3-(pyrimidin-2-yl)propanoic acid
Ala(4Pyrimidin) (S)-2-amino-3-(pyrimidin-4-yl)propanoic acid
Ala(5Pyrimidin) (S)-2-amino-3-(pyrimidin-5-yl)propanoic acid
Ala(2Quin) (S)-2-amino-3-(quinolin-2-yl)propanoic acid
Ala(3Quin) (S)-2-amino-3-(quinolin-3-yl)propanoic acid
Ala(4Quin) (S)-2-amino-3-(quinolin-4-yl)propanoic acid
Aib 2-methyl-2-aminopropanoic acid
$^{DL}$Atc (R,S)-2-amino-1,2,3,4-tetrahydronaphthalene-2-carboxylic acid
Aze (S)-azetidine-2-carboxylic acid
4,4-AC-ThioTHP 4-aminotetrahydro-2H-thiopyran-4-carboxylic acid
Bbta (S)-2-amino-3-(1-benzothiophen-3-yl)propanoic acid
Bip (S)-2-amino-3-(4-biphenylyl)propanoic acid
Cha (S)-2-amino-3-cyclohexylpropanoic acid
Chx 1-aminocyclohexane carboxylic acid
Chx(4-oxo) 1-amino-4-oxo-cyclohexane carboxylic acid
Cyp 1-aminocyclopentane carboxylic acid
Dab (S)-2,4-diaminobutanoic acid
Dab(Ac) (S)-4-acetamido-2-aminobutanoic acid
Dab(Ala) (S)-2-amino-4-((S)-2-aminopropanamido)butanoic acid
Dab($^D$Ala) (S)-2-amino-4-((R)-2-aminopropanamido)butanoic acid
Dab(Arg) (S)-2-amino-4-((S)-2-amino-5-guanidinopentanamido)butanoic acid
Dab($^D$Arg) (S)-2-amino-4-((R)-2-amino-5-guanidinopentanamido)butanoic acid
Dab(Dab) (5)-2-amino-44(S)-2,4-diaminobutanamido)butanoic acid
Dab(Glu) (S)-4-amino-5-((S)-3-amino-3-carboxypropylamino)-5-oxopentanoic acid
Dab(Gly) (S)-2-amino-4-(2-aminoacetamido)butanoic acid
Dab(H is) (S)-2-amino-4-((S)-2-amino-3-(1H-imidazol-5-yl)-propanamido)butanoic acid
Dab(Leu) (S)-2-amino-4-((S)-2-amino-4-methylpentanamido)butanoic acid
Dab($^D$Leu) (S)-2-amino-4-((R)-2-amino-4-methylpentanamido)butanoic acid
Dab(MEMCO) (S)-2-amino-4-(2-(2-methoxyethoxy)acetamido)butanoic acid
Dab(4Me$_2$NPhSO$_2$) (S)-2-amino-4-(4-(dimethylamino)phenylsulfonamido)butanoic acid
Dab(MeO(CH$_2$)$_2$NHCO) (S)-2-amino-4-(3-(2-methoxyethyl)ureido)butanoic acid
Dab((MeO(CH$_2$)$_2$)(Me)NCO) (S)-2-amino-4-(3-(2-methoxyethyl)-3-methylureido)-butanoic acid
Dab(MePpzCO) (S)-2-amino-4-(4-methylpiperazine-1-carboxamido)butanoic acid
Dab(MeSO$_2$) (S)-2-amino-4-(methylsulfonamido)butanoic acid
Dab(morphCO) (S)-2-amino-4-(morpholine-4-carboxamido)butanoic acid
Dab(2Nal) (S)-2-amino-4-((S)-2-amino-3-(naphthalen-2-yl)-propanamido)butanoic acid
Dab(Trp) (S)-2-amino-4-((S)-2-amino-3-(1H-indol-3-yl)propanamido)-butanoic acid
Dab($^D$Trp) (S)-2-amino-4-((R)-2-amino-3-(1H-indol-3-yl)propanamido)-butanoic acid
Dab(Sar) (S)-2-amino-4-(2-(methylamino)acetamido)butanoic acid
Dap (S)-2,4-diaminopropanoic acid
Dap(CONH$_2$) (S)-2-amino-3-ureidopropanoic acid
Dap(MeO(CH$_2$)$_2$) (S)-2-amino-3-(2-methoxyethylamino)propanoic acid
Dap((MeO(CH$_2$)$_2$)$_2$) (S)-2-amino-3-(bis(2-methoxyethyl)amino)propanoic acid
Dab(Sar) (S)-2-amino-3-(2-(methylamino)acetamido)propanoic acid
Deg 2-amino-2-ethylbutanoic acid
Gly(tBu) (S)-2-amino-3,3-dimethylbutanoic acid
Gln(iBu) (S)-2-amino-5-(isobutylamino)-5-oxopentanoic acid
Gln(Me) (S)-2-amino-5-(methylamino)-5-oxopentanoic acid
Gln(Me$_2$) (S)-2-amino-5-(dimethylamino)-5-oxopentanoic acid
Gln(iPr) (S)-2-amino-5-(isopropylamino)-5-oxopentanoic acid
Gln(cPr) (S)-2-amino-5-(cyclopropylamino)-5-oxopentanoic acid
Glu(Ala) (S)-2-amino-5-((S)-1-carboxyethylamino)-5-oxopentanoic acid
Glu($^D$Ala) (S)-2-amino-5-((R)-1-carboxyethylamino)-5-oxopentanoic acid
Glu(Arg) (S)-2-amino-5-((S)-1-carboxy-4-guanidinobutylamino)-5-oxopentanoic acid
Glu($^D$Arg) (S)-2-amino-5-((R)-1-carboxy-4-guanidinobutylamino)-5-oxopentanoic acid
Glu(Glu) (S)-2-((S)-4-amino-4-carboxybutanamido)pentanedioic acid
Glu(Gly) (S)-2-amino-5-(carboxymethylamino)-5-oxopentanoic acid
Glu(His) (S)-2-amino-5-((S)-1-carboxy-2-(1H-imidazol-5-yl)ethylamino)-5-oxopentanoic acid
Glu(Leu) (S)-2-amino-5-((S)-1-carboxy-3-methylbutylamino)-5-oxopentanoic acid
Glu($^D$Leu) (S)-2-amino-5-((R)-1-carboxy-3-methylbutylamino)-5-oxopentanoic acid
Glu(2Nal) (S)-2-amino-5-((S)-1-carboxy-2-(naphthalen-2-yl)ethylamino)-5-oxopentanoic acid
Glu(Sar) (S)-2-amino-5-((carboxymethyl)(methyl)amino)-5-oxopentanoic acid
Glu(Trp) (S)-2-amino-5-((S)-1-carboxy-2-(1H-indol-3-yl)ethylamino)-5-oxopentanoic acid
Glu($^D$Trp) (S)-2-amino-5-((R)-1-carboxy-2-(1H-indol-3-yl)ethylamino)-5-oxopentanoic acid
hAla(1Im) (S)-2-amino-3-(1H-imidazol-1-yl)-butanoic acid
hAla(2Im) (S)-2-amino-3-(1H-imidazol-2-yl)-butanoic acid
hArg (S)-2-amino-6-guanidinohexanoic acid
hCha (S)-2-amino-4-cyclohexylbutanoic acid
hCys (S)-2-amino-4-mercaptobutanoic acid
hHis (S)-2-amino-4-(1H-imidazol-5-yl)butanoic acid
hLys (S)-2,7-diaminoheptanoic acid
h2 Pal (S)-2-amino-4-(pyridin-2-yl)-butanoic acid
h3 Pal (S)-2-amino-3-(pyridine-3-yl)-butanoic acid
h4 Pal (S)-2-amino-3-(pyridine-4-yl)-butanoic acid
hPhe (S)-2-amino-4-phenylbutanoic acid
hSer (S)-2-amino-4-hydroxybutanoic acid
hSer(Me) (S)-2-amino-4-methoxybutanoic acid
hTrp (S)-2-amino-4-(1H-indol-3-yl)butanoic acid
hTyr (S)-2-amino-4-(4-hydroxyphenyl)butanoic acid
His(Me) (S)-2-amino-3-(1-methyl-1H-imidazol-5-yl)propanoic acid
His(Bn) (S)-2-amino-3-(1-benzyl-1H-imidazol-5-yl)propanoic acid
Hyp(Bn) (2S,4R)-4-(benzyloxy)pyrrolidine-2-carboxylic acid (4S)-Hyp(Bn) (2S,4S)-4-(benzyloxy)pyrrolidine-2-carboxylic acid
Hyp(4BrBn) (2S,4R)-4-(4-bromobenzyloxy)pyrrolidine-2-carboxylic acid
Hyp(3CNBn) (2S,4R)-4-(3-cyanobenzyloxy)pyrrolidine-2-carboxylic acid
Hyp(4CNBn) (2S,4R)-4-(4-cyanobenzyloxy)pyrrolidine-2-carboxylic acid
Hyp(CONHPh) (2S,4R)-4-(phenylcarbamoyloxy)pyrrolidine-2-carboxylic acid
Hyp(Ph) (1S,4R)-4-phenoxypyrrolidine-2-carboxylic acid
Lat (S)-2-amino-3-(2-aminopyrimidin-4-yl)propanoic acid
Lys(Ac) (S)-6-acetamido-2-aminohexanoic acid
Lys(Bz) (S)-2-amino-6-benzamidohexanoic acid
Lys(Me) (S)-2-amino-6-(methylamino)hexanoic acid
Lys(Nic) (S)-2-amino-6-(nicotinamido)hexanoic acid
Lys((5R)OH) (2S,5R)-2,6-diamino-5-hydroxyhexanoic acid
Lys(4Oxa) (S)-2-amino-3-(2-aminoethoxy)propanoic acid
Met(O$_2$) (S)-2-amino-4-(methylsulfonyl)butanoic acid
1Nal (S)-2-amino-3-naphthalen-1-ylpropanoic acid
2Nal (S)-2-amino-3-naphthalen-2-ylpropanoic acid
Nle (S)-2-amino-hexanoic acid
Nle(6OBn) (S)-2-amino-6-(benzyloxy)hexanoic acid
OctG (S)-2-aminodecanoic acid
Oic (2S,3aS,7aS)-octahydro-1H-indole-2-carboxylic acid
2 Pal (S)-2-amino-3-(pyridine-2-yl) propionic acid
3 Pal (S)-2-amino-3-(pyridine-3-yl)propionic acid
4 Pal (S)-2-amino-3-(pyridine-4-yl)propionic acid
Phe(2Cl) (S)-2-amino-3-(2-chlorophenyl)propanoic acid
Phe(3Cl) (S)-2-amino-3-(3-chlorophenyl)propanoic acid
Phe(4Cl) (S)-2-amino-3-(4-chlorophenyl)propanoic acid
Phe(3,4Cl$_2$) (S)-2-amino-3-(3,4-dichlorophenyl)propanoic acid
Phe(2F) (S)-2-amino-3-(2-fluorophenyl)propanoic acid
Phe(3F) (S)-2-amino-3-(3-fluorophenyl)propanoic acid
Phe(4F) (S)-2-amino-3-(4-fluorophenyl)propanoic acid
Phe(4CN) (S)-2-amino-3-(4-cyanophenyl)propanoic acid
Phe(4CF$_3$) (S)-2-amino-3-(4-(trifluoromethyl))propanoic acid
Phe(4COOMe) (S)-2-amino-3-(4-(methoxycarbonyl)phenyl)propanoic acid
Phg (S)-2-amino-2-phenylacetic acid
Pip (S)-piperidine-2-carboxylic acid
Pro((4R)$_4$BrBn) (2S,4R)-4-(4-bromobenzyl)pyrrolidine-2-carboxylic acid
Pro((4R)Bn) (2S,4R)-4-benzylpyrrolidine-2-carboxylic acid
Pro((4R)$_3$CNBn) (2S,4R)-4-(3-cyanobenzyl)pyrrolidine-2-carboxylic acid
Pro((4S)F) (2S,4S)-4-fluoropyrrolidine-2-carboxylic acid
Pro((4S)$_c$Hex) (2S,4S)-4-cyclohexylpyrrolidine-2-carboxylic acid
Pro(5,5Me$_2$) (S)-3,3-dimethylpyrrolidine-2-carboxylic acid
Pro((4R)Ph) (2S,4R)-4-phenylpyrrolidine-2-carboxylic acid
Ser(Bn) (S)-2-amino-3-(benzyloxy)propanoic acid
Ser(Me) (S)-2-amino-3-methoxy-propanoic acid
Thi (S)-2-amino-3-(thiophen-2-yl)propanoic acid
alloThr (2S,3S)-2-amino-3-hydroxybutanoic acid
Thr(Bn) (2S,3R)-2-amino-3-(benzyloxy)butanoic acid
Thz (4R)-1,3-thiazolidine-4-carboxylic acid
Thz(5,5Me$_2$) (4R)-5,5-dimethyl-1,3-thiazolidine-4-carboxylic acid
Tic (3S)-1,2,3,4-Tetrahydroisoquinoline-3-carboxylic acid
Tic(7OH) (3S)-7-hydroxy-1,2,3,4-tetrahydroisoquinoline-3-carboxylic acid
$^{DL}$Trp(7Aza) (RS)-2-amino-3-(1H-pyrrolo[2,3-b]pyridin-3-yl)propanoic acid
Trp(5Br) (S)-2-amino-3-(5-bromo-1H-indol-3-yl)propanoic acid
Trp(6Br) (S)-2-amino-3-(6-bromo-1H-indol-3-yl)propanoic acid
Trp(6CF$_3$) (S)-2-amino-3-(6-(trifluoromethyl)-1H-indol-3-yl)propanoic acid
Trp(5Cl) (S)-2-amino-3-(5-chloro-1H-indol-3-yl)propanoic acid
Trp(6Cl) (S)-2-amino-3-(6-chloro-1H-indol-3-yl)propanoic acid
Trp(5,6Cl) (S)-2-amino-3-(5,6-dichloro-1H-indol-3-yl)propanoic acid
Trp(5OH) (S)-2-amino-3-(5-hydroxy-1H-indol-3-yl)propanoic acid
Tyr(Bn) (S)-2-amino-3-(4-(benzyloxy)phenyl)propanoic acid
Tyr(Me) (S)-2-amino-3-(4-methoxyphenyl)propanoic acid
Tyr(4MeOCOBn) (S)-2-amino-3-(4-(4-(methoxycarbonyl)benzyloxy)phenyl)-propanoic acid
Tyr(Ph) (S)-2-amino-3-(4-phenoxyphenyl)propanoic acid
Tyr(4OHPh) (S)-2-amino-3-[4-(4-hydroxyphenoxy)phenyl]propanoic acid
Tza (S)-2-amino-3-(thiazol-4-yl)propanoic acid
Gln(Alk1) (S)-2-amino-5-oxo-5-(2,2,2-trifluoroethylamino) pentanoic acid
Gln(Alk2) (S)-2-amino-5-(cyclopentylamino)-5-oxopentanoic acid
Gln(Alk3) (S)-2-amino-5-(cyclohexylamino)-5-oxopentanoic acid
Gln(Alk4) (S)-2-amino-5-oxo-5-(tetrahydro-2H-pyran-4-ylamino)pentanoic acid
Gln(Alk5) (S)-2-amino-5-(2-hydroxyethylamino)-5-oxopentanoic acid
Gln(Alk6) (S)-2-amino-5-(2-methoxyethylamino)-5-oxopentanoic acid
Gln(Alk7) (S)-2-amino-5-(2-aminoethylamino)-5-oxopentanoic acid
Gln(Alk8) (S)-2-amino-5-(2-(dimethylamino)ethylamino)-5-oxopentanoic acid
Gln(Alk9) (S)-2-amino-5-((2-methoxyethyl)(methyl)amino)-5-oxopentanoic acid
Gln(Alk10) (S)-2-amino-5-((2-(dimethylamino)ethyl)(methyl)amino)-5-oxopentanoic acid
Gln(Alk11) (S)-2-amino-5-(3-aminopropylamino)-5-oxopentanoic acid
Gln(Alk12) (S)-2-amino-5-(3-(dimethylamino)propylamino)-5-oxopentanoic acid
Gln(Alk13) (S)-2-amino-5-((3-(dimethylamino)propyl)(methyl)amino)-5-oxopentanoic acid
Gln(Alk14) (S)-5-(3-acetamidopropylamino)-2-amino-5-oxopentanoic acid
Gln(Alk15) (S)-2-amino-5-oxo-5-(2-(pyrrolidin-1-yl)ethylamino)pentanoic acid
Gln(Alk16) (S)-2-amino-5-(2-morpholinoethylamino)-5-oxopentanoic acid
Gln(Alk17) (S)-2-amino-5-(3-morpholinopropylamino)-5-oxopentanoic acid
Gln(Alk18) (S)-2-amino-5-(1,3-dihydroxypropan-2-ylamino)-5-oxopentanoic acid
Gln(Alk19) (S)-2-amino-5-(4-hydroxy-3-(hydroxymethyl)butylamino)-5-oxopentanoic acid
Gln(Alk20) (S)-2-amino-5-oxo-5-(piperidin-4-ylmethylamino)pentanoic acid
Gln(Alk21) (S)-2-amino-5-(methyl((tetrahydro-2H-pyran-4-yl)methyl)amino)-5-oxopentanoic acid
Gln(Alk22) (2S)-2-amino-5-(methyl(2-(1-methylpyrrolidin-2-yl)ethyl)amino)-5-oxopentanoic acid Gln(Alk23) (S)-2-amino-5-oxo-5-(thiazol-2-ylmethylamino)pentanoic acid
Gln(Alk24) (S)-2-amino-5-((1-methyl-1H-imidazol-4-yl)methylamino)-5-oxopentanoic acid
Gln(Alk25) (S)-2-amino-5-(benzylamino)-5-oxopentanoic acid
Gln(Alk26) (S)-2-amino-5-(4-(methylsulfonyl)benzylamino)-5-oxopentanoic acid
Gln(Alk27) (S)-2-amino-5-oxo-5-(pyridin-3-ylmethylamino)pentanoic acid
Gln(Alk28) (S)-2-amino-5-oxo-5-(4-(trifluoromethyl)benzylamino)pentanoic acid
Gln(Alk29) (S)-2-amino-5-(2-methoxybenzylamino)-5-oxopentanoic acid
Gln(Alk30) (S)-2-amino-5-((1-methyl-1H-benzo[d]imidazol-2-yOmethylamino)-5-oxopentanoic acid
Gln(Alk31) (S)-2-amino-5-((4-methyl-6-(trifluoromethyl)pyrimidin-2-yl)-methylamino)-5-oxopentanoic acid
Gln(Alk32) (S)-5-(2-(1H-indol-3-yl)ethylamino)-2-amino-5-oxopentanoic acid
Gln(Alk33) (2S)-2-amino-5-(2,3-dihydro-1H-inden-1-ylamino)-5-oxopentanoic acid
Gln(Alk34) (2S)-2-amino-5-oxo-5-(1,2,3,4-tetrahydronaphthalen-1-ylamino)-pentanoic acid
Glu(cN1) (S)-2-amino-5-(azetidin-1-yl)-5-oxopentanoic acid
Glu(cN2) (S)-2-amino-5-oxo-5-(pyrrolidin-1-yl)pentanoic acid
Glu(cN3) (S)-2-amino-5-oxo-5-(piperidin-1-yl)pentanoic acid
Glu(cN4) (S)-2-amino-5-morpholino-5-oxopentanoic acid
Glu(cN5) (S)-2-amino-5-oxo-5-(piperazin-1-yl)pentanoic acid
Glu(cN6) (S)-2-amino-5-(4-methylpiperazin-1-yl)-5-oxopentanoic acid
Glu(cN7) (S)-2-amino-5-(4-hydroxypiperidin-1-yl)-5-oxopentanoic acid
Glu(cN8) (S)-2-amino-5-(4-(dimethylamino)piperidin-1-yl)-5-oxopentanoic acid
Glu(cN9) (2S)-2-amino-5-(7-methyl-1,7-diazaspiro[4.4]nonan-1-yl)-5-oxopentanoic acid
Glu(cN10) (S)-2-amino-5-(indolin-1-yl)-5-oxopentanoic acid
Glu(cN11) (S)-2-amino-5-(5,6-dihydro-1,7-naphthyridin-7(8H)-yl)-5-oxopentanoic acid
Glu(cN12) (S)-2-amino-5-(3,4-dihydro-1,5-naphthyridin-1(2H)-yl)-5-oxopentanoic acid
Glu(cN13) (S)-2-amino-5-(5,6-dihydroimidazo[1,2-a]pyrazin-7(8H)-yl)-5-oxopentanoic acid
Glu(cN14) (S)-5-(4-(1H-imidazol-1-yppiperidin-1-yl)-2-amino-5-oxopentanoic acid
Glu(cN15) (S)-5-(4-(1H-imidazol-2-yppiperidin-1-yl)-2-amino-5-oxopentanoic acid
Glu(cN16) (S)-2-amino-5-(1,4-oxazepan-4-yl)-5-oxopentanoic acid
Glu(cN17) (S)-2-amino-5-(4-methyl-1,4-diazepan-1-yl)-5-oxopentanoic acid
Sab(N1) (S)-2-amino-4-sulfamoylbutanoic acid
Sab(N2) (S)-2-amino-4-(N-methylsulfamoyl)butanoic acid
Sab(N3) (S)-2-amino-4-(N,N-dimethylsulfamoyl)butanoic acid
Sab(N4) (S)-2-amino-4-(N-isopropylsulfamoyl)butanoic acid
Sab(N5) (S)-2-amino-4-(N-cyclopropylsulfamoyl)butanoic acid
Sab(N6) (S)-2-amino-4-(N-isobutylsulfamoyl)butanoic acid
Sab(N7) (S)-2-amino-4-(N-(2,2,2-trifluoroethyl)sulfamoyl)butanoic acid
Sab(N8) (S)-2-amino-4-(azetidin-1-ylsulfonyl)butanoic acid
Sab(N9) (S)-2-amino-4-(pyrrolidin-1-ylsulfonyl)butanoic acid
Sab(N10) (S)-2-amino-4-(piperidin-1-ylsulfonyl)butanoic acid
Sab(N11) (S)-2-amino-4-(morpholinosulfonyl)butanoic acid
Sab(N12) (S)-2-amino-4-(piperazin-1-ylsulfonyl)butanoic acid
Sab(N13) (S)-2-amino-4-(4-methylpiperazin-1-ylsulfonyl)butanoic acid
Sab(N14) (S)-4-(4-acetylpiperazin-1-ylsulfonyl)-2-aminobutanoic acid
Sab(N15) (S)-2-amino-4-(4-hydroxypiperidin-1-ylsulfonyl)butanoic acid
Sab(N16) (2S)-2-amino-4-(2-methyl-1-oxo-2,6-diazaspiro[4.5]decan-6-ylsulfonyl)-butanoic acid
Sab(N17) (S)-2-amino-4-(4-(dimethylamino)piperidin-1-ylsulfonyl)butanoic acid
Sab(N18) (15)-2-amino-4-(7-methyl-1,7-diazaspiro[4.4]nonan-1-ylsulfonyl)-butanoic acid
Sab(N19) (S)-2-amino-4-(2,2-dimethylpyrrolidin-1-ylsulfonyl)butanoic acid
Sab(N20) (S)-2-amino-4-(N-cyclopentylsulfamoyl)butanoic acid
Sab(N21) (S)-2-amino-4-(N-cyclohexylsulfamoyl)butanoic acid
Sab(N22) (S)-2-amino-4-(N-(tetrahydro-2H-pyran-4-yl)sulfamoyl)butanoic acid
Sab(N23) (S)-2-amino-4-(N-(2-hydroxyethyl)sulfamoyl)butanoic acid
Sab(N24) (S)-2-amino-4-(N-(2-methoxyethyl)sulfamoyl)butanoic acid
Sab(N25) (S)-2-amino-4-(N-(2-aminoethyl)sulfamoyl)butanoic acid
Sab(N26) (S)-2-amino-4-(N-(2-(dimethylamino)ethyl)sulfamoyl)butanoic acid
Sab(N27) (S)-2-amino-4-(N-(2-methoxyethyl)-N-methylsulfamoyl)butanoic acid
Sab(N28) (S)-2-amino-4-(N-(2-(dimethylamino)ethyl)-N-methylsulfamoyl)-butanoic acid
Sab(N29) (S)-2-amino-4-(N-(3-aminopropyl)sulfamoyl)butanoic acid
Sab(N30) (S)-2-amino-4-(N-(3-(dimethylamino)propyl)sulfamoyl)butanoic acid
Sab(N31) (S)-2-amino-4-(N-(3-(dimethylamino)propyl)-N-methylsulfamoyl)-butanoic acid
Sab(N32) (S)-4-(N-(2-acetamidoethyl)sulfamoyl)-2-aminobutanoic acid
Sab(N33) (S)-2-amino-4-(N-(2-(pyrrolidin-1-yl)ethyl)sulfamoyl)butanoic acid
Sab(N34) (S)-2-amino-4-(N-(2-morpholinoethyl)sulfamoyl)butanoic acid
Sab(N35) (S)-2-amino-4-(N-(3-morpholinopropyl)sulfamoyl)butanoic acid
Sab(N36) (S)-2-amino-4-(N-(1,3-dihydroxypropan-2-yl)sulfamoyl)butanoic acid
Sab(N37) (S)-2-amino-4-(N-(4-hydroxy-3-(hydroxymethypbutyl)sulfamoyl)-butanoic acid
Sab(N38) (S)-2-amino-4-(N-(piperidin-4-ylmethyl)sulfamoyl)butanoic acid
Sab(N39) (S)-2-amino-4-(N-methyl-N-((tetrahydro-2H-pyran-4-yl)methyl)-sulfamoyl)butanoic acid
Sab(N40) (2S)-2-amino-4-(N-methyl-N-(2-(1-methylpyrrolidin-2-yl)ethyl)-sulfamoyl)-butanoic acid Sab(N41) (S)-2-amino-4-(N-(thiazol-2-ylmethyl)sulfamoyl)butanoic acid
Sab(N42) (S)-2-amino-4-(N4(1-methyl-1H-imidazol-4-yOmethyl)-sulfamoyl)butanoic acid
Sab(N43) (S)-2-amino-4-(N-benzylsulfamoyl)butanoic acid
Sab(N44) (S)-2-amino-4-(N-(4-(methylsulfonyl)benzyl)sulfamoyl)butanoic acid
Sab(N45) (S)-2-amino-4-(N-(pyridin-3-ylmethyl)sulfamoyl)butanoic acid
Sab(N46) (S)-2-amino-4-(N-(4-(trifluoromethyl)benzyl)sulfamoyl)butanoic acid
Sab(N47) (S)-2-amino-4-(N-(2-methoxybenzyl)-N-methylsulfamoyl)butanoic acid
Sab(N48) (S)-2-amino-4-(N-((1-methyl-1H-benzo[d]imidazol-2-yl)methyl)-sulfamoyl)butanoic acid
Sab(N49) (S)-2-amino-4-(N-((4-methyl-6-(trifluoromethyl)pyrimidin-2-yOmethyl)-sulfamoyl)butanoic acid
Sab(N50) (S)-4-(N-(2-(1H-indol-2-yl)ethyl)sulfamoyl)-2-aminobutanoic acid
Sab(N51) (S)-2-amino-4-(indolin-1-ylsulfonyl)butanoic acid
Sab(N52) (S)-2-amino-4-(5,6-dihydro-1,7-naphthyridin-7(8H)-ylsulfonyl)-butanoic acid
Sab(N53) (S)-2-amino-4-(3,4-dihydro-1,5-naphthyridin-1(2H)-ylsulfonyl)-butanoic acid
Sab(N54) (S)-2-amino-4-(5,6-dihydroimidazo[1,2-c]pyrazin-7(8H)-ylsulfonyl)-butanoic acid
Sab(N55) (S)-4-(4-(1H-imidazol-1-yl)piperidin-1-ylsulfonyl)-2-aminobutanoic acid
Sab(N56) (S)-4-(4-(1H-imidazol-2-yppiperidin-1-ylsulfonyl)-2-aminobutanoic acid
Sab(N57) (S)-4-(1,4-oxazepan-4-ylsulfonyl)-2-aminobutanoic acid
Sab(N58) (S)-2-amino-4-(4-methyl-1,4-diazepan-1-ylsulfonyl)butanoic acid
Sab(N59) (2S)-2-amino-4-(N-(2,3-dihydro-1H-inden-1-yl)sulfamoyl)butanoic acid
Sab(N60) (2S)-2-amino-4-(N-(1,2,3,4-tetrahydronaphthalen-1-yl)sulfamoyl)-butanoic acid
Sab(N61) (S)-2-amino-4-(4-(2-hydroxyethyl)piperazin-1-ylsulfonyl)butanoic acid
Dab(SN1) (S)-2-amino-4-(sulfamoylamino)butanoic acid
Dab(SN2) (S)-2-amino-4-(N-methylsulfamoylamino)butanoic acid
Dab(SN3) (S)-2-amino-4-(N,N-dimethylsulfamoylamino)butanoic acid
Dab(SN4) (S)-2-amino-4-(N-isopropylsulfamoylamino)butanoic acid
Dab(SN5) (S)-2-amino-4-(N-cyclopropylsulfamoylamino)butanoic acid
Dab(SN6) (S)-2-amino-4-(N-isobutylsulfamoylamino)butanoic acid
Dab(SN7) (S)-2-amino-4-(N-(2,2,2-trifluoroethyl)sulfamoylamino)butanoic acid
Dab(SN8) (S)-2-amino-4-(azetidin-1-ylsulfonylamino)butanoic acid
Dab(SN9) (S)-2-amino-4-(pyrrolidin-1-ylsulfonylamino)butanoic acid
Dab(SN10) (S)-2-amino-4-(piperidin-1-ylsulfonylamino)butanoic acid
Dab(SN11) (S)-2-amino-4-(morpholinosulfonylamino)butanoic acid
Dab(SN12) (S)-2-amino-4-(piperazin-1-ylsulfonylamino)butanoic acid
Dab(SN13) (S)-2-amino-4-(4-methylpiperazin-1-ylsulfonylamino)butanoic acid
Dab(SN14) (S)-4-(4-acetylpiperazin-1-ylsulfonylamino)-2-aminobutanoic acid
Dab(SN15) (S)-2-amino-4-(4-hydroxypiperidin-1-ylsulfonylamino)butanoic acid
Dab(SN16) (2S)-2-amino-4-(2-methyl-1-oxo-2,6-diazaspiro[4.5]clecan-6-yl-sulfonylamino)butanoic acid
Dab(SN17) (S)-2-amino-4-(4-(dimethylamino)piperidin-1-ylsulfonylamino)-butanoic acid
Dab(SN18) (2S)-2-amino-4-(7-methyl-1,7-diazaspiro[4.4]nonan-1-ylsulfonylamino)-butanoic acid
Dab(SN19) (S)-2-amino-4-(2,2-dimethylpyrrolidin-1-ylsulfonylamino)butanoic acid
Dab(SN20) (S)-2-amino-4-(N-cyclopentylsulfamoylamino)butanoic acid
Dab(SN21) (S)-2-amino-4-(N-cyclohexylsulfamoylamino)butanoic acid
Dab(SN22) (S)-2-amino-4-(N-(tetrahydro-2H-pyran-4-yl)sulfamoylamino)butanoic acid
Dab(SN23) (S)-2-amino-4-(N-(2-hydroxyethyl)sulfamoylamino)butanoic acid
Dab(SN24) (S)-2-amino-4-(N-(2-methoxyethyl)sulfamoylamino)butanoic acid
Dab(SN25) (S)-2-amino-4-(N-(2-aminoethyl)sulfamoylamino)butanoic acid
Dab(SN26) (S)-2-amino-4-(N-(2-(dimethylamino)ethyl)sulfamoylamino)butanoic acid
Dab(SN27) (S)-2-amino-4-(N-(2-methoxyethyl)-N-methylsulfamoylamino)-butanoic acid
Dab(SN28) (S)-2-amino-4-(N-(2-(dimethylamino)ethyl)-N-methylsulfamoylamino)-butanoic acid
Dab(SN29) (S)-2-amino-4-(N-(3-aminopropyl)sulfamoylamino)butanoic acid
Dab(SN30) (S)-2-amino-4-(N-(3-(dimethylamino)propyl)sulfamoylamino)butanoic acid
Dab(SN31) (S)-2-amino-4-(N-(3-(dimethylamino)propyl)-N-methylsulfamoylamino)-butanoic acid
Dab(SN32) (S)-4-(N-(2-acetamidoethyl)sulfamoylamino)-2-aminobutanoic acid
Dab(SN33) (S)-2-amino-4-(N-(2-(pyrrolidin-1-yl)ethyl)sulfamoylamino)butanoic acid
Dab(SN34) (S)-2-amino-4-(N-(2-morpholinoethyl)sulfamoylamino)butanoic acid
Dab(SN35) (S)-2-amino-4-(N-(3-morpholinopropyl)sulfamoylamino)butanoic acid
Dab(SN36) (S)-2-amino-4-(N-(1,3-dihydroxypropan-2-yl)sulfamoylamino)-butanoic acid
Dab(SN37) (S)-2-amino-4-(N-(4-hydroxy-3-(hydroxymethyl)butyl)-sulfamoylamino)butanoic acid
Dab(SN38) (S)-2-amino-4-(N-(piperidin-4-ylmethyl)sulfamoylamino)butanoic acid
Dab(SN39) (S)-2-amino-4-(N-methyl-N-((tetrahydro-2H-pyran-4-yl)methyl)-sulfamoylamino)butanoic acid
Dab(SN40) (2S)-2-amino-4-(N-methyl-N-(2-(1-methylpyrrolidin-2-yl)ethyl)-sulfamoylamino)butanoic acid
Dab(SN41) (S)-2-amino-4-(N-(thiazol-2-ylmethyl)sulfamoylamino)butanoic acid
Dab(SN42) (S)-2-amino-4-(N-((1-methyl-1H-imidazol-4-yOmethyl)-sulfamoylamino)butanoic acid
Dab(SN43) (S)-2-amino-4-(N-benzylsulfamoylamino)butanoic acid
Dab(SN44) (S)-2-amino-4-(N-(4-(methylsulfonyl)benzyl)sulfamoylamino)butanoic acid
Dab(SN45) (S)-2-amino-4-(N-(pyridin-3-ylmethyl)sulfamoylamino)butanoic acid
Dab(SN46) (S)-2-amino-4-(N-(4-(trifluoromethyl)benzyl)sulfamoylamino)butanoic acid Dab(SN47) (S)-2-amino-4-(N-(2-methoxybenzyl)-N-methylsulfamoylamino)-butanoic acid
Dab(SN48) (S)-2-amino-4-(N-((1-methyl-1H-benzo[d]imidazol-2-yOmethyl)-sulfamoylamino)butanoic acid
Dab(SN49) (S)-2-amino-4-(N-((4-methyl-6-(trifluoromethyl)pyrimidin-2-yOmethyl)-sulfamoylamino)butanoic acid
Dab(SN50) (S)-4-(N-(2-(1H-indol-2-yl)ethyl)sulfamoylamino)-2-aminobutanoic acid
Dab(SN51) (S)-2-amino-4-(indolin-1-ylsulfonylamino)butanoic acid
Dab(SN52) (S)-2-amino-4-(5,6,7,8-tetrahydro-1,7-naphthyridine-7-sulfonamido)-butanoic acid
Dab(SN53) (S)-2-amino-4-(1,2,3,4-tetrahydro-1,5-naphthyridine-1-sulfonamido)-butanoic acid
Dab(SN54) (S)-2-amino-4-(5,6,7,8-tetrahydroimidazo[1,2-α]pyrazine-7-sulfonamido)-butanoic acid
Dab(SN55) (S)-4-(4-(1H-imidazol-1-yl)piperidin-1-ylsulfonylamino)-2-aminobutanoic acid
Dab(SN56) (S)-4-(4-(1H-imidazol-2-yppiperidin-1-ylsulfonylamino)-2-aminobutanoic acid
Dab(SN57) (S)-4-(1,4-oxazepan-4-ylsulfonylamino)-2-aminobutanoic acid
Dab(SN58) (S)-2-amino-4-(4-methyl-1,4-diazepan-1-ylsulfonylamino)butanoic acid
Dab(SN59) (2S)-2-amino-4-(N-(2,3-dihydro-1H-inden-1-ylamino)sulfamoyl)-butanoic acid
Dab(SN60) (2S)-2-amino-4-(N-(1,2,3,4-tetrahydronaphthalen-1-yl)sulfamoylamino)-butanoic acid
Dab(SN61) (S)-2-amino-4-(4-(2-hydroxyethyl)piperazine-1-sulfonamido)butanoic acid
Dab(UN1) (S)-2-amino-4-ureidobutanoic acid
Dab(UN2) (S)-2-amino-4-(3-methylureido)butanoic acid
Dab(UN3) (S)-2-amino-4-(3,3-dimethylureido)butanoic acid
Dab(UN4) (S)-2-amino-4-(3-isopropylureido)butanoic acid
Dab(UN5) (S)-2-amino-4-(3-cyclopropylureido)butanoic acid
Dab(UN6) (S)-2-amino-4-(3-isobutylureido)butanoic acid
Dab(UN7) (S)-2-amino-4-(3-(2,2,2-trifluoroethyl)ureido) butanoic acid
Dab(UN8) (S)-2-amino-4-(azetidine-1-carboxamido)butanoic acid
Dab(UN9) (S)-2-amino-4-(pyrrolidine-1-carboxamido)butanoic acid
Dab(UN10) (S)-2-amino-4-(piperidine-1-carboxamido)butanoic acid
Dab(UN11) (S)-2-amino-4-(morpholine-4-carboxamido)butanoic acid
Dab(UN12) (S)-2-amino-4-(piperazine-1-carboxamido)butanoic acid
Dab(UN13) (S)-2-amino-4-(4-methylpiperazine-1-carboxamido)butanoic acid
Dab(UN14) (S)-4-(4-acetylpiperazine-1-carboxamido)-2-aminobutanoic acid
Dab(UN15) (S)-2-amino-4-(4-hydroxypiperidine-1-carboxamido)butanoic acid
Dab(UN16) (2S)-2-amino-4-(2-methyl-1-oxo-2,6-diazaspiro[4.5]decane-6-carboxamido)butanoic acid
Dab(UN17) (S)-2-amino-4-(4-(dimethylamino)piperidine-1-carboxamido)butanoic acid
Dab(UN18) (2S)-2-amino-4-(7-methyl-1,7-diazaspiro[4.4]nonane-1-carboxamido)-butanoic acid
Dab(UN19) (S)-2-amino-4-(2,2-dimethylpyrrolidine-1-carboxamido)butanoic acid
Dab(UN20) (S)-2-amino-4-(3-cyclopentylureido)butanoic acid
Dab(UN21) (S)-2-amino-4-(3-cyclohexylureido)butanoic acid
Dab(UN22) (S)-2-amino-4-(3-(tetrahydro-2H-pyran-4-yl)ureido)butanoic acid
Dab(UN23) (S)-2-amino-4-(3-(2-hydroxyethyl)ureido)butanoic acid
Dab(UN24) (S)-2-amino-4-(3-(2-methoxyethyl)ureido)butanoic acid
Dab(UN25) (S)-2-amino-4-(3-(2-aminoethyl)ureido)butanoic acid
Dab(UN26) (S)-2-amino-4-(3-(2-(dimethylamino)ethyl)ureido)butanoic acid
Dab(UN27) (S)-2-amino-4-(3-(2-methoxyethyl)-N-methylureido)butanoic acid
Dab(UN28) (S)-2-amino-4-(3-(2-(dimethylamino)ethyl)-N-methylureido)butanoic acid
Dab(UN29) (S)-2-amino-4-(3-(3-aminopropyl)ureido)butanoic acid
Dab(UN30) (S)-2-amino-4-(3-(3-(dimethylamino)propyl)ureido)butanoic acid
Dab(UN31) (S)-2-amino-4-(3-(3-(dimethylamino)propyl)-N-methylureido)butanoic acid
Dab(UN32) (S)-4-(3-(2-acetamidoethyl)ureido)-2-aminobutanoic acid
Dab(UN33) (S)-2-amino-4-(3-(2-(pyrrolidin-1-yl)ethyl)ureido)butanoic acid
Dab(UN34) (S)-2-amino-4-(3-(2-morpholinoethyl)ureido)butanoic acid
Dab(UN35) (S)-2-amino-4-(3-(3-morpholinopropyl)ureido)butanoic acid
Dab(UN36) (S)-2-amino-4-(3-(1,3-dihydroxypropan-2-yl)ureido)butanoic acid
Dab(UN37) (S)-2-amino-4-(3-(4-hydroxy-3-(hydroxymethyl)butyl)ureido)butanoic acid
Dab(UN38) (S)-2-amino-4-(3-(piperidin-4-ylmethyl)ureido)butanoic acid
Dab(UN39) (S)-2-amino-4-(3-methyl-3-((tetrahydro-2H-pyran-4-yl)methyl)ureido)-butanoic acid
Dab(UN40) (2S)-2-amino-4-(3-methyl-3-(2-(1-methylpyrrolidin-2-yl)ethyl)ureido)-butanoic acid
Dab(UN41) (S)-2-amino-4-(3-(thiazol-2-ylmethyl)ureido)butanoic acid
Dab(UN42) (S)-2-amino-4-(3-((1-methyl-1H-imidazol-4-yl)methypureido)butanoic acid
Dab(UN43) (S)-2-amino-4-(3-benzylureido)butanoic acid
Dab(UN44) (S)-2-amino-4-(3-(4-(methylsulfonyl)benzyl)ureido)butanoic acid
Dab(UN45) (S)-2-amino-4-(3-(pyridin-3-ylmethyl)ureido)butanoic acid
Dab(UN46) (S)-2-amino-4-(3-(4-(trifluoromethyl)benzyl)ureido)butanoic acid
Dab(UN47) (S)-2-amino-4-(3-(2-methoxybenzyl)-3-methylureido)butanoic acid
Dab(UN48) (S)-2-amino-4-(3-((1-methyl-1H-benzo[d]imidazol-2-yOmethyl)ureido)-butanoic acid
Dab(UN49) (S)-2-amino-4-(3-((4-methyl-6-(trifluoromethyl)pyrimidin-2-yl)methyl)-ureido)butanoic acid
Dab(UN50) (S)-4-(3-(2-(1H-indol-2-yl)ethyl)ureido)-2-aminobutanoic acid
Dab(UN51) (S)-2-amino-4-(indoline-1-carboxamido)butanoic acid
Dab(UN52) (S)-2-amino-4-(5,6,7,8-tetrahydro-1,7-naphthyridine-7-carboxamido)-butanoic acid
Dab(UN53) (S)-2-amino-4-(1,2,3,4-tetrahydro-1,5-naphthyridine-1-carboxamido)-butanoic acid
Dab(UN54) (S)-2-amino-4-(5,6,7,8-tetrahydroimidazo[1,2-α]pyrazine-7-carboxamido)-butanoic acid Dab(UN55) (S)-4-(4-(1H-imidazol-1-yl)piperidine-1-carboxamido)-2-aminobutanoic acid
Dab(UN56) (S)-4-(4-(1H-imidazol-2-yl)piperidine-1-carboxamido)-2-aminobutanoic acid
Dab(UN57) (S)-4-(1,4-oxazepane-4-carboxamido)-2-aminobutanoic acid
Dab(UN58) (S)-2-amino-4-(4-methyl-1,4-diazepane-1-carboxamido)butanoic acid
Dab(UN59) (2S)-2-amino-4-(3-(2,3-dihydro-1H-inden-1-yl)ureido)butanoic acid
Dab(UN60) (2S)-2-amino-4-(3-(1,2,3,4-tetrahydronaphthalen-1-yl)ureido)-butanoic acid
Dab(UN61) (S)-2-amino-4-(4-(2-hydroxyethyl)piperazine-1-carboxamido)butanoic acid
Dab(S1) (S)-2-amino-4-(methylsulfonamido)butanoic acid
Dab(S2) (S)-2-amino-4-(ethylsulfonamido)butanoic acid
Dab(S3) (S)-2-amino-4-(1-methylethylsulfonamido)butanoic acid
Dab(S4) (S)-2-amino-4-(cyclopropanesulfonamido)butanoic acid
Dab(S5) (S)-2-amino-4-(2-methylpropylsulfonamido)butanoic acid
Dab(S6) (S)-2-amino-4-(2,2,2-trifluoroethylsulfonamido)butanoic acid
Dab(S7) (S)-2-amino-4-(cyclopentanesulfonamido)butanoic acid
Dab(S8) (S)-2-amino-4-(cyclohexanesulfonamido)butanoic acid
Dab(S9) (S)-2-amino-4-(tetrahydro-2H-pyran-4-sulfonamido)butanoic acid
Dab(S10) (S)-2-amino-4-(phenylsulfonamido)butanoic acid
Dab(S11) (S)-2-amino-4-(4-aminophenylsulfonamido)butanoic acid
Dab(S12) (S)-2-amino-4-(4-(dimethylamino)phenylsulfonamido)butanoic acid
Dab(S13) (S)-2-amino-4-(4-morpholinophenylsulfonamido)butanoic acid
Dab(S14) (S)-2-amino-4-(4-cyanophenylsulfonamido)butanoic acid
Dab(S15) (S)-2-amino-4-(5-cyanopyridine-2-sulfonamido)butanoic acid
Dab(S16) (S)-2-amino-4-(1H-pyrazole-4-sulfonamido)butanoic acid
Dab(S17) (S)-2-amino-4-(1H-1,2,4-triazole-5-sulfonamido)butanoic acid
Dab(S18) (S)-2-amino-4-(1,1-dimethylethylsulfonamido)butanoic acid
Dab(A1) (S)-4-acetamido-2-aminobutanoic acid
Dab(A2) (S)-2-amino-4-propionamidobutanoic acid
Dab(A3) (S)-2-amino-4-isobutyramidobutanoic acid
Dab(A4) (S)-2-amino-4-(cyclopropanecarboxamido)butanoic acid
Dab(A5) (S)-2-amino-4-(3,3,3-trifluoropropanamido)butanoic acid
Dab(A6) (S)-2-amino-4-(4,4,4-trifluorobutanamido)butanoic acid
Dab(A7) (S)-2-amino-4-(3-aminopropanamido)butanoic acid
Dab(A8) (S)-2-amino-4-(4-aminobutanamido)butanoic acid
Dab(A9) (S)-2-amino-4-(5-aminopentanamido)butanoic acid
Dab(A10) (S)-2-amino-4-(3-methoxypropanamido)butanoic acid
Dab(A11) (S)-2-amino-4-(3-(methylamino)propanamido)butanoic acid
Dab(A12) (S)-2-amino-4-(3-(dimethylamino)propanamido)butanoic acid
Dab(A13) (S)-2-amino-4-(3-(phenylamino)propanamido)butanoic acid
Dab(A14) (2S)-2-amino-4-(3-aminobutanamido)butanoic acid
Dab(A15) (S)-2-amino-4-(3-amino-3-methylbutanamido)butanoic acid
Dab(A16) (S)-2-amino-4-(3-(methylsulfonyl)propanamido)butanoic acid
Dab(A17) (S)-2-amino-4-(2-cyclopropylacetamido)butanoic acid
Dab(A18) (2S)-2-amino-4-(2-(pyrrolidin-3-yl)acetamido)butanoic acid
Dab(A19) (2S)-2-amino-4-(2-(pyrrolidin-2-yl)acetamido)butanoic acid
Dab(A20) (S)-2-amino-4-(2-(piperidin-4-yl)acetamido)butanoic acid
Dab(A21) (2S)-2-amino-4-(2-(piperidin-3-yl)acetamido)butanoic acid
Dab(A22) (2S)-2-amino-4-(2-(piperidin-2-yl)acetamido)butanoic acid
Dab(A23) (S)-2-amino-4-(3-(piperidin-1-yl)propanamido)butanoic acid
Dab(A24) (S)-2-amino-4-(3-(piperazin-1-yl)propanamido)butanoic acid
Dab(A25) (S)-2-amino-4-(3-(4-methylpiperazin-1-yl)propanamido)butanoic acid
Dab(A26) (S)-2-amino-4-(3-morpholinopropanamido)butanoic acid
Dab(A27) (S)-2-amino-4-(2-(1-aminocyclohexyl)acetamido)butanoic acid
Dab(A28) (S)-2-amino-4-(2-(4-aminotetrahydro-2H-pyran-4-yl)acetamido)-butanoic acid
Dab(A29) (2S)-2-amino-4-(2,2-dimethyl-1,3-dioxolane-4-carboxamido)butanoic acid
Dab(A30) (S)-2-amino-4-benzamidobutanoic acid
Dab(A31) (S)-2-amino-4-(isonicotinamido)butanoic acid
Dab(A32) (S)-2-amino-4-(nicotinamido)butanoic acid
Dab(A33) (S)-2-amino-4-(picolinamido)butanoic acid
Dab(A34) (S)-2-amino-4-(6-(trifluoromethyl)nicotinamido)butanoic acid
Dab(A35) (S)-2-amino-4-(3-methoxybenzamido)butanoic acid
Dab(A36) (S)-2-amino-4-(3-(difluoromethoxy)benzamido)butanoic acid
Dab(A37) (S)-2-amino-4-(4-(methylsulfonyl)benzamido)butanoic acid
Dab(A38) (S)-2-amino-4-(benzo[d][1,3]dioxole-5-carboxamido)butanoic acid
Dab(A39) (S)-2-amino-4-(2-(pyridin-3-yl)acetamido)butanoic acid
Dab(A40) (S)-2-amino-4-(pyrimidine-4-carboxamido)butanoic acid
Dab(A41) (S)-2-amino-4-(3-cyanobenzamido)butanoic acid
Dab(A42) (S)-2-amino-4-(thiophene-2-carboxamido)butanoic acid
Dab(A43) (S)-2-amino-4-(1-methyl-1H-pyrrole-2-carboxamido)butanoic acid
Dab(A44) (S)-2-amino-4-(thiazole-2-carboxamido)butanoic acid
Dab(A45) (S)-2-amino-4-(thiazole-4-carboxamido)butanoic acid
Dab(A46) (S)-2-amino-4-(1-methyl-1H-imidazole-2-carboxamido)butanoic acid
Dab(A47) (S)-2-amino-4-(1-methyl-1H-imidazole-5-carboxamido)butanoic acid
Dab(A48) (S)-2-amino-4-(1-methyl-1H-indole-2-carboxamido)butanoic acid Dab(A49)  (S)-2-amino-4-(benzo[d]thiazole-2-carboxamido)butanoic acid
Dab(A50) (S)-2-amino-4-(quinoxaline-2-carboxamido)butanoic acid
Dab(A51)  (S)-4-(3-(1H-indol-3-yl)propanamido)-2-aminobutanoic acid
Dab(A52) (S)-2-amino-4-(2-aminothiazole-4-carboxamido)butanoic acid
Dab(A53)  (S)-2-amino-4-(2-(2-aminothiazol-4-yl)acetamido)butanoic acid
Dab(A54) (S)-2-amino-4-(4-guanidinobutanamido)butanoic acid
Dab(A55) (S)-2-amino-4-((1H-imidazol-4-yl)methylamino)butanoic acid
Dab(A56)  (S)-2-amino-4-(3-(1-methyl-1H-imidazol-5-yl)propanamido)butanoic acid
Dab(Suc1)  (S)-2-amino-4-(4-(methylamino)-4-oxobutanamido)butanoic acid
Dab(Suc2)  (S)-2-amino-4-(4-(dimethylamino)-4-oxobutanamido)butanoic acid
Dab(Suc3)  (S)-2-amino-4-(4-morpholino-4-oxobutanamido)butanoic acid
Dab(Suc4) (S)-2-amino-4-(4-oxo-4-(piperazin-1-yl)butanamido)butanoic acid
Dab(Suc5)  (S)-2-amino-4-(4-(4-methylpiperazin-1-yl)-4-oxobutanamido)butanoic acid
Dab(Suc6)  (S)-2-amino-4-(4-(methylsulfonamido)-4-oxobutanamido)butanoic acid
Dab(Suc7)  (S)-2-amino-4-(4-(1,1-dimethylethylsulfonamido)-4-oxobutanamido)-butanoic acid
Dab(Suc8)  (S)-2-amino-4-(4-oxo-4-(phenylsulfonamido)butanamido)butanoic acid
Dab(Suc9)  (S)-2-amino-4-(4-(4-chloropyridine-3-sulfonamido)-4-oxobutanamido)-butanoic acid
Dab(Suc10)  (S)-2-amino-4-(4-(naphthalene-2-sulfonamido)-4-oxobutanamido)-butanoic acid
Asn(Alk1) (S)-2-amino-4-oxo-4-(2,2,2-trifluoroethylamino)butanoic acid
Asn(Alk2)  (S)-2-amino-4-(cyclopentylamino)-4-oxobutanoic acid
Asn(Alk3)  (S)-2-amino-4-(cyclohexylamino)-4-oxobutanoic acid
Asn(Alk4)  (S)-2-amino-4-oxo-4-(tetrahydro-2H-pyran-4-ylamino)butanoic acid
Asn(Alk5)  (S)-2-amino-4-(2-hydroxyethylamino)-4-oxobutanoic acid
Asn(Alk6) (S)-2-amino-4-(2-methoxyethylamino)-4-oxobutanoic acid
Asn(Alk7)  (S)-2-amino-4-(2-aminoethylamino)-4-oxobutanoic acid
Asn(Alk8) (S)-2-amino-4-(2-(dimethylamino)ethylamino)-4-oxobutanoic acid
Asn(Alk9)  (S)-2-amino-4-((2-methoxyethyl)(methyl)amino)-4-oxobutanoic acid
Asn(Alk10) (S)-2-amino-4-((2-(dimethylamino)ethyl)(methyl)amino)-4-oxobutanoic acid
Asn(Alk11)  (S)-2-amino-4-(3-aminopropylamino)-4-oxobutanoic acid
Asn(Alk12)  (S)-2-amino-4-(3-(dimethylamino)propylamino)-4-oxobutanoic acid
Asn(Alk13)  (S)-2-amino-4-((3-(dimethylamino)propyl)(methyl)amino)-4-oxobutanoic acid
Asn(Alk14)  (S)-4-(3-acetamidopropylamino)-2-amino-4-oxobutanoic acid
Asn(Alk15) (S)-2-amino-4-oxo-4-(2-(pyrrolidin-1-yl)ethylamino)butanoic acid
Asn(Alk16)  (S)-2-amino-4-(2-morpholinoethylamino)-4-oxobutanoic acid
Asn(Alk17)  (S)-2-amino-4-(3-morpholinopropylamino)-4-oxobutanoic acid
Asn(Alk18)  (S)-2-amino-4-(1,3-dihydroxypropan-2-ylamino)-4-oxobutanoic acid
Asn(Alk19)  (S)-2-amino-4-(4-hydroxy-3-(hydroxymethyp-butylamino)-4-oxobutanoic acid
Asn(Alk20)  (S)-2-amino-4-oxo-4-(piperidin-4-ylmethylamino)butanoic acid
Asn(Alk21)  (S)-2-amino-4-(methyl((tetrahydro-2H-pyran-4-yl)methyl)amino)-4-oxobutanoic acid
Asn(Alk22)  (2S)-2-amino-4-(methyl(2-(1-methylpyrrolidin-2-yl)ethyl)amino)-4-oxobutanoic acid
Asn(Alk23)  (S)-2-amino-4-oxo-4-(thiazol-2-ylmethylamino)butanoic acid
Asn(Alk24)  (S)-2-amino-4-((1-methyl-1H-imidazol-4-yl)methylamino)-4-oxobutanoic acid
Asn(Alk25)  (S)-2-amino-4-(benzylamino)-4-oxobutanoic acid
Asn(Alk26)  (S)-2-amino-4-(4-(methylsulfonyl)benzylamino)-4-oxobutanoic acid
Asn(Alk27)  (S)-2-amino-4-oxo-4-(pyridin-3-ylmethylamino)butanoic acid
Asn(Alk28)  (S)-2-amino-4-oxo-4-(4-(trifluoromethyl)benzylamino)butanoic acid
Asn(Alk29)  (S)-2-amino-4-(2-methoxybenzylamino)-4-oxobutanoic acid
Asn(Alk30)  (S)-2-amino-4-((1-methyl-1H-benzo[d]imidazol-2-yl)methylamino)-4-oxobutanoic acid
Asn(Alk31)  (S)-2-amino-4(4-methyl-6-(trifluoromethyl)pyrimidin-2-yl)-methylamino)-4-oxobutanoic acid
Asn(Alk32)  (S)-4-(2-(1H-indol-3-yl)ethylamino)-2-amino-4-oxobutanoic acid
Asn(Alk33)  (2S)-2-amino-4-(2,3-dihydro-1H-inden-1-ylamino)-4-oxobutanoic acid
Asn(Alk34)  (2S)-2-amino-4-oxo-4-(1,2,3,4-tetrahydronaphthalen-1-ylamino)-butanoic acid
Asp(cN1) (S)-2-amino-4-(azetidin-1-yl)-4-oxobutanoic acid
Asp(cN2)  (S)-2-amino-4-oxo-4-(pyrrolidin-1-yl)butanoic acid
Asp(cN3)  (S)-2-amino-4-oxo-4-(piperidin-1-yl)butanoic acid
Asp(cN4) (S)-2-amino-4-morpholino-4-oxobutanoic acid
Asp(cN5)  (S)-2-amino-4-oxo-4-(piperazin-1-yl)butanoic acid
Asp(cN6)  (S)-2-amino-4-(4-methylpiperazin-1-yl)-4-oxobutanoic acid
Asp(cN7)  (S)-2-amino-4-(4-hydroxypiperidin-1-yl)-4-oxobutanoic acid
Asp(cN8)  (S)-2-amino-4-(4-(dimethylamino)piperidin-1-yl)-4-oxobutanoic acid
Asp(cN9)  (2S)-2-amino-4-(7-methyl-1,7-diazaspiro[4.4]nonan-1-yl)-4-oxobutanoic acid
Asp(cN10) (S)-2-amino-4-(indolin-1-yl)-4-oxobutanoic acid
Asp(cN11)  (S)-2-amino-4-(5,6-dihydro-1,7-naphthyridin-7(8H)-yl)-4-oxobutanoic acid
Asp(cN12)  (S)-2-amino-4-(3,4-dihydro-1,5-naphthyridin-1(2H)-yl)-4-oxobutanoic acid
Asp(cN13)  (S)-2-amino-4-(5,6-dihydroimidazo[1,2-α]pyrazin-7(8H)-yl)-4-oxobutanoic acid
Asp(cN14)  (S)-4-(4-(1H-imidazol-1-yl)piperidin-1-yl)-2-amino-4-oxobutanoic acid
Asp(cN15)  (S)-4-(4-(1H-imidazol-2-yl)piperidin-1-yl)-2-amino-4-oxobutanoic acid
Asp(cN16)  (S)-2-amino-4-(1,4-oxazepan-4-yl)-4-oxobutanoic acid Asp(cN17) (S)-2-amino-4-(4-methyl-1,4-diazepan-1-yl)-4-oxobutanoic acid
Sap(N1) (R)-2-amino-3-sulfamoylpropanoic acid
Sap(N2) (R)-2-amino-3-(N-methylsulfamoyl)propanoic acid
Sap(N3) (R)-2-amino-3-(N,N-dimethylsulfamoyl)propanoic acid
Sap(N4) (R)-2-amino-3-(N-isopropylsulfamoyl)propanoic acid
Sap(N5) (R)-2-amino-3-(N-cyclopropylsulfamoyl)propanoic acid
Sap(N6) (R)-2-amino-3-(N-isobutylsulfamoyl)propanoic acid
Sap(N7) (R)-2-amino-3-(N-(2,2,2-trifluoroethyl)sulfamoyl)propanoic acid
Sap(N8) (R)-2-amino-3-(azetidin-1-ylsulfonyl)propanoic acid
Sap(N9) (R)-2-amino-3-(pyrrolidin-1-ylsulfonyl)propanoic acid
Sap(N10) (R)-2-amino-3-(piperidin-1-ylsulfonyl)propanoic acid
Sap(N11) (R)-2-amino-3-(morpholinosulfonyl)propanoic acid
Sap(N12) (R)-2-amino-3-(piperazin-1-ylsulfonyl)propanoic acid
Sap(N13) (R)-2-amino-3-(4-methylpiperazin-1-ylsulfonyl)propanoic acid
Sap(N14) (R)-3-(4-acetylpiperazin-1-ylsulfonyl)-2-aminopropanoic acid
Sap(N15) (R)-2-amino-3-(4-hydroxypiperidin-1-ylsulfonyl)propanoic acid
Sap(N16) (2R)-2-amino-3-(2-methyl-1-oxo-2,6-diazaspiro[4.5]decan-6-ylsulfonyl)-propanoic acid
Sap(N17) (R)-2-amino-3-(4-(dimethylamino)piperidin-1-ylsulfonyl)propanoic acid
Sap(N18) (2R)-2-amino-3-(7-methyl-1,7-diazaspiro[4.4]nonan-1-ylsulfonyl)-propanoic acid
Sap(N19) (R)-2-amino-3-(2,2-dimethylpyrrolidin-1-ylsulfonyl)propanoic acid
Sap(N20) (R)-2-amino-3-(N-cyclopentylsulfamoyl)propanoic acid
Sap(N21) (R)-2-amino-3-(N-cyclohexylsulfamoyl)propanoic acid
Sap(N22) (R)-2-amino-3-(N-(tetrahydro-2H-pyran-4-yl)sulfamoyl)propanoic acid
Sap(N23) (R)-2-amino-3-(N-(2-hydroxyethyl)sulfamoyl)propanoic acid
Sap(N24) (R)-2-amino-3-(N-(2-methoxyethyl)sulfamoyl)propanoic acid
Sap(N25) (R)-2-amino-3-(N-(2-aminoethyl)sulfamoyl)propanoic acid
Sap(N26) (R)-2-amino-3-(N-(2-(dimethylamino)ethyl)sulfamoyl)propanoic acid
Sap(N27) (R)-2-amino-3-(N-(2-methoxyethyl)-N-methylsulfamoyl)propanoic acid
Sap(N28) (R)-2-amino-3-(N-(2-(dimethylamino)ethyl)-N-methylsulfamoyl)-propanoic acid
Sap(N29) (R)-2-amino-3-(N-(3-aminopropyl)sulfamoyl)propanoic acid
Sap(N30) (R)-2-amino-3-(N-(3-(dimethylamino)propyl)sulfamoyl)propanoic acid
Sap(N31) (R)-2-amino-3-(N-(3-(dimethylamino)propyl)-N-methylsulfamoyl)-propanoic acid
Sap(N32) (R)-3-(N-(2-acetamidoethyl)sulfamoyl)-2-aminopropanoic acid
Sap(N33) (R)-2-amino-3-(N-(2-(pyrrolidin-1-yl)ethyl)sulfamoyl)propanoic acid
Sap(N34) (R)-2-amino-3-(N-(2-morpholinoethyl)sulfamoyl)propanoic acid
Sap(N35) (R)-2-amino-3-(N-(3-morpholinopropyl)sulfamoyl)propanoic acid
Sap(N36) (R)-2-amino-3-(N-(1,3-dihydroxypropan-2-yl)sulfamoyl)propanoic acid
Sap(N37) (R)-2-amino-3-(N-(4-hydroxy-3-(hydroxymethyl)butyl)sulfamoyl)-propanoic acid
Sap(N38) (R)-2-amino-3-(N-(piperidin-4-ylmethyl)sulfamoyl)propanoic acid
Sap(N39) (R)-2-amino-3-(N-methyl-N-((tetrahydro-2H-pyran-4-yl)methyl)-sulfamoyl)propanoic acid
Sap(N40) (2R)-2-amino-3-(N-methyl-N-(2-(1-methylpyrrolidin-2-yl)ethyl)-sulfamoyl)propanoic acid
Sap(N41) (R)-2-amino-3-(N-(thiazol-2-ylmethyl)sulfamoyl)propanoic acid
Sap(N42) (R)-2-amino-3-(N-((1-methyl-1H-imidazol-4-yO-methyl)sulfamoyl)-propanoic acid
Sap(N43) (R)-2-amino-3-(N-benzylsulfamoyl)propanoic acid
Sap(N44) (R)-2-amino-3-(N-(4-(methylsulfonyl)benzyl)sulfamoyl)propanoic acid
Sap(N45) (R)-2-amino-3-(N-(pyridin-3-ylmethyl)sulfamoyl)propanoic acid
Sap(N46) (R)-2-amino-3-(N-(4-(trifluoromethyl)benzyl)sulfamoyl)propanoic acid
Sap(N47) (R)-2-amino-3-(N-(2-methoxybenzyl)-N-methylsulfamoyl)propanoic acid
Sap(N48) (R)-2-amino-3-(N-((1-methyl-1H-benzo[d]imidazol-2-yOmethyl)-sulfamoyl)propanoic acid
Sap(N49) (R)-2-amino-3-(N-((4-methyl-6-(trifluoromethyl)pyrimidin-2-yl)methyl)-sulfamoyl)propanoic acid
Sap(N50) (R)-3-(N-(2-(1H-indol-2-yl)ethyl)sulfamoyl)-2-aminopropanoic acid
Sap(N51) (R)-2-amino-3-(indolin-1-ylsulfonyl)propanoic acid
Sap(N52) (R)-2-amino-3-(5,6-dihydro-1,7-naphthyridin-7(8H)-ylsulfonyl)-propanoic acid
Sap(N53) (R)-2-amino-3-(3,4-dihydro-1,5-naphthyridin-1(2H)-ylsulfonyl)-propanoic acid
Sap(N54) (R)-2-amino-3-(5,6-dihydroimidazo[1,2-c]pyrazin-7(8H)-ylsulfonyl)-propanoic acid
Sap(N55) (R)-3-(4-(1H-imidazol-1-yl)piperidin-1-ylsulfonyl)-2-aminopropanoic acid
Sap(N56) (R)-3-(4-(1H-imidazol-2-yppiperidin-1-ylsulfonyl)-2-aminopropanoic acid
Sap(N57) (R)-3-(1,4-oxazepan-4-ylsulfonyl)-2-aminopropanoic acid
Sap(N58) (R)-2-amino-3-(4-methyl-1,4-diazepan-1-ylsulfonyl)propanoic acid
Sap(N59) (2R)-2-amino-3-(N-(2,3-dihydro-1H-inden-1-yl)sulfamoyl)propanoic acid
Sap(N60) (2R)-2-amino-3-(N-(1,2,3,4-tetrahydronaphthalen-1-yl)sulfamoyl)-propanoic acid
Sap(N61) (R)-2-amino-3-(4-(2-hydroxyethyppiperazin-1-ylsulfonyppropanoic acid
Dap(SN1) (S)-2-amino-3-(sulfamoylamino)propanoic acid
Dap(SN2) (S)-2-amino-3-(N-methylsulfamoylamino)propanoic acid
Dap(SN3) (S)-2-amino-3-(N,N-dimethylsulfamoylamino)propanoic acid
Dap(SN4) (S)-2-amino-3-(N-isopropylsulfamoylamino)propanoic acid
Dap(SN5) (S)-2-amino-3-(N-cyclopropylsulfamoylamino)propanoic acid
Dap(SN6) (S)-2-amino-3-(N-isobutylsulfamoylamino)propanoic acid Dap(SN7) (S)-2-amino-3-(N-(2,2,2-trifluoroethyl)sulfamoylamino)propanoic acid
Dap(SN8) (S)-2-amino-3-(azetidin-1-ylsulfonylamino)propanoic acid
Dap(SN9) (S)-2-amino-3-(pyrrolidin-1-ylsulfonylamino)propanoic acid
Dap(SN10) (S)-2-amino-3-(piperidin-1-ylsulfonylamino)propanoic acid
Dap(SN11) (S)-2-amino-3-(morpholinosulfonylamino)propanoic acid
Dap(SN12) (S)-2-amino-3-(piperazin-1-ylsulfonylamino)propanoic acid
Dap(SN13) (S)-2-amino-3-(4-methylpiperazin-1-ylsulfonylamino)propanoic acid
Dap(SN14) (S)-3-(4-acetylpiperazin-1-ylsulfonylamino)-2-aminopropanoic acid
Dap(SN15) (S)-2-amino-3-(4-hydroxypiperidin-1-ylsulfonylamino)propanoic acid
Dap(SN16) (2S)-2-amino-3-(2-methyl-1-oxo-2,6-diazaspiro[4.5]decan-6-yl-sulfonylamino)propanoic acid
Dap(SN17) (S)-2-amino-3-(4-(dimethylamino)piperidin-1-ylsulfonylamino)-propanoic acid
Dap(SN18) (2S)-2-amino-3-(7-methyl-1,7-diazaspiro[4.4]nonan-1-ylsulfonylamino)-propanoic acid
Dap(SN19) (S)-2-amino-3-(2,2-dimethylpyrrolidin-1-ylsulfonylamino)propanoic acid
Dap(SN20) (S)-2-amino-3-(N-cyclopentylsulfamoylamino)propanoic acid
Dap(SN21) (S)-2-amino-3-(N-cyclohexylsulfamoylamino)propanoic acid
Dap(SN22) (S)-2-amino-3-(N-(tetrahydro-2H-pyran-4-yl)sulfamoylamino)-propanoic acid
Dap(SN23) (S)-2-amino-3-(N-(2-hydroxyethyl)sulfamoylamino)propanoic acid
Dap(SN24) (S)-2-amino-3-(N-(2-methoxyethyl)sulfamoylamino)propanoic acid
Dap(SN25) (S)-2-amino-3-(N-(2-aminoethyl)sulfamoylamino)propanoic acid
Dap(SN26) (S)-2-amino-3-(N-(2-(dimethylamino)ethyl)sulfamoylamino)propanoic acid
Dap(SN27) (S)-2-amino-3-(N-(2-methoxyethyl)-N-methylsulfamoylamino)-propanoic acid
Dap(SN28) (S)-2-amino-3-(N-(2-(dimethylamino)ethyl)-N-methylsulfamoylamino)-propanoic acid
Dap(SN29) (S)-2-amino-3-(N-(3-aminopropyl)sulfamoylamino)propanoic acid
Dap(SN30) (S)-2-amino-3-(N-(3-(dimethylamino)propyl)sulfamoylamino)-propanoic acid
Dap(SN31) (S)-2-amino-3-(N-(3-(dimethylamino)propyl)-N-methylsulfamoylamino)-propanoic acid
Dap(SN32) (S)-3-(N-(2-acetamidoethyl)sulfamoylamino)-2-aminopropanoic acid
Dap(SN33) (S)-2-amino-3-(N-(2-(pyrrolidin-1-yl)ethyl)sulfamoylamino)propanoic acid
Dap(SN34) (S)-2-amino-3-(N-(2-morpholinoethyl)sulfamoylamino)propanoic acid
Dap(SN35) (S)-2-amino-3-(N-(3-morpholinopropyl)sulfamoylamino)propanoic acid
Dap(SN36) (S)-2-amino-3-(N-(1,3-dihydroxypropan-2-yl)sulfamoylamino)-propanoic acid
Dap(SN37) (S)-2-amino-3-(N-(4-hydroxy-3-(hydroxymethyl)butyl)sulfamoylamino)-propanoic acid
Dap(SN38) (S)-2-amino-3-(N-(piperidin-4-ylmethyl)sulfamoylamino)propanoic acid
Dap(SN39) (S)-2-amino-3-(N-methyl-N-((tetrahydro-2H-pyran-4-yl)methyl)-sulfamoylamino)propanoic acid
Dap(SN40) (2.5)-2-amino-3-(N-methyl-N-(2-(1-methylpyrrolidin-2-yl)ethyl)-sulfamoylamino)propanoic acid
Dap(SN41) (S)-2-amino-3-(N-(thiazol-2-ylmethyl)sulfamoylamino)propanoic acid
Dap(SN42) (S)-2-amino-3-(N-((1-methyl-1H-imidazol-4-yOmethyl)-sulfamoylamino)propanoic acid
Dap(SN43) (S)-2-amino-3-(N-benzylsulfamoylamino)propanoic acid
Dap(SN44) (S)-2-amino-3-(N-(4-(methylsulfonyl)benzyl)sulfamoylamino)-propanoic acid
Dap(SN45) (S)-2-amino-3-(N-(pyridin-3-ylmethyl)sulfamoylamino)propanoic acid
Dap(SN46) (S)-2-amino-3-(N-(4-(trifluoromethyl)benzyl)sulfamoylamino)-propanoic acid
Dap(SN47) (S)-2-amino-3-(N-(2-methoxybenzyl)-N-methylsulfamoylamino)-propanoic acid
Dap(SN48) (S)-2-amino-3-(N-((1-methyl-1H-benzo[d]imidazol-2-yl)methyl)-sulfamoylamino)propanoic acid
Dap(SN49) (S)-2-amino-3-(N-((4-methyl-6-(trifluoromethyl)pyrimidin-2-yOmethyl)-sulfamoylamino)propanoic acid
Dap(SN50) (S)-3-(N-(2-(1H-indol-2-yl)ethyl)sulfamoylamino)-2-aminopropanoic acid
Dap(SN51) (S)-2-amino-3-(indolin-1-ylsulfonylamino)propanoic acid
Dap(SN52) (S)-2-amino-3-(5,6,7,8-tetrahydro-1,7-naphthyridine-7-sulfonamido)-propanoic acid
Dap(SN53) (S)-2-amino-3-(1,2,3,4-tetrahydro-1,5-naphthyridine-1-sulfonamido)-propanoic acid
Dap(SN54) (S)-2-amino-3-(5,6,7,8-tetrahydroimidazo[1,2-a]pyrazine-7-sulfonamido)-propanoic acid
Dap(SN55) (S)-3-(4-(1H-imidazol-1-yl)piperidin-1-ylsulfonylamino)-2-amino-propanoic acid
Dap(SN56) (S)-3-(4-(1H-imidazol-2-yl)piperidin-1-ylsulfonylamino)-2-amino-propanoic acid
Dap(SN57) (S)-3-(1,4-oxazepan-4-ylsulfonylamino)-2-aminopropanoic acid
Dap(SN58) (S)-2-amino-3-(4-methyl-1,4-diazepan-1-ylsulfonylamino)propanoic acid
Dap(SN59) (2S)-2-amino-3-(N-(2,3-dihydro-1H-inden-1-ylamino)sulfamoyl)-propanoic acid
Dap(SN60) (2S)-2-amino-3-(N-(1,2,3,4-tetrahydronaphthalen-1-yl)sulfamoylamino)-propanoic acid
Dap(SN61) (S)-2-amino-3-(4-(2-hydroxyethyl)piperazine-1-sulfonamido)propanoic acid
Dap(UN1) (S)-2-amino-3-ureidopropanoic acid
Dap(UN2) (S)-2-amino-3-(3-methylureido)propanoic acid
Dap(UN3) (S)-2-amino-3-(3,3-dimethylureido)propanoic acid
Dap(UN4) (S)-2-amino-3-(3-isopropylureido)propanoic acid
Dap(UN5) (S)-2-amino-3-(3-cyclopropylureido)propanoic acid
Dap(UN6) (S)-2-amino-3-(3-isobutylureido)propanoic acid
Dap(UN7) (S)-2-amino-3-(3-(2,2,2-trifluoroethyl)ureido)propanoic acid
Dap(UN8) (S)-2-amino-3-(azetidine-1-carboxamido)propanoic acid
Dap(UN9) (S)-2-amino-3-(pyrrolidine-1-carboxamido)propanoic acid
Dap(UN10) (S)-2-amino-3-(piperidine-1-carboxamido)propanoic acid
Dap(UN11) (S)-2-amino-3-(morpholine-4-carboxamido)propanoic acid
Dap(UN12) (S)-2-amino-3-(piperazine-1-carboxamido)propanoic acid Dap(UN13) (S)-2-amino-3-(4-methylpiperazine-1-carboxamido)propanoic acid
Dap(UN14) (S)-3-(4-acetylpiperazine-1-carboxamido)-2-aminopropanoic acid
Dap(UN15) (S)-2-amino-3-(4-hydroxypiperidine-1-carboxamido)propanoic acid
Dap(UN16) (2S)-2-amino-3-(2-methyl-1-oxo-2,6-diazaspiro[4.5]decane-6-carboxamido)propanoic acid
Dap(UN17) (S)-2-amino-3-(4-(dimethylamino)piperidine-1-carboxamido)-propanoic acid
Dap(UN18) (2S)-2-amino-3-(7-methyl-1,7-diazaspiro[4.4]nonane-1-carboxamido)-propanoic acid
Dap(UN19) (S)-2-amino-3-(2,2-dimethylpyrrolidine-1-carboxamido)propanoic acid
Dap(UN20) (S)-2-amino-3-(3-cyclopentylureido)propanoic acid
Dap(UN21) (S)-2-amino-3-(3-cyclohexylureido)propanoic acid
Dap(UN22) (S)-2-amino-3-(3-(tetrahydro-2H-pyran-4-yl)ureido)propanoic acid
Dap(UN23) (S)-2-amino-3-(3-(2-hydroxyethyl)ureido)propanoic acid
Dap(UN24) (S)-2-amino-3-(3-(2-methoxyethyl)ureido)propanoic acid
Dap(UN25) (S)-2-amino-3-(3-(2-aminoethyl)ureido)propanoic acid
Dap(UN26) (S)-2-amino-3-(3-(2-(dimethylamino)ethyl)ureido)propanoic acid
Dap(UN27) (S)-2-amino-3-(3-(2-methoxyethyl)-3-methylureido)propanoic acid
Dap(UN28) (S)-2-amino-3-(3-(2-(dimethylamino)ethyl)-3-methylureido)propanoic acid
Dap(UN29) (S)-2-amino-3-(3-(3-aminopropyl)ureido)propanoic acid
Dap(UN30) (S)-2-amino-3-(3-(3-(dimethylamino)propyl)ureido)propanoic acid
Dap(UN31) (S)-2-amino-3-(3-(3-(dimethylamino)propyl)-3-methylureido)-propanoic acid
Dap(UN32) (S)-3-(3-(2-acetamidoethyl)ureido)-2-aminopropanoic acid
Dap(UN33) (S)-2-amino-3-(3-(2-(pyrrolidin-1-yl)ethyl)ureido)propanoic acid
Dap(UN34) (S)-2-amino-3-(3-(2-morpholinoethyl)ureido)propanoic acid
Dap(UN35) (S)-2-amino-3-(3-(3-morpholinopropyl)ureido)propanoic acid
Dap(UN36) (S)-2-amino-3-(3-(1,3-dihydroxypropan-2-yl)ureido)propanoic acid
Dap(UN37) (S)-2-amino-3-(3-(4-hydroxy-3-(hydroxymethyl)butyl)ureido)-propanoic acid
Dap(UN38) (S)-2-amino-3-(3-(piperidin-4-ylmethyl)ureido)propanoic acid
Dap(UN39) (S)-2-amino-3-(3-methyl-3-((tetrahydro-2H-pyran-4-Amethyl)ureido)-propanoic acid
Dap(UN40) (2S)-2-amino-3-(3-methyl-3-(2-(1-methylpyrrolidin-2-yl)ethyl)ureido)-propanoic acid
Dap(UN41) (S)-2-amino-3-(3-(thiazol-2-ylmethyl)ureido)propanoic acid
Dap(UN42) (S)-2-amino-3-(3-((1-methyl-1H-imidazol-4-yl)methyl)ureido)-propanoic acid
Dap(UN43) (S)-2-amino-3-(3-benzylureido)propanoic acid
Dap(UN44) (S)-2-amino-3-(3-(4-(methylsulfonyl)benzyl)ureido)propanoic acid
Dap(UN45) (S)-2-amino-3-(3-(pyridin-3-ylmethyl)ureido)propanoic acid
Dap(UN46) (S)-2-amino-3-(3-(4-(trifluoromethyl)benzyl)ureido)propanoic acid
Dap(UN47) (S)-2-amino-3-(3-(2-methoxybenzyl)-3-methylureido)propanoic acid
Dap(UN48) (S)-2-amino-3-(3-((1-methyl-1H-benzo[c]imidazol-2-yOmethypureido)-propanoic acid
Dap(UN49) (S)-2-amino-3-(3-((4-methyl-6-(trifluoromethyl)pyrimidin-2-yOmethyl)-ureido)propanoic acid
Dap(UN50) (S)-3-(3-(2-(1H-indol-2-yl)ethyl)ureido)-2-aminopropanoic acid
Dap(UN51) (S)-2-amino-3-(indoline-1-carboxamido)propanoic acid
Dap(UN52) (S)-2-amino-3-(5,6,7,8-tetrahydro-1,7-naphthyridine-7-carboxamido)-propanoic acid
Dap(UN53) (S)-2-amino-3-(1,2,3,4-tetrahydro-1,5-naphthyridine-1-carboxamido)-propanoic acid
Dap(UN54) (S)-2-amino-3-(5,6,7,8-tetrahydroimidazo[1,2-a]pyrazine-7-carboxamido)-propanoic acid
Dap(UN55) (S)-3-(4-(1H-imidazol-1-yl)piperidine-1-carboxamido)-2-ami nopropanoic acid
Dap(UN56) (S)-3-(4-(1H-imidazol-2-yl)piperidine-1-carboxamido)-2-aminopropanoic acid
Dap(UN57) (S)-3-(1,4-oxazepane-4-carboxamido)-2-aminopropanoic acid
Dap(UN58) (S)-2-amino-3-(4-methyl-1,4-diazepane-1-carboxamido)propanoic acid
Dap(UN59) (2S)-2-amino-3-(3-(2,3-dihydro-1H-inden-1-yl)ureido)propanoic acid
Dap(UN60) (2S)-2-amino-3-(3-(1,2,3,4-tetrahydronaphthalen-1-yl)ureido)-propanoic acid
Dap(UN61) (S)-2-amino-3-(4-(2-hydroxyethyl)piperazine-1-carboxamido)-propanoic acid
Dap(S1) (S)-2-amino-3-(methylsulfonamido)propanoic acid
Dap(S2) (S)-2-amino-3-(ethylsulfonamido)propanoic acid
Dap(S3) (S)-2-amino-3-(1-methylethylsulfonamido)propanoic acid
Dap(S4) (S)-2-amino-3-(cyclopropanesulfonamido)propanoic acid
Dap(S5) (S)-2-amino-3-(2-methylpropylsulfonamido)propanoic acid
Dap(S6) (S)-2-amino-3-(2,2,2-trifluoroethylsulfonamido)propanoic acid
Dap(S7) (S)-2-amino-3-(cyclopentanesulfonamido)propanoic acid
Dap(S8) (S)-2-amino-3-(cyclohexanesulfonamido)propanoic acid
Dap(S9) (S)-2-amino-3-(tetrahydro-2H-pyran-4-sulfonamido)propanoic acid
Dap(S10) (S)-2-amino-3-(phenylsulfonamido)propanoic acid
Dap(S11) (S)-2-amino-3-(4-aminophenylsulfonamido)propanoic acid
Dap(S12) (S)-2-amino-3-(4-(dimethylamino)phenylsulfonamido)propanoic acid
Dap(S13) (S)-2-amino-3-(4-morpholinophenylsulfonamido)propanoic acid
Dap(S14) (S)-2-amino-3-(4-cyanophenylsulfonamido)propanoic acid
Dap(S15) (S)-2-amino-3-(5-cyanopyridine-2-sulfonamido)propanoic acid
Dap(S16) (S)-2-amino-3-(1H-pyrazole-4-sulfonamido)propanoic acid
Dap(S17) (S)-2-amino-3-(1H-1,2,4-triazole-5-sulfonamido)propanoic acid
Dap(S18) (S)-2-amino-3-(1,1-dimethylethylsulfonamido)propanoic acid
Dap(A1) (S)-3-acetamido-2-aminopropanoic acid
Dap(A2) (S)-2-amino-3-propionamidopropanoic acid
Dap(A3) (S)-2-amino-3-isobutyramidopropanoic acid Dap(A4) (S)-2-amino-3-(cyclopropanecarboxamido)propanoic acid
Dap(A5) (S)-2-amino-3-(3,3,3-trifluoropropanamido)propanoic acid
Dap(A6) (S)-2-amino-3-(4,4,4-trifluorobutanamido)propanoic acid
Dap(A7) (S)-2-amino-3-(3-aminopropanamido)propanoic acid
Dap(A8) (S)-2-amino-3-(4-aminobutanamido)propanoic acid
Dap(A9) (S)-2-amino-3-(5-aminopentanamido)propanoic acid
Dap(A10) (S)-2-amino-3-(3-methoxypropanamido)propanoic acid
Dap(A11) (S)-2-amino-3-(3-(methylamino)propanamido)propanoic acid
Dap(A12) (S)-2-amino-3-(3-(dimethylamino)propanamido)propanoic acid
Dap(A13) (S)-2-amino-3-(3-(phenylamino)prbpanamido)propanoic acid
Dap(A14) (2S)-2-amino-3-(3-aminobutanamido)propanoic acid
Dap(A15) (S)-2-amino-3-(3-amino-3-methylbutanamido)propanoic acid
Dap(A16) (S)-2-amino-3-(3-(methylsulfonyl)propanamido)propanoic acid
Dap(A17) (S)-2-amino-3-(2-cyclopropylacetamido)propanoic acid
Dap(A18) (2S)-2-amino-3-(2-(pyrrolidin-3-yl)acetamido)propanoic acid
Dap(A19) (2S)-2-amino-3-(2-(pyrrolidin-2-yl)acetamido)propanoic acid
Dap(A20) (S)-2-amino-3-(2-(piperidin-4-yl)acetamido)propanoic acid
Dap(A21) (2S)-2-amino-3-(2-(piperidin-3-yl)acetamido)propanoic acid
Dap(A22) (2S)-2-amino-3-(2-(piperidin-2-yl)acetamido)propanoic acid
Dap(A23) (S)-2-amino-3-(3-(piperidin-1-yl)propanamido)propanoic acid
Dap(A24) (S)-2-amino-3-(3-(piperazin-1-yl)propanamido)propanoic acid
Dap(A25) (S)-2-amino-3-(3-(4-methylpiperazin-1-yl)propanamido)propanoic acid
Dap(A26) (S)-2-amino-3-(3-morpholinopropanamido)propanoic acid
Dap(A27) (S)-2-amino-3-(2-(1-aminocyclohexyl)acetamido)propanoic acid
Dap(A28) (S)-2-amino-3-(2-(4-aminotetrahydro-2H-pyran-4-yl)acetamido)-propanoic acid
Dap(A29) (2S)-2-amino-3-(2,2-dimethyl-1,3-dioxolane-4-carboxamido)-propanoic acid
Dap(A30) (S)-2-amino-3-benzamidopropanoic acid
Dap(A31) (S)-2-amino-3-(isonicotinamido)propanoic acid
Dap(A32) (S)-2-amino-3-(nicotinamido)propanoic acid
Dap(A33) (S)-2-amino-3-(picolinamido)propanoic acid
Dap(A34) (S)-2-amino-3-(6-(trifluoromethyl)nicotinamido)propanoic acid
Dap(A35) (S)-2-amino-3-(3-methoxybenzamido)propanoic acid
Dap(A36) (S)-2-amino-3-(3-(difluoromethoxy)benzamido)propanoic acid
Dap(A37) (S)-2-amino-3-(4-(methylsulfonyl)benzamido)propanoic acid
Dap(A38) (S)-2-amino-3-(benzo[d][1,3]dioxole-5-carboxamido)propanoic acid
Dap(A39) (S)-2-amino-3-(2-(pyridin-3-yl)acetamido)propanoic acid
Dap(A40) (S)-2-amino-3-(pyrimidine-4-carboxamido)propanoic acid
Dap(A41) (S)-2-amino-3-(3-cyanobenzamido)propanoic acid
Dap(A42) (S)-2-amino-3-(thiophene-2-carboxamido)propanoic acid
Dap(A43) (S)-2-amino-3-(1-methyl-1H-pyrrole-2-carboxamido)propanoic acid
Dap(A44) (S)-2-amino-3-(thiazole-2-carboxamido)propanoic acid
Dap(A45) (S)-2-amino-3-(thiazole-4-carboxamido)propanoic acid
Dap(A46) (S)-2-amino-3-(1-methyl-1H-imidazole-2-carboxamido)propanoic acid
Dap(A47) (S)-2-amino-3-(1-methyl-1H-imidazole-5-carboxamido)propanoic acid
Dap(A48) (S)-2-amino-3-(1-methyl-1H-indole-2-carboxamido)propanoic acid
Dap(A49) (S)-2-amino-3-(benzo[d]thiazole-2-carboxamido)propanoic acid
Dap(A50) (S)-2-amino-3-(quinoxaline-2-carboxamido)propanoic acid
Dap(A51) (S)-3-(3-(1H-indol-3-yl)propanamido)-2-aminopropanoic acid
Dap(A52) (S)-2-amino-3-(2-aminothiazole-4-carboxamido)propanoic acid
Dap(A53) (S)-2-amino-3-(2-(2-aminothiazol-4-yp)acetamido)propanoic acid
Dap(A54) (S)-2-amino-3-(4-guanidinobutanamido)propanoic acid
Dap(Suc1) (S)-2-amino-3-(4-(methylamino)-4-oxobutanamido)propanoic acid
Dap(Suc2) (S)-2-amino-3-(4-(dimethylamino)-4-oxobutanamido)propanoic acid
Dap(Suc3) (S)-2-amino-3-(4-morpholino-4-oxobutanamido)propanoic acid
Dap(Suc4) (S)-2-amino-3-(4-oxo-4-(piperazin-1-yl)butanamido)propanoic acid
Dap(Suc5) (S)-2-amino-3-(4-(4-methylpiperazin-1-yl)-4-oxobutanamido)-propanoic acid
Dap(Suc6) (S)-2-amino-3-(4-(methylsulfonamido)-4-oxobutanamido)propanoic acid
Dap(Suc7) (S)-2-amino-3-(4-(1,1-dimethylethylsulfonamido)-4-oxobutanamido)-propanoic acid
Dap(Suc8) (S)-2-amino-3-(4-oxo-4-(phenylsulfonamido)butanamido)propanoic acid
Dap(Suc9) (S)-2-amino-3-(4-(4-chloropyridine-3-sulfonamido)-4-oxobutanamido)-propanoic acid
Dap(Suc10) (S)-2-amino-3-(4-(naphthalene-2-sulfonamido)-4-oxobutanamido)-propanoic acid In a preferred embodiment of the invention the β-hairpin peptidomimetics of general formula (I) are selected from the group consisting of:
cyclo(-Trp-Aib-Trp-Arg-$^D$Pro-Tic-);
cyclo(-Trp-Aib-Trp-Dab-$^D$Pro-Tic-);
cyclo(-Trp-Cyp-Trp-Arg-$^D$Pro-Tic(7OH)—);
cyclo(-Trp-Cyp-Trp-Dab-$^D$Pro-Pro((4S)F)—);
cyclo(-Trp-Cyp-Trp-Arg-DPro-Thz-);
cyclo(-Trp-Cyp-Trp-Dab-$^D$Pro-Thz-);
cyclo(-Trp(5OH)-Cyp-Trp-Gln-$^D$Pro-Thz-);
cyclo(-Trp(5OH)-Cyp-Trp-Arg-$^D$Pro-Tic-);
cyclo(-2NaI-Cyp-Trp-Gln-$^D$Pro-Tic-);
cyclo(-2NaI-Cyp-Trp-Dab-$^D$Pip-Pip-);
cyclo(-Trp(5OH)-Chx-Trp(5OH)-Arg-$^D$Pro-Oic-);
cyclo(-Trp(5OH)-Cyp-Trp(5OH)-Dap-$^D$Pro-Oic-);

cyclo(-Trp-Cyp-Trp-Dab-$^D$Pip-Oic-);
cyclo(-Trp-Cyp-2NaI-Dab-$^D$Pip-Oic-);
cyclo(-Trp-Cyp-2NaI-Gln-$^D$Pro-Oic-);
cyclo(-OctG-Cyp-Trp-Dab-$^D$Pro-Oic-);
cyclo(-Trp-Cyp-Trp-Gln-$^D$Pro-Oic-);
cyclo(-Trp-Chx-Trp-Dab-$^D$Pro-Oic-);
cyclo(-Trp-Ac3c-Trp-Dab-$^D$Pro-Oic-);
cyclo(-Trp-Ac4c-Trp-Dab-$^D$Pro-Oic-);
cyclo(-Trp-4,4-AC-ThioTHP-Trp-Dab-$^D$Pro-Oic-);
cyclo(-Trp-Cyp-Phe(4F)-Dab-$^D$Pro-Oic-);
cyclo(-Trp-Cyp-Tyr(Me)-Dab-$^D$Pro-Oic-);
cyclo(-Trp-Cyp-Ala(2Quin)-Dab-$^D$Pro-Oic-);
cyclo(-Trp-Cyp-Trp-Arg-$^D$Aze-Tic-);
cyclo(-Trp-Cyp-Trp-Dab-$^D$Aze-Tic-);
cyclo(-Cha-Cyp-Trp-Dab-$^D$Pro-Oic-);
cyclo(-Trp-Cyp-Trp-Dab-$^D$Pro-Oic-);
cyclo(-Trp(5OH)-Cyp-Trp-Arg-$^D$Pro-Thz(5,5Me$_2$)-);
cyclo(-Trp-Atc-Trp-Dab-$^D$Pro-Oic-);
cyclo(-Trp-Cyp-Ala(2Furyl)-Dab-$^D$Pro-Oic-);
cyclo(-Trp-Cyp-Phe(4F)-Ser-$^D$Pro-Oic-);
cyclo(-Trp-Cyp-Phe(4Cl)-Ser-$^D$Pro-Oic-);
cyclo(-Trp-Cyp-Phe(4CF$_3$)-Dab-$^D$Pro-Oic-);
cyclo(-Trp-Cyp-DLTrp(7Aza)-Dab-$^D$Pro-Oic-);
cyclo(-Trp-Cyp-Tyr(Ph)-Dab-DPro-Oic-);
cyclo(-Phe(4CF$_3$)—Cyp-Trp-Dab-$^D$Pip-Pro((4R)Ph)-);
cyclo(-Trp-Cyp-Trp-Dab-$^D$Pro-Pro((4R)Bn)-);
cyclo(-Trp-Cyp-Trp-Dab-$^D$Pro-Pro((4R)$_4$BrBn)-);
cyclo(-Trp-Cyp-Trp-Dab-$^D$Pro-Pro((4R)$_3$CNBn)-);
cyclo(-Trp-Cyp-Trp-Dab-$^D$Pro-Pro((4S)$_c$Hex)-);
cyclo(-Trp-Cyp-Trp-Dab-$^D$Pro-Pro(5,5Me$_2$)-);
cyclo(-Trp-Cyp-Phe(4Cl)-Dab-$^D$Pro-Hyp(Bn)-);
cyclo(-Phe(4CN)-Cyp-Phe(4F)-Ser-$^D$Pro-Hyp(Bn)-);
cyclo(-Trp-Cyp-Trp-Dab-$^D$Pro-Hyp(Bn)-);
cyclo(-Trp-Cyp-Trp-Ser-$^D$Pro-Hyp(Bn)-);
cyclo(-Phe(4CN)-Cyp-Trp-Gln-$^D$Pro-Hyp(Bn)-);
cyclo(-Trp(6Cl)-Cyp-Trp-Dab-$^D$Pro-Hyp(Bn)-);
cyclo(-Phe(4CN)-Cyp-Trp-Dab-$^D$Pro-Hyp(Bn)-);
cyclo(-Phe(4CN)-Cyp-Trp-Ser-$^D$Pip-Hyp(Bn)-);
cyclo(-Trp-Cyp-Trp-Dab-$^D$Pro-(4S)-Hyp(Bn)-);
cyclo(-Trp-Cyp-Trp-Dab-$^D$Pro-Hyp(Ph)-);
cyclo(-Trp-Cyp-Trp-Dab-$^D$Pro-Hyp(4CNBn)-);
cyclo(-Phe(4CF$_3$)-Cyp-Trp-Dab-$^D$Pro-Hyp(4BrBn)-);
cyclo(-Phe(4CN)-Cyp-Trp-Ser-$^D$Pro-Hyp(4BrBn)-);
cyclo(-Trp-Cyp-Trp-Dab-$^D$Pro-Hyp(4BrBn)-);
cyclo(-Trp-Cyp-Trp-Dab-$^D$Pro-Hyp(CONHPh)-);
cyclo(-Trp-Cyp-Trp-alloThr-$^D$Pro-Oic-);
cyclo(-Trp-Cyp-Trp-hArg-$^D$Pro-Oic-);
cyclo(-Trp-Cyp-Trp-hCys-$^D$Pro-Oic-);
cyclo(-Trp-Cyp-Trp-Gln(iPr)-$^D$Pro-Oic-);
cyclo(-Trp-Cyp-Trp-hSer(Me)-$^D$Pro-Oic-);
cyclo(-Trp-Cyp-Trp-Lys(Ac)-$^D$Pro-Oic-);
cyclo(-Trp-Cyp-Trp-Lys(Bz)-$^D$Pro-Oic-);
cyclo(-Trp-Cyp-Trp-Lys(Me)-$^D$Pro-Oic-);
cyclo(-Trp-Cyp-Trp-Lys((5R)OH)-$^D$Pro-Oic-);
cyclo(-Trp-Cyp-Trp-Lys(Nic)-DPro-Oic-);
cyclo(-Trp-Cyp-Trp-Met(O$_2$)-$^D$Pro-Oic-);
cyclo(-Trp-Cyp-Trp-Ala(Ppz)-$^D$Pro-Oic-);
cyclo(-Trp-Cyp-Trp-Dap(CONH$_2$)-$^D$Pro-Oic-);
cyclo(-Trp-Cyp-Trp-Dab(Dab)-$^D$Pro-Oic-);
cyclo(-Trp-Cyp-Trp-Dab(MEMCO)-$^D$Pro-Oic-);
cyclo(-Trp-Cyp-Trp-Dab(MeO(CH$_2$)$_2$NHCO)-$^D$Pro-Oic-);
cyclo(-Trp-Cyp-Trp-Dap(MeO(CH$_2$)$_2$)-$^D$Pro-Oic-);
cyclo(-Trp-Cyp-Trp-DapaMeO(CH$_2$)$_2$)$_2$)-$^D$Pro-Oic-);
cyclo(-Ph(4COOMe)-Cyp-Trp-Dab-$^D$Pro-Oic-);
cyclo(-Trp-Cyp-Trp-Dab-$^D$Pro-Hyp(3CNBn)-);
cyclo(-Phe(4CN)-Cyp-Trp-Dab-$^D$Pro-Oic-);
cyclo(-Trp-Cyp-Trp-Ser-$^D$Pro-Oic-);
cyclo(-Trp-Cyp-Trp-Ser-$^D$Pip-Oic-);
cyclo(-Trp(6Cl)-Cyp-Trp-Ser-$^D$Pro-Oic-);
cyclo(-Phe(4CN)-Cyp-Trp-Ser-$^D$Pro-Oic-);
cyclo(-Trp-Cyp-Trp-Lys(4Oxa)-$^D$Pro-Oic-);
cyclo(-Trp-Cyp-Trp-Ser(Me)-$^D$Pro-Oic-);
cyclo(-Trp-Cyp-Trp-Thr-$^D$Pro-Oic-);
cyclo(-Bip-Cyp-Trp-Dab-$^D$Pro-Oic-);
cyclo(-hTyr-Cyp-Trp-Dab-$^D$Pro-Oic-);
cyclo(-Bbta-Cyp-Trp-Dab-$^D$Pro-Oic-);
cyclo(-Nle(6OBn)-Cyp-Trp-Dab-$^D$Pro-Oic-);
cyclo(-Tyr(4OHPh)-Cyp-Trp-Dab-$^D$Pro-Oic-);
cyclo(-Tyr(Ph)-Cyp-Trp-Dab-$^D$Pro-Oic-);
cyclo(-Tyr(4MeOCOBn)-Cyp-Trp-Dab-$^D$Pro-Oic-);
cyclo(-Trp-Deg-Trp-Dab-$^D$Pro-Oic-);
cyclo(-Trp-Ac7c-Trp-Dab-$^D$Pro-Oic-);
cyclo(-Trp-Chx(4-oxo)-Trp-Dab-$^D$Pro-Oic-);
cyclo(-Trp-Ac8c-Trp-Dab-$^D$Pro-Oic-);
cyclo(-Trp-Cyp-Trp-Dab((MeO(CH$_2$)$_2$)(Me)NCO)-$^D$Pro-Oic-);
cyclo(-Trp-Cyp-Trp-Dab(morphCO)-DPro-Oic-);
cyclo(-Trp-Cyp-Trp-Dab(MePpzCO)-$^D$Pro-Oic-);
cyclo(-Trp-Cyp-Trp-Dab(MeSO$_2$)-$^D$Pro-Oic-)
cyclo(-Trp-Cyp-Trp-Dab(4Me$_2$NPhSO$_2$)-$^D$Pro-Oic-);
cyclo(-Trp-Cyp-Trp-Dab(Ac)-$^D$Pro-Oic-);
cyclo(-Trp-Cyp-Trp-Dab-$^D$Pro-Hyp-);
cyclo(-Trp-Cyp-Trp-Dap-$^D$Pro-Oic-);
cyclo(-Trp-Cyp-Trp-Dab(SN13)-$^D$Pro-Oic-);
or pharmaceutically acceptable salts thereof.

In a most preferred embodiment of the invention the β-hairpin peptidomimetics of general formula (I) are selected from the group consisting of:
cyclo(-Cha-Cyp-Trp-Dab-$^D$Pro-Oic-);
cyclo(-Trp-Cyp-Trp-Dab-$^D$Pro-Oic-);
cyclo(-Phe(4CF$_3$)-Cyp-Trp-Dab-$^D$Pip-Pro((4R)Ph)-);
cyclo(-Trp-Cyp-Trp-Dab-$^D$Pro-Pro(5,5Me$_2$)-);
cyclo(-Phe(4CN)-Cyp-Trp-Dab-$^D$Pro-Hyp(Bn)-);
cyclo(-Trp-Cyp-Trp-Met(O$_2$)-$^D$Pro-Oic-);
cyclo(-Trp-Cyp-Trp-Dap(CONH$_2$)-$^D$Pro-Oic-);
cyclo(-Phe(4CN)-Cyp-Trp-Dab-$^D$Pro-Oic-);
cyclo(-Trp-Cyp-Trp-Lys(4Oxa)-$^D$Pro-Oic-);
cyclo(-Trp-Cyp-Trp-Dab(MePpzCO)-$^D$Pro-Oic-);
or pharmaceutically acceptable salts thereof.

In an alternatively preferred embodiment of the invention the β-hairpin peptidomimetics of general formula (I) are selected from the group consisting of:
cyclo(-Trp-Cyp-Trp-Dab(A55)-$^D$Pro-Oic-);
cyclo(-Phe(4CF$_3$)-Cyp-Trp-Dab-$^D$Pro-Oic-);
cyclo(-Phe(4CF$_3$)-Cyp-Trp-Dab(A56)-$^D$Pro-Oic-);
cyclo(-Phe(3CF$_3$)-Cyp-Trp-Dab-DPro-Oic-);
cyclo(-Phe(4CF$_3$)-Cyp-Trp-3 Pal-$^D$Pic-Oic-);
or pharmaceutically acceptable salts thereof.

A further embodiment of the invention relates to the preparation of present β-hairpin peptidomimetics by a process which comprises the steps of
(a) coupling an appropriately functionalized solid support with an appropriately N-protected derivative of that amino acid which in the desired end-product is in position T$^1$ or T$^2$ or 1$^{31}$ to P$^4$ as defined above; any functional group which may be present in said N-protected amino acid derivative being likewise appropriately protected;
(b) removing the N-protecting group from the product obtained in step (a);
(c) coupling the product thus obtained with an appropriately N-protected derivative of that amino acid which in the desired end-product is in the position of the next element (T or P), following counterclockwise or clockwise the sequence according to general formula (I) in —COOH to —NH$_2$ orientation; any functional group which may be present in said N-protected amino acid derivative being likewise appropriately protected;

(d) removing the N-protecting group from the product thus obtained;

(e) repeating steps (c) and (d) until all amino acid residues have been introduced;

(f) if desired, selectively deprotecting one or several protected functional group(s) present in the molecule and chemically transforming the reactive group(s) thus liberated;

(g) detaching the product thus obtained from the solid support;

(h) cyclizing the product cleaved from the solid support;

(i) removing any protecting groups present on functional groups of any members of the chain of amino acid residues and, if desired, any protecting group(s) which may in addition be present in the molecule; and (j) if desired, implementing additional chemical transformations of one or more reactive group(s) present in the molecule;

(k) if desired, converting the product thus obtained into a pharmaceutically acceptable salt or converting a pharmaceutically acceptable, or unacceptable, salt thus obtained into the corresponding free compound of formula (I) or into a different, pharmaceutically acceptable salt.

The process of the invention can advantageously be carried out as parallel array synthesis to yield libraries of template-fixed β-hairpin peptidomimetics of the above general formula (I). Such parallel synthesis allows one to obtain arrays of numerous (normally 24 to 192, typically 96) compounds of general formula (I) in high yields and defined purities, minimizing the formation of dimeric and polymeric by-products. The proper choice of the functionalized solid-support (i.e. solid support plus linker mole-cule), templates and site of cyclization play thereby key roles.

The functionalized solid support is conveniently derived from polystyrene crosslinked with, preferably 1-5%, divinylbenzene; polystyrene coated with polyethyleneglycol spacers (Tentagel®); and polyacrylamide resins (see also Obrecht, D.; Villalgordo, J.-M, "Solid-Supported Combinatorial and Parallel Synthesis of Small-Molecular-Weight Compound Libraries", *Tetrahedron Organic Chemistry Series*, Vol. 17, Pergamon, Elsevier Science, 1998).

The solid support is functionalized by means of a linker, i.e. a bifunctional spacer molecule which contains on one end an anchoring group for attachment to the solid support and on the other end a selectively cleavable functional group used for the subsequent chemical transformations and cleavage procedures. For the purposes of the present invention two types of linkers are used:

Type 1 linkers are designed to release the amide group under acidic conditions (Rink H, *Tetrahedron Lett.* 1987, 28, 3783-3790). Linkers of this kind form amides of the carboxyl group of the amino acids; examples of resins functionalized by such linker structures include 4-[(((2,4-dimethoxyphenyl)Fmoc-aminomethyl)phenoxyacetamido)-aminomethyl] PS resin, 4-[(((2,4-dimethoxyphenyl)Fmoc-aminomethyl)phenoxyacet-amido)aminomethyl] PS resin, 4-[(((2,4-dimethoxyphenyl)Fmoc-animomethyl) Phenooxyacetamido)aminomethyl]-4-methylbenzydrylamine PS resin (Rink amide MBHA PS Resin), and 4-[(((2,4-dimethoxyphenyl)Fmoc-aminomethyl)phenoxyacetamido)aminomethyl]-benzhydrylamine PS-resin (Rink amide BHA PS resin). Preferably, the support is derived from polystyrene crosslinked with, most preferably 1-5%, divinylbenzene and functionalized by means of the 4-(((2,4-dimethoxyphenyl)Fmoc-aminomethyl)phenoxy-acetamido) linker.

Type 2 linkers are designed to eventually release the carboxyl group under acidic conditions. Linkers of this kind form acid-labile esters with the carboxyl group of the amino acids, usually acid-labile benzyl, benzhydryl and trityl esters; examples of such linker structures include 2-methoxy-4-hydroxymethylphenoxy (Sasrin® linker), 4-(2,4-dimethoxyphenyl-hydroxymethyl)-phenoxy (Rink linker), 4-(4-hydroxymethyl-3-meth-oxyphenoxy)butyric acid (HMPB linker), trityl and 2-chlorotrityl. Preferably, the support is derived from polystyrene crosslinked with, most preferably 1-5%, divinylbenzene and functionalized by means of the 2-chlorotrityl linker.

When carried out as parallel array syntheses the processes of the invention can be advantageously carried out as described herein below but it will be immediately apparent to those skilled in the art how these procedures will have to be modified in case it is desired to synthesize one single compound of the above formula (I).

A number of reaction vessels (normally 24 to 192, typically 96) equal to the total number of compounds to be synthesized by the parallel method are loaded with 25 to 1000 mg, preferably 100 mg, of the appropriate functionalized solid support which is preferably derived from polystyrene cross-linked with 1 to 3% of divinylbenzene, or from Tentagel resin.

The solvent to be used must be capable of swelling the resin and includes, but is not limited to, dichloromethane (DCM), dimethylformamide (DMF), N-methylpyrrolidone (NMP), dioxane, toluene, tetrahydrofuran (THF), ethanol (EtOH), trifluoroethanol (TFE), isopropylalcohol and the like. Solvent mixtures containing as at least one component a polar solvent (e.g. 20% TFE/DCM, 35% THF/NMP) are beneficial for ensuring high reactivity and solvation of the resin-bound peptide chains (Fields, G. B., Fields, C. G., *J. Am. Chem. Soc.* 1991, 113, 4202-4207).

With the development of various linkers that release the C-terminal carboxylic acid group under mild acidic conditions, not affecting acid-labile groups protecting functional groups in the side chain(s), considerable progresses have been made in the synthesis of protected peptide fragments. The 2-methoxy-4-hydroxybenzylalcohol-derived linker (Sasrin® linker, Mergler et al., *Tetrahedron Lett.* 1988, 29 4005-4008) is cleavable with diluted trifluoroacetic acid (0.5-1% TFA in DCM) and is stable to Fmoc deprotection conditions during the peptide synthesis, Boc/tBu-based additional protecting groups being compatible with this protection scheme. Other linkers which are suitable for the processes of the invention include the super acid labile 4-(2,4-dimethoxyphenyl-hydroxymethyl)-phenoxy linker (Rink linker, Rink, H. *Tetrahedron Lett.* 1987, 28, 3787-3790), where the removal of the peptide requires 10% acetic acid in DCM or 0.2% trifluoroacetic acid in DCM; the 4-(4-hydroxymethyl-3-methoxy-phenoxy)butyric acid-derived linker (HMPB-linker, Flörsheimer & Riniker, *Peptides* 1991,1990 131) which is also cleaved with 1% TFA/DCM in order to yield a peptide fragment containing all acid labile side-chain protective groups; and, in addition, the 2-chlorotritylchloride linker (Barlos et al., *Tetrahedron Lett.* 1989, 30, 3943-3946), which allows the peptide detachment using a mixture of glacial acetic acid/trifluoro-ethanol/DCM (1:2:7) for about 30 min.

Suitable protecting groups for amino acids and, respectively, for their residues are, for example, for the amino group (as is present e.g. also in the side-chain of lysine)
Cbz benzyloxycarbonyl
Boc tert.-butyloxycarbonyl Fmoc 9-fluorenylmethoxycarbonyl
Alloc allyloxycarbonyl
Teoc trimethylsilylethoxycarbonyl
Tcc trichloroethoxycarbonyl
Nps o-nitrophenylsulfonyl
Trt triphenymethyl or trityl
for the carboxyl group (as is present e.g. also in the side-chain of aspartic and glutamic acid) by conversion into esters with the alcohol components
tBu tert.-butyl
Bn benzyl
Me methyl
Ph phenyl
Pac phenacyl allyl
Tse trimethylsilylethyl
Tce trichloroethyl
for the guanidino group (as is present e.g. in the side-chain of arginine)
Pmc 2,2,5,7,8-pentamethylchroman-6-sulfonyl
Ts tosyl (i.e. p-toluenesulfonyl)
Cbz benzyloxycarbonyl
Pbf 2,2,4,6,7-pentamethyldihydrobenzofuran-5-sulfonyl
for the hydroxy group (as is present e.g. in the side-chain of threonine and serine)
tBu tert.-butyl
Bn. benzyl
Trt trityl
and for the mercapto group (as is present e.g. in the side-chain of cysteine)
Acm acetamidomethyl
tBu tert.-butyl
Bn benzyl
Trt trityl
Mtr 4-methoxytrityl.

The 9-fluorenylmethoxycarbonyl-(Fmoc)-protected amino acid derivatives are pre-ferably used as the building blocks for the construction of the template-fixed β-hairpin loop mimetics of formula (I). For the deprotection, i.e. cleaving off of the Fmoc group, 20% piperidine in DMF or 2% DBU/2% piperidine in DMF can be used.

The quantity of the reactant, i.e. of the amino acid derivative, is usually 1 to 20 equivalents based on the milliequivalents per gram (meq/g) loading of the functionalized solid support (typically 0.1 to 2.85 meq/g for polystyrene resins) originally weighed into the reaction tube. Additional equivalents of reactants can be used, if required, to drive the reaction to completion in a reasonable time. The reaction tubes, in combination with the holder block and the manifold, are reinserted into the reservoir block and the apparatus is fastened together. Gas flow through the manifold is initiated to provide a controlled environment, for example, nitrogen, argon, air and the like. The gas flow may also be heated or chilled prior to flow through the manifold. Heating or cooling of the reaction wells is achieved by heating the reaction block or cooling externally with isopropanol/dry ice and the like to bring about the desired synthetic reactions. Agitation is achieved by shaking or magnetic stirring (within the reaction tube). The preferred workstations (without, however, being limited thereto) are Labsource's Combi-chem station and MultiSyn Tech's-Syro synthesizer.

Amide bond formation requires the activation of the a-carboxyl group for the acylation step. If this activation is being carried out by means of the commonly used carbo-diimides, such as dicyclohexylcarbodiimide (DCC, Sheehan & Hess, *J. Am. Chem. Soc.* 1955, 77, 1067-1068) or diisopropylcarbodiimide (DIC, Sarantakis et al *Biochem. Biophys. Res. Commun.* 1976, 73, 336-342), the resulting dicyclohexylurea and diisopropylurea is insoluble and, respectively, soluble in the solvents generally used. In a variation of the carbodiimide method 1-hydroxybenzotriazole (HOBt, König & Geiger, *Chem. Ber* 1970, 103, 788-798) is included as an additive to the coupling mixture. HOBt prevents dehydration, suppresses racemization of the activated amino acids and acts as a catalyst to improve the sluggish coupling reactions. Certain phosphonium reagents have been used as direct coupling reagents, such as benzotriazol-1-yl-oxy-tris-(dimethylamino)-phosphonium hexafluorophosphate (BOP, Castro et al., *Tetrahedron Lett.* 1975, 14, 1219-1222; *Synthesis,* 1976, 751-752), or benzotriazol-1-yl-oxy-tris-pyrrolidino-phosphonium hexafluorophosphate (Py-BOP, Coste et al., *Tetrahedron Lett.* 1990, 31, 205-208), or 2-(1H-benzotriazol-1-yl-)1,1,3,3-tetramethyluronium tetra-fluoroborate (TBTU), or hexafluorophosphate (HBTU, Knorr et al., *Tetrahedron Lett.* 1989, 30, 1927-1930); these phosphonium and uronium reagents are also suitable for in situ formation of HOBt esters with the protected amino acid derivatives. More recently diphenoxyphosphoryl azide (DPPA) or O-(7-aza-benzotriazol-1-yl)-N,N,N',N'-tetramethyluronium tetrafluoroborate (TATU) or O-(7-aza-benzotriazol-1-yl)-N,N,N',N'-tetramethyluronium hexafluorophosphate (HATU)/7-aza-1-hydroxy benzotriazole (HOAt, Carpino et al., *Tetrahedron Lett.* 1994, 35, 2279-2281) have also been used as coupling reagents.

Due to the fact that near-quantitative coupling reactions are essential, it is desirable to have experimental evidence for completion of the reactions. The ninhydrin test (Kaiser et al., *Anal. Biochemistry* 1970, 34, 595), where a positive colorimetric response to an aliquot of resin-bound peptide indicates qualitatively the presence of the primary amine, can easily and quickly be performed after each coupling step. Fmoc chemistry allows the spectrophotometric detection of the Fmoc chromophore when it is released with the base (Meienhofer et al., *Int. J. Peptide Protein Res.* 1979, 13, 35-42).

The resin-bound intermediate within each reaction tube is washed free of excess of retained reagents, of solvents, and of by-products by repetitive exposure to pure solvent(s).

Washing procedures are repeated up to about 30 times (preferably about 5 times), monitoring the efficiency of reagent, solvent, and by-product removal by methods such as TLC, GC, LC-MS or inspection of the washings.

The above described procedure of reacting the resin-bound compound with reagents within the reaction wells followed by removal of excess reagents, by-products, and solvents is repeated with each successive transformation until the final resin-bound fully protected linear peptide has been obtained.

Before this fully protected linear peptide is detached from the solid support, it is possible, if desired, to selectively deprotect one or several protected functional group(s) present in the molecule and to appropriately substitute the reactive group(s) thus liberated. To this effect, the functional group(s) in question must initially be protected by a protecting group which can be selectively removed without affecting the remaining protecting groups present. Alloc (allyloxycarbonyl) is an example for such an amino protecting group which can be selectively removed, e.g. by means of Pd° and phenylsilane in $CH_2Cl_2$, without affecting the remaining protecting groups, such as Fmoc, present in the molecule. The reactive group thus liberated can then be treated with an agent suitable for introducing the desired substituent. Thus, for example, an amino group can be acylated by means of an acylating agent corresponding to the acyl substituent to be introduced.

After detachment of the fully protected linear peptide from the solid support the individual solutions/extracts are then manipulated as needed to isolate the final compounds. Typical manipulations include, but are not limited to, evaporation, concentration, liquid/liquid extraction, acidification, basification, neutralization or additional reactions in solution.

The solutions containing fully protected linear peptide derivatives which have been cleaved off from the solid support and neutralized with a base, are evaporated. Cyclization is then effected in solution using solvents such as DCM, DMF, dioxane, THF and the like. Various coupling reagents which were mentioned earlier as activators for the amide bond formation can be used for the cyclization. The duration of the cyclization is about 6-48 hours, preferably about 16 hours. The progress of the reaction is followed, e.g. by RP-HPLC (Reverse Phase High Performance Liquid Chromatography). Then the solvent is removed by evaporation, the fully protected cyclic peptide derivative is dissolved in a solvent which is not miscible with water, such as DCM, and the solution is extracted with water or a mixture of water-miscible solvents, in order to remove any excess of the coupling reagent.

Finally, the fully protected peptide derivative is treated with 95% TFA, 2.5% $H_2O$, 2.5% TIS or another combination of scavengers for effecting the cleavage of protecting groups. The cleavage reaction time is commonly 30 minutes to 12 hours, preferably about 2.5 hours. The volatiles are evaporated to dryness and the crude peptide is dissolved in 20% AcOH in water and extracted with isopropyl ether or other solvents which are suitable therefore. The aqueous layer is collected and evaporated to dryness, and the fully deprotected cyclic peptide derivative of formula (I) is obtained as end-product.

For some compounds of the present invention according general formula (I) additional synthetic steps are required. These transformations can be applied either on a partially deprotected cyclic or linear peptide, attached or already released from the solid support or on the final deprotected molecule as exemplified below.

Depending on its purity, this peptide derivative can be used directly for biological assays, or it has to be further purified, for example by preparative HPLC.

As mentioned earlier, it is thereafter possible, if desired, to convert a fully deprotected product of formula (I) thus obtained into a pharmaceutically acceptable salt or to convert a pharmaceutically acceptable, or unacceptable, salt thus obtained into the corresponding free compound of formula (I) or into a different, pharmaceutically acceptable, salt. Any of these operations can be carried out by methods well known in the art.

In general the building blocks for the peptidomimetics of the present invention can be synthesized according to the literature methods (example described below), are known to a person skilled in the art or are commercially available. A few additional new syntheses were carried out for this invention and are described in the examples. All other corresponding amino acids have been described either as unprotected or as Boc- or Fmoc-protected racemates, (D)- or (L)-isomers. It will be appreciated that unprotected amino acid building blocks can be easily transformed into the corresponding Fmoc-protected amino acid building blocks required for the present invention by standard protecting group manipulations. Reviews describing general methods for the synthesis of α-amino acids include: R. Duthaler, *Tetrahedron* (Report) 1994, 349, 1540-1650; R. M. Williams, "Synthesis of optically active α-amino acids", *Tetrahedron Organic Chemistry Series, Vol. 7*, J. E. Baldwin, P. D. Magnus (Eds.), Pergamon Press., Oxford 1989. An especially useful method for the synthesis of optically active α-amino acids relevant for this invention includes kinetic resolution using hydrolytic enzymes (M. A. Verhovskaya, I. A. Yamskov, *Russian Chem. Rev.* 1991, 60, 1163-1179; R. M. Williams, "Synthesis of optically active α-amino acids", *Tetrahedron Organic Chemistry Series, Vol. 7*, J. E. Baldwin, P. D. Magnus (Eds.), Pergamon Press., Oxford 1989, Chapter 7, p. 257-279). Kinetic resolution using hydrolytic enzymes involves hydrolysis of amides and nitriles by aminopeptidases or nitrilases, cleavage of N-acyl groups by acylases, and ester hydrolysis by lipases or proteases. It is well documented that certain enzymes will lead specifically to pure (L)-enantiomers whereas others yield the corresponding (D)-enantiomers (e.g.: R. Duthaler, *Tetrahedron Report* 1994, 349, 1540-1650; R. M. Williams, "Synthesis of optically active α-amino acids", *Tetrahedron Organic Chemistry Series*, Vol. 7, J. E. Baldwin, P. D. Magnus (Eds.), Pergamon Press., Oxford 1989). The β-hairpin peptidomimetics of the invention can be used in a wide range of applications in order to antagonize the CCR10 receptor activity leading to the desired therapeutic effect in man or, due to their similar etiology, in other mammals. Especially they can be used as agents for treating and/or preventing diseases or conditions associated with the immune response in the area of inflammation, cutaneous disorders or cancer, such as, but not limited to, psoriasis, atopic dermatitis, contact sensitivity and allergic dermatitis, Stevens-Johnson syndrome, bullous cutaneous diseases, systemic lupus erythematosis, systemic and multiple sclerosis, allergic asthma, arthritis, graft versus host disease, certain melanoma and cutaneous lymphoma, thyroiditis, as well as inflammatory processes of the gastrointestinal tract and the eye.

For use as medicaments the β-hairpin peptidomimetics of the invention can be administered singly, as mixtures of several β-hairpin peptidomimetics of the invention or in combination with other pharmaceutically active agents. The β-hairpin peptidomimetics of the invention may be administered per se or applied as a pharmaceutical preparation, e.g. an appropriate formulation together with carriers, diluents or excipients well known in the art.

Pharmaceutical compositions comprising β-hairpin peptidomimetics of the invention may be manufactured by means of conventional mixing, dissolving, granulating, coated tablet-making, levigating, emulsifying, encapsulating, entrapping or lyophilizing processes. Pharmaceutical compositions may be formulated in conventional manner using one or more physiologically acceptable carriers, diluents, excipients or auxiliaries which facilitate processing of the active β-hairpin peptidomimetics into preparations which can be used pharmaceutically. Proper formulation depends upon the method of administration chosen.

For topical administration the β-hairpin peptidomimetics of the invention may be formulated as solutions, gels, ointments, creams, suspensions, etc. as are well-known in the art.

Systemic formulations include those designed for administration by injection, e.g. subcutaneous, intravenous, intramuscular, intrathecal or intraperitoneal injection, as well as those designed for transdermal, transmucosal, oral or pulmonary administra-tion.

For injections, the β-hairpin peptidomimetics of the invention may be formulated in adequate solutions, preferably in physiologically compatible buffers such as Hink's solution, Ringer's solution, or physiological saline buffer. The solution may contain formulatory agents such as suspending, stabilizing and/or dispersing agents. Alternatively, the β-hairpin peptidomimetics of the invention may be in powder form for combination with a suitable vehicle, e.g., sterile pyrogen-free water, before use.

For transmucosal administration, penetrants appropriate to the barrier to be permeated are used in the formulation as known in the art.

For oral administration, the compounds of the invention can be readily formulated by combining the active β-hairpin peptidomimetics with pharmaceutically acceptable carriers well known in the art. Such carriers enable the β-hairpin peptidomimetics of the invention to be formulated as tablets, pills, dragees, capsules, liquids, gels, syrups, slurries, suspensions etc., for oral ingestion of a patient to be treated. For oral formulations such as, for example, powders, capsules and tablets, suitable excipients include fillers such as sugars, such as lactose, sucrose, mannitol and sorbitol; cellulose preparations such as maize starch, wheat starch, rice starch, potato starch, gelatin, gum tragacanth, methyl cellulose, hydroxypropylmethyl cellulose, sodium carboxy-methylcellulose, and/or polyvinylpyrrolidone (PVP); granulating agents; and binding agents. If desired, desintegrating agents may be added, such as cross-linked polyvinylpyrrolidones, agar, or alginic acid or a salt thereof, such as sodium alginate. If desired, solid dosage forms may be sugar-coated or enteric-coated using standard techniques.

For oral liquid preparations such as, for example, suspensions, elixirs and solutions, suitable carriers, excipients or diluents include water, glycols, oils, alcohols, etc. In addition, flavoring agents, preservatives, coloring agents and the like may be added.

For buccal administration, the composition may take the form of tablets, lozenges, etc. formulated as usual.

For administration by inhalation, the β-hairpin peptidomimetics of the invention are conveniently delivered in form of an aerosol spray from pressurized packs or a nebulizer, with the use of a suitable propellant, e.g. dichlorodifluoromethane, trichloro-fluoromethane, carbon dioxide or another suitable gas. In the case of a pressurized aerosol the dose unit may be determined by providing a valve to deliver a metered amount. Capsules and cartridges of e.g. gelatin for use in an inhaler or insufflator may be formulated containing a powder mix of the β-hairpin peptidomimetics of the invention and a suitable powder base such as lactose or starch.

The compounds may also be formulated in rectal or vaginal compositions such as solutions for enema or suppositories together with appropriate suppository bases such as cocoa butter or other glycerides.

In addition to the formulations described previously, the β-hairpin peptidomimetics of the invention may also be formulated as depot preparations. Such long acting formulations may be administered by implantation (e.g. subcutaneously or intramuscularly) or by intramuscular injection. For the manufacture of such depot preparations the β-hairpin peptidomimetics of the invention may be formulated with suitable polymeric or hydrophobic materials (e.g. as an emulsion in an acceptable oil) or ion exchange resins, or as sparingly soluble salts.

In addition, other pharmaceutical delivery systems may be employed such as liposomes and emulsions well known in the art. Certain organic solvents such as dimethylsulfoxide also may be employed. Additionally, the (β-hairpin peptidomimetics of the invention may be delivered using a sustained-release system, such as semipermeable matrices of solid polymers containing the therapeutic agent. Various sustained-release materials have been established and are well known by those skilled in the art. Sustained-release capsules may, depending on their chemical nature, release the compounds for a few weeks up to over 3 years. Depending on the chemical nature and the biological stability of the therapeutic agent, additional strategies for protein stabilization may be employed.

As the β-hairpin peptidomimetics of the invention may contain charged residues, they may be included in any of the above-described formulations as such or as pharma-ceutically acceptable salts. Pharmaceutically acceptable salts tend to be more soluble in aqueous and other protic solvents than are the corresponding free base forms.

In addition, the compounds of the present invention and their pharmaceutical acceptable salts may be used per se or in any appropriate formulation in morphological different solid state forms, which may or may not contain different amounts of solvent, e.g. hydrate remaining from the crystallization process.

The β-hairpin peptidomimetics of the invention, or compositions thereof, will generally be used in an amount effective to achieve the intended purpose. It is to be understood that the amount used will depend on a particular application.

For the use of treating or preventing diseases or disorders with an etiology comprising, or associated with, an increased activity of the CCR10 receptor and its ligands (e.g. CCL27 or CCL28), the β-hairpin peptidomimetics of the invention or compositions thereof, are administered or applied in a therapeutically effective amount. Determi-nation of a therapeutically effective amount is well within the capacities of those skilled in the art, especially in view of the detailed disclosure provided herein.

The effective dosage of the active ingredients employed may vary depending on the particular compound or pharmaceutical preparation employed, the mode of administration and the severity and type of the condition treated. Thus, the dosage regimen is selected in accordance with factors including the route of administration and the clearance pathway, e.g. the renal and hepatic function of the patient. A physician, clinician or veterinarian skilled in the art can readily determine and prescribe the amount of the single active ingredients required to prevent, ameliorate or arrest the progress of the condition or disease. Optimal precision in achieving concentration of active ingredients without toxicity requires a regimen based on the kinetics of the active ingredients' availability to the target sites. This involves a consideration of the distribution, equilibrium, and elimination of the active ingredients.

In cases of local administration or selective uptake, the effective local concentration of the β-hairpin peptidomimetics of the invention may not be related to plasma concentration. One having the skills in the art will be able to optimize therapeutically effective local dosages without undue experimentation.

The invention will now be further described in the Examples below, which are intended as an illustration only and not to be construed as limiting the scope of the invention in any way.

The following abbreviations are used in these Examples:
Boc tert-Butyloxycarbonyl;
DCHA Dicyclohexylamine;
DEAD Diethyl azodicarboxylate;
DIPEA Diisopropylethylamine;
Fmoc Fluorenylmethyloxycarbonyl;
HATU O-(7-Aza-benzotriazole-1-yl)-N,N,N',N'-tetramethyluronoium hexafluorophosphate.
HBTU O-(Benzotriazol-1-yl)-N,N,N',N'-tetramethyluronium hexafluorophosphate;
HCTU O-(6-Chlorobenzotriazol-1-yl)-N,N,N',N'-tetramethyluronium hexafluorophosphate PyBop® (Benzotriazol-1-yloxy)tripyrrolidinophosphonium hexafluorophosphate;
TIS Triisopropylsilane;
TPP Triphenylphosphine;
rt Room temperature

EXAMPLES

1. Peptide Synthesis
1.1 General synthetic procedures

Two general methods, Method A and Method B, for the synthesis of the peptide-mimetics of the present invention are exemplified here. This is to demonstrate the principal concept and does not limit or restrict the present invention in any way. A person skilled in the art is easily able to modify these procedures, especially, but not limited to, choosing a different starting position within the ring system, to still achieve the preparation of the claimed cyclic peptidomimetic compounds of the present invention.

Coupling of the First Protected Amino Acid Residue to the Resin
Method A:

0.5 g of 2-chlorotritylchloride resin (Barlos et al. *Tetrahedron Lett.* 1989, 30, 3943-3946) (1.4 mmol/g, 0.7 mmol) was filled into a dried flask. The resin was suspended in $CH_2Cl_2$ (2.5 ml) and allowed to swell at room temperature for 30 min. The resin was treated with 0.43 mmol (0.6 eq) of the first suitably protected amino acid residue or building block (see below) and 488 µl (4 eq) of diisopropylethylamine (DIPEA) in $CH_2Cl_2$ (2.5 ml) and the mixture was shaken at rt for 4 hours. The resin was washed with $CH_2Cl_2$ (1×), DMF (1×), $CH_2Cl_2$ (1×), DMF(1×) and $CH_2Cl_2$ (2×). The resin was shaken in 30 ml $CH_2Cl_2$/MeOH/DIPEA (17:2:1) for 30 min; then washed in the following order with $CH_2Cl_2$(1×), DMF (1×), $CH_2Cl_2$ (1×), MeOH (1×), $CH_2Cl_2$ (1×), MeOH (1×), $CH_2Cl_2$ (2×), $Et_2O$ (2×) and dried under vacuum for 6 hours.
Method B:

In a dried flask, 2-chlorotritylchloride resin (loading: 1.4 mmol/g) was swollen in dry $CH_2Cl_2$ for 30 min (7 ml $CH_2Cl_2$ per g resin). A solution of 0.8 eq of Fmoc-AA-OH and 6 eq of DIPEA in dry $CH_2Cl_2$/DMF (4/1) (10 ml per g resin) was added. After shaking for 2-4 h at rt the resin was filtered and washed successively with $CH_2Cl_2$, DMF, $CH_2Cl_2$, DMF and $CH_2Cl_2$. Then a solution of dry $CH_2Cl_2$/MeOH/DIPEA (17:2:1) was added (10 ml per g resin). After shaking for 3×30 min the resin was filtered in a pre-weighed sinter funnel and washed successively with $CH_2Cl_2$, DMF, $CH_2Cl_2$, MeOH, $CH_2Cl_2$, MeOH, $CH_2Cl_2$ (2×) and $Et_2O$ (2×). The resin was dried under high vacuum overnight. The final mass of resin was calculated before the qualitative control.

The following preloaded resins were prepared: Fmoc-Tic-2-chlorotrityl resin, Fmoc-Oic-2-chlorotrityl resin, Fmoc-$^D$Pro-2-chlorotrityl resin, Fmoc-Arg-2-chlorotrityl resin, Fmoc-$^D$Aze-2-chlorotrityl resin, Fmoc-Trp-2-chlorotrityl resin, Fmoc-Hyp-2-chlorotritylresin, Fmoc-Hyp(Bn)-2-chlorotrityl resin, Fmoc-(4S)-Hyp(Bn)-2-chlorotrityl resin, Hyp(4BrBn)-2-chlorotrityl resin, Fmoc-Dab-2-chlorotrityl resin, Fmoc-Thz-2-chlorotrityl resin, Fmoc-Pip-2-chlorotrityl resin, Fmoc-Phe(4CN)-2-chlorotrityl resin, Fmoc-Pro((4R)Ph)-2-chlorotrityl resin, Fmoc-$^{DL}$Atc-2-chlorotrityl resin, Fmoc-Bbta-2-chlorotrityl resin and Fmoc-$^{DL}$Trp(7Aza)-2-chlorotrityl resin.

Synthesis of the Fully Protected Peptide Fragment

The synthesis was carried out on a Syro-peptide synthesizer (MultiSynTech GmbH) using 24 to 96 reaction vessels. In each vessel were placed approximately 60 mg (Method A) or 80 mg (Method B) of the above resin (weight of the resin before loading). The following reaction cycles were programmed and carried out:
Method A:

| Step | Reagent | Time |
|---|---|---|
| 1 | $CH_2Cl_2$, wash and swell (manual) | 1 × 3 min |
| 2 | DMF, wash and swell | 1 × 60 min |
| 3 | 40% piperidine/DMF | 1 × 5 min and 1 × 15 min |
| 4 | DMF, wash | 5 × 1 min |
| 5 | 5 eq. Fmoc amino acid/DMF + 5 eq. HCTU + 10 eq. DIPEA | 2 × 60 min |
| 6 | DMF, wash | 5 × 1 min |
| 7 | $CH_2Cl_2$, wash (at the end of the synthesis) | 3 × 1 min |

Steps 3 to 6 are repeated to add each amino-acid residue.
Method B:

| Step | Reagent | Time |
|---|---|---|
| 1 | $CH_2Cl_2$, wash and swell (manual) | 1 × 3 min |
| 2 | DMF, wash and swell | 1 × 60 min |
| 3 | 40% piperidine/DMF | 1 × 5 min and 1 × 15 min |
| 4 | DMF, wash | 5 × 1 min |
| 5 | 3.5 eq. Fmoc amino acid/DMF + 3.5 eq. HCTU + 7 eq. DIPEA | 2 × 60 min |
| 6 | DMF, wash | 5 × 1 min |
| 7 | $CH_2Cl_2$, wash (at the end of the synthesis) | 3 × 1 min |

Steps 3 to 6 are repeated to add each amino-acid residue.

After the synthesis of the fully protected peptide fragment had been terminated, the cleavage, cyclization and work up procedures, as described herein below, were used for the preparation of the final compounds.

Cleavage, Backbone Cyclization and Deprotection of the Peptide

After assembly of the linear peptide, the resin was suspended in 1 ml of 1% TFA in $CH_2Cl_2$ (v/v; 0.14 mmol) for 3 minutes and filtered, and the filtrate was neutralized with 1 ml of 20% DIPEA in $CH_2Cl_2$ (v/v; 1.15 mmol). This procedure was repeated four times to ensure completion of the cleavage. The resin was washed three times with 1 ml of $CH_2Cl_2$. The $CH_2Cl_2$ layers containing product were evaporated to dryness.

The fully protected linear peptide was solubilised in 8 ml of dry DMF. Then 2 eq. of HATU in dry DMF (1-2 ml) and 4 eq. of DIPEA in dry DMF (1-2 ml) were added to the peptide, followed by stirring for 16 h. The volatiles were removed by evaporation. The crude cyclic peptide was dissolved in 7 ml of $CH_2Cl_2$ and extracted three times with 4.5 ml 10% acetonitrile in water (v/v). The $CH_2Cl_2$ layers were evaporated to dryness.

To fully deprotect the peptide, 4-7 ml of cleavage cocktail TFA/TIS/$H_2O$ (95:2.5:2.5) was added, and the mixture was kept for 2.5-4 h at room temperature until the reaction was completed. The reaction mixture was evaporated to dryness and the crude peptide was dissolved in 7 ml 20% AcOH in water (v/v) and extracted three times with 4 ml diisopropyl ether. The aqueous layer was collected and evaporated to dryness, and the residue was purified by preparative reverse phase LC-MS.

Purification Procedure (Preparative Reverse Phase LC-MS)

Compounds were purified by reverse phase chromatography using a Vydac 218MS column, 30×150 mm (Cat No. 218MS103015), 10 μm or a Waters XBridge C18, 30×150 mm, 5 μm (Cat No. 186002982).
Mobile phases used were:
A: 0.1% TFA in Water/Acetonitrile 95/5 v/v
B: 0.1% TFA in Acetonitrile Gradient slopes in the preparative runs were adapted each time based on analytical LC-MS analysis of the crude product. As an example, a typical run (purification of Ex. 94) was executed with a flow rate of 35 ml/min running a gradient from 0-2 min. 0% B, 9 min. 55% B to a final of 9.1-12.5 min. 100% B (retention time: 7.38 min in this case).
Detection: MS and UV @ 220 nm Fractions collected were evaporated using a Genevac HT4 evaporator or a Buchi system.

Alternatively for larger amounts the following LC-purification system was used:
Column: Vydac 218MS, 10 μm, 50×150 mm
Mobile phase A: 0.1% TFA in Water
Mobile phase B: 0.1% TFA in Acetonitrile
Flow rate: 150 ml/min
Detection: UV @ 220 nm After lyophilisation the products were obtained typically as white to off-white powders and analysed by HPLC-ESI-MS methods as described below. Analytical data after preparative HPLC purification are shown in Table 1.

1.2 Analytical Methods

Analytical Method A:

Analytical HPLC retention times (RT, in minutes) were determined using a Gemini NX column, 50×2.0 mm, (cod. 00B-4453-B0-Phenomenex) with the following solvents A (H$_2$O+0.1% TFA) and B (CH$_3$CN+0.1% TFA) and the gradient: 0-0.1 min: 97% A, 3% B; 2.7 min: 3% A 97% B; 2.7-3 min: 3% A, 97% B; 3.05-3.3 min: 97% A, 3% B. Flow rate=0.8 ml/min Analytical Method B:

Analytical HPLC retention times (RT, in minutes) were determined using a XBridge C18 column, 50×2.0 mm, (cod. 186003084-Waters) with the following solvents A (H$_2$O+0.1% TFA) and B (CH$_3$CN+0.1% TFA) and the gradient: 0-0.05 min: 97% A, 3% B; 3 min: 3% A 97% B; 3-3.6 min: 3% A, 97% B; 3.6-4.3 min: 97% A, 3% B. Flow rate=0.5 ml/min Analytical Method C:

Analytical HPLC retention times (RT, in minutes) were determined using an HPLC BEH C18 column, 100×2.1 mm, (cod. 186002352-Waters) with the following solvents A (H$_2$O+0.1% TFA) and B (CH$_3$CN+0.1% TFA) and the gradient: 0-0.2 min: 99% A, 1% B; 4 min: 35% A 65% B; 4.05-4.2 min: 5% A, 95% B; 4.2-4.5 min: 99% A, 1% B. Flow rate=0.6 ml/min Analytical method D:

Analytical HPLC retention times (RT, in minutes) were determined using an HPLC Agilent HP1100 Ascentis Express C18 column, 50×3 mm, (cod. 53811-U-Supelco) with the following solvents A (H$_2$O+0.1% TFA) and B (CH$_3$CN+ 0.1% TFA) and the gradient: 0-0.05 min: 97% A, 3% B; 3.35 min: 67% A, 33% B; 3.4-3.65 min: 3% A, 97% B; 3.67-3.7 min: 97% A, 3% B. Flow rate=1.3 ml/min 1.3 Synthesis of Special Building Blocks (2S,4R)-4-(4-cyanobenzyloxy)-1-(tert-butoxycarbonyl)pyrrolidine-2-carboxylic acid

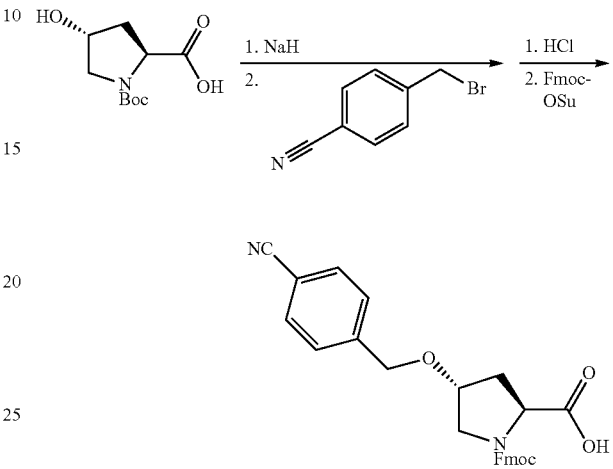

(2S,4R)-1-(tert-Butoxycarbonyl)-4-hydroxypyrrolidine-2-carboxylic acid (1.0 g; 4.3 mmol) in dry THF (5 ml) was carefully combined at 0° C. with a suspension of sodium hydride (60% in paraffin oil, a total of 420 mg; 5.2 mmol; 2.4 eq) in dry THF (9 ml). The mixture was stirred at 0° C. before a solution of 4-(bromomethyl)benzonitrile (1.5 g; 7.8 mmol; 1.8 eq) in dry THF (5 ml) was added in several tranches. Then the mixture was stirred for 45 min at 0° C. and at rt until progress of reaction was ceased. The crude reaction mixture was diluted with 5% aqueous citric acid (50 ml) and extracted twice with ethyl acetate, dried over MgSO$_4$ and concentrated in vacuo to yield 3.2 g crude product.

Flash chromatography on silica gel (CH$_2$Cl$_2$/MeOH 98:2 to 9:1) afforded 580 mg (2,5,4R)-4-(4-cyanobenzyloxy)-1-(tert-butoxycarbonyl)pyrrolidine-2-carboxylic acid.

(2S,4R)-4-(4-Cyanobenzyloxy)-1-(tert-butoxycarbonyl) pyrrolidine-2-carboxylic acid (250 mg, 722 μmol) was dissolved in 4M HCl in dioxane (3 ml, 12 mmol) and the solution was stirred for 1 h at rt. The product was concentrated and washed with Et$_2$O. A clear solution was obtained by addition of 120 mg potassium carbonate (866 μmol) to the residue suspended in 5 ml water and 15 ml acetonitrile. At 0° C. 9-fluorenylmethyl N-succinimidyl carbonate (292 mg, 866 μmol) was added in portions to the solution. The reaction mixture was stirred at rt overnight, diluted in water and treated twice with Et$_2$O (pH around 9-10). The organic layers are washed twice with sat. aq. NaHCO$_3$, which were combined, acidified to pH=1-2 with 5N HCl and re-extracted twice with EtOAc. All combined organic layers were dried (MgSO$_4$) and concentrated to afforded 229 mg (2S,4R)-4-(4-cyanobenzyloxy)-1-W9H-fluoren-9-yl)methoxy)carbonyl) pyrro-lidine-2-carboxylic acid.

(S)-2-(((9H-fluoren-9-yl)methoxy)carbonylamino)-3-(4-(4-(methoxycarbonyl)-benzyloxy)phenyl)propanoic acid

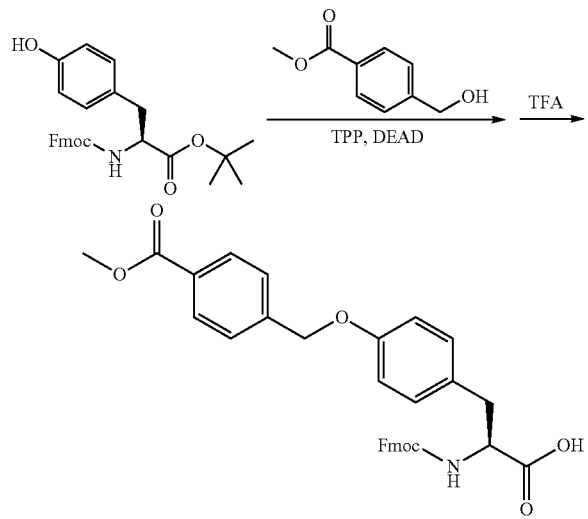

(S)-cert-Butyl 2-(((9H-fluoren-9-yl)methoxy)carbonylamino)-3-(4-hydroxyphenyl)pro-panoate (100 mg, 218 μmol), triphenylphosphine (TPP, 171 mg, 653 μmol) and methyl 4-(hydroxymethyl)benzoate (80 mg, 479 μmol) were combined in 4 ml of dry benzene under nitrogen. A solution of DEAD (40% in toluene, 299 μl, 653 μmol), diluted with 3 ml of dry benzene, was added dropwise over 20 min at 4° C. The mixture was stirred 20 min at 4° C., then at rt overnight. The addition of TPP (57 mg, 218 μmol) and DEAD (100 μl, 218 μmol) was repeated twice to drive the reaction to completion. Volatiles were removed in vacuo and the crude material was purified by flash chromatography on silica gel (hexane/ethylacetate 95/5 to 1/1) afforded 60 mg (S)-2-(Fmoc-amino)-((4-methoxycarbonyl)benzyl)tyrosine tert-butyl ester.

The purified tert-butyl-tyrosine derivative (55 mg, 91 μmol) was dissolved in 600 μl di-chloromethane and cooled to 0° C. 600 μl of TFA were added slowly and the reaction mixture was stirred for 3 h at rt. After the reaction was completed, solvents were removed and co-evaporated once with dichloromethane and 3 times with toluene to yield 46 mg of the final building block (S)-2-(((9H-fluoren-9-yl)methoxy)carbonyl-amino)-3-(4-(4-(methoxycarbonyl)-benzyloxy)phenyl)propanoic acid.

1.4 Synthesis of Peptide Sequences

Examples 1, 2 and 9 are Shown in Table 1.

The peptides were synthesized according general Method A starting with the amino acid (S)-1,2,3,4-tetrahydroisoquinoline-3-carboxylic acid which was grafted to the resin (Fmoc-Tic-2-chlorotrityl resin). The linear peptides were synthesized on the solid support according to the procedure described above in the following sequence: Resin-Tic-$^D$Pro-P$^4$—P$^3$—P$^2$—P$^1$. The products were cleaved from the resin, cyclized, deprotected and purified by preparative reverse phase LC-MS as described above. After lyophilisation the products were obtained as white powders and characterised by HPLC-MS, analytical method A as described above. For analytical data, see Ex. 1, 2, 9 in Table 1.

Examples 3 and 8 are Shown in Table 1.

The peptides were synthesized according general Method A starting with the amino acid L-arginine which was grafted to the resin (Fmoc-Arg-2-chlorotrityl resin). The linear peptides were synthesized on the solid support according to the procedure described above in the following sequence: Resin-Arg-Trp-Cyp-P$^1$-T$^2$-T$^1$. The products were cleaved from the resin, cyclized, deprotected and purified by preparative reverse phase LC-MS as described above.

After lyophilisation the products were obtained as white powders and characterised by HPLC-MS, analytical method A as described above. For analytical data, see Ex. 3, 8 in Table 1.

Examples 4-6 are Shown in Table 1.

The peptides were synthesized according general Method A starting with the amino acid D-proline which was grafted to the resin (Fmoc-$^D$Pro-2-chlorotrityl resin). The linear peptides were synthesized on the solid support according to the procedure described above in the following sequence: Resin-$^D$Pro-P$^4$—P$^3$—P$^2$—P$^1$-T$^2$. The products were cleaved from the resin, cyclized, deprotected and purified by preparative reverse phase LC-MS as described above.

After lyophilisation the products were obtained as white powders and characterised by HPLC-MS, analytical method A as described above. For analytical data, see Ex. 4, 5, 6 in Table 1.

Example 7 is Shown in Table 1.

The peptide was synthesized according general Method A starting with the amino acid (S)-thiazolidine-4-carboxylic acid which was grafted to the resin (Fmoc-Thz-2-chloro-trityl resin). The linear peptide was synthesized on the solid support according to the procedure described above in the following sequence: Resin-Thz-$^D$Pro-Gln-Trp-Cyp-P$^1$. The product was cleaved from the resin, cyclized, deprotected and purified by preparative reverse phase LC-MS as described above.

After lyophilisation the product was obtained as a white powder and characterised by HPLC-MS, analytical method A as described above. For analytical data, see Ex. 7 in Table 1.

Example 10 is Shown in Table 1.

The peptide was synthesized according general Method A starting with the amino acid L-pipecolic acid which was grafted to the resin (Fmoc-Pip-2-chlorotrityl resin). The linear peptide was synthesized on the solid support according to the procedure described above in the following sequence: Resin-Pip-$^D$Pip-Dab-Trp-Cyp-P$^1$. The product was cleaved from the resin, cyclized, deprotected and purified by preparative reverse phase LC-MS as described above.

After lyophilisation the product was obtained as a white powder and characterised by HPLC-MS, analytical method A as described above. For analytical data, see Ex. 10 in Table 1.

Examples 11-24 and 104 are Shown in Table 1.

The peptides were synthesized according general Method A starting with the amino acid (S)-(2S,3aS,7aS)-1-octahydro-1H-indole-2-carboxylic acid which was grafted to the resin (Fmoc-Oic-2-chlorotrityl resin). The linear peptides were synthesized on the solid support according to the procedure described above in the following sequence: Resin-Oic-T$^1$-P$^4$—P$^3$—P$^2$—P$^1$. The products were cleaved from the resin, cyclized, deprotected and purified by preparative reverse phase LC-MS as described above. After lyophilisation the products were obtained as white powders and characterised by HPLC-MS, analytical method A as described above. For analytical data, see Ex. 11, 12, 13, 14, 15, 16, 17, 18, 19, 20, 21, 22, 23, 24, 104 in Table 1.

Examples 25 and 26 are Shown in Table 1.

The peptides were synthesized according general Method A starting with the amino acid D-azetidine-2-carboxylic acid which was grafted to the resin (Fmoc-$^D$Aze-2-chloro-trityl resin). The linear peptides were synthesized on the solid support according to the procedure described above in the following sequence: Resin-$^D$Aze-P$^4$—P$^3$—P$^2$—P$^1$-T$^2$-. The products were cleaved from the resin, cyclized, deprotected and purified by preparative reverse phase LC-MS as described above.

After lyophilisation the products were obtained as white powders and characterised by HPLC-MS, analytical method A for Ex. 25 and analytical method C for Ex. 26 as described above. For analytical data, see Ex. 25, 26 in Table 1.

Examples 27 and 28 are Shown in Table 1.

The peptides were synthesized according general Method A starting with the amino acid (S)-(2,5,3a-5,7a5)-1-octahydro-1H-indole-2-carboxylic acid which was grafted to the resin (Fmoc-Oic-2-chlorotrityl resin). The linear peptides were synthesized on the solid support according to the procedure described above in the following sequence: Resin-Oic-$^D$Pro-Dab-Trp-Cyp-P$^1$. The products were cleaved from the resin, cyclized, depro-tected and purified by preparative reverse phase LC-MS as described above. After lyophilisation the products were obtained as white powders and characterised by HPLC-MS, analytical method C as described above. For analytical data, see Ex. 27, 28 in Table 1.

Example 29 is Shown in Table 1.

The peptide was synthesized according general Method A starting with the amino acid D-proline which was grafted to the resin (Fmoc-$^D$Pro-2-chlorotrityl resin). The linear peptide was synthesized on the solid support according to the procedure described above in the following sequence: Resin-$^D$Pro-Arg-Trp-Cyp-P1-T$^2$. The product was cleaved from the resin, cyclized, deprotected and purified by preparative reverse phase LC-MS as described above.

After lyophilisation the product was obtained as a white powder and characterised by HPLC-MS, analytical method A as described above. For analytical data, see Ex. 29 in Table 1.

Example 30 is Shown in Table 1.

The peptide was synthesized according general Method A starting with the amino acid (R,S)-2-amino-1,2,3,4-tetrahydronaphthalene-2-carboxylic acid which was grafted to the resin (Fmoc-$^{DL}$Atc-2-chlorotrityl resin). The linear peptide was synthesized on the solid support according to the procedure described above in the following sequence: Resin-$^{DL}$-Atc-Trp-Oic-$^D$Pro-Dab-Trp. The product was cleaved from the resin, cyclized, deprotected and purified by preparative reverse phase LC-MS as described above. After lyophilisation the product was obtained as a white powder and characterised by HPLC-MS, analytical method C as described above. For analytical data, see Ex. 30 in Table 1.

Example 31 is Shown in Table 1.

The peptide was synthesized according general Method B starting with the amino acid (S)-(2S,3aS,7aS)-1-octahydro-1H-indole-2-carboxylic acid which was grafted to the resin (Fmoc-Oic-2-chlorotrityl resin). The linear peptide was synthesized on the solid support according to the procedure described above in the following sequence: Resin-Oic-$^D$Pro-Da b-P$^3$—P$^2$—P$^1$. The product was cleaved from the resin, cyclized, deprotected and purified by preparative reverse phase LC-MS as described above.

After lyophilisation the product was obtained as a white powder and characterised by HPLC-MS, analytical method B as described above. For analytical data, see Ex. 31 in Table 1.

Examples 32-34, 36, 58-70, 76, 79-87, 89-96, 107, 109 and 110 are Shown in Table 1.

The peptides were synthesized according general Method B starting with the amino acid (S)-(2S,3aS,7aS)-1-octahydro-1H-indole-2-carboxylic acid which was grafted to the resin (Fmoc-Oic-2-chlorotrityl resin). The linear peptides were synthesized on the solid support according to the procedure described above in the following sequence: Resin-Oic-T$^1$-P$^4$—P$^3$—P$^2$—P$^1$. The products were cleaved from the resin, cyclized, deprotected and purified by preparative reverse phase LC-MS as described above.

For Ex. 76 saponification at the side-chain of P$^1$ occurred. Therefore esterification with MeOH applying standard synthesis procedures was accomplished before purification. After lyophilisation the products were obtained as white to off-white powders and characterised by HPLC-MS, analytical method A or D as described above and indicated in Table 1. For analytical data, see Ex. 32, 33, 34, 36, 58, 59, 60, 61, 62, 63, 64, 65, 66, 67, 68, 69, 70, 76, 79, 80, 81, 82, 83, 84, 85, 86, 87, 89, 90, 91, 92, 93, 94, 95, 96, 107, 109, 110 in Table 1.

Example 35 is Shown in Table 1.

The peptide was synthesized according general Method A starting with the amino acid 2-amino-3-(1H-pyrrolo[2,3-b]pyridin-3-yl)propanoic acid which was grafted to the resin (Fmoc-$^{DL}$Trp(7Aza)-2-chlorotrityl resin). The linear peptide was synthesized on the solid support according to the procedure described above in the following sequence: Resin-$^{DL}$Trp(7Aza)-Cyp-Trp-Oic-$^D$Pro-D a b. The product was cleaved from the resin, cyclized, deprotected and purified by preparative reverse phase LC-MS as described above. After lyophilisation the product was obtained as a white powder and characterised by HPLC-MS, analytical method A as described above. For analytical data, see Ex. 35 in Table 1.

Example 37 is Shown in Table 1.

The peptide was synthesized according general Method B starting with the amino acid 4R-phenyl-L-proline which was grafted to the resin (Fmoc-Pro((4R)Ph)-2-chlorotrityl resin). The linear peptide was synthesized on the solid support according to the procedure described above in the following sequence: Resin-Pro((4R)Ph)-$^D$Pip-Dab-Trp-Cyp-P$^1$. The product was cleaved from the resin, cyclized, deprotected and purified by preparative reverse phase LC-MS as described above.

After lyophilisation the product was obtained as a white powder and characterised by HPLC-MS, analytical method A as described above. For analytical data, see Ex. 37 in Table 1.

Examples 38-42, 52-53 and 57 are Shown in Table 1.

The peptides were synthesized according general Method B starting with the amino acid D-proline which was grafted to the resin (Fmoc-$^D$Pro-2-chlorotrityl resin). The linear peptides were synthesized on the solid support according to the procedure described above in the following sequence: Resin-$^D$Pro-Dab-Trp-Cyp-P$^1$-T$^2$. The products were cleaved from the resin, cyclized, deprotected and purified by preparative reverse phase LC-MS as described above.

After lyophilisation the products were obtained as white powders and characterised by HPLC-MS, analytical method A as described above. For analytical data, see Ex. 38, 39, 40, 41, 42, 52, 53, 57 in Table 1.

Examples 43-50 are Shown in Table 1.

The peptides were synthesized according general Method B starting with the amino acid (2S,4R)-4-benzyloxypyrrolidine-2-carboxylic acid which was grafted to the resin (Fmoc-Hyp(Bn)-2-chlorotrityl resin). The linear peptides were synthesized on the solid support according to the procedure described above in the following sequence: Resin-Hyp(Bn)-T$^1$-P$^4$—P$^3$—P$^2$—P$^1$. The products were cleaved from the resin, cyclized, depro-tected and purified by preparative reverse phase LC-MS as described above.

After lyophilisation the products were obtained as white powders and characterised by HPLC-MS, analytical method A as described above. For analytical data, see Ex. 43, 44, 45, 46, 47, 48, 49, 50 in Table 1.

Example 51 is Shown in Table 1.

The peptide was synthesized according general Method B starting with the amino acid (2S,4S)-4-benzyloxypyrrolidine-2-carboxylic acid which was grafted to the resin (Fmoc-(4S)-Hyp(Bn)-2-chlorotrityl resin). The linear peptides was synthesized on the solid support according to the procedure described above in the following sequence: Resin-Hyp(Bn)-$T^1$-$P^4$—$P^3$—$P^2$—$P^1$. The products was cleaved from the resin, cyclized, deprotected and purified by preparative reverse phase LC-MS as described above.

After lyophilisation the product was obtained as a white powder and characterised by HPLC-MS, analytical method A as described above. For analytical data, see Ex. 51 in Table 1.

Examples 54-56 are Shown in Table 1.

The peptides were synthesized according general Method B starting with the amino acid (2S,4R)-4-(4-bromobenzyl)-pyrrolidine-2-carboxylic acid which was grafted to the resin (Fmoc-Hyp(4BrBn)-2-chlorotrityl resin). The linear peptides were synthesized on the solid support according to the procedure described above in the following sequence: Resin-Hyp(4BrBn)-$^D$Pro-$P^4$—$P^3$—$P^2$—$P^1$. The products were cleaved from the resin, cyclized, deprotected and purified by preparative reverse phase LC-MS as described above.

After lyophilisation the products were obtained as white powders and characterised by HPLC-MS, analytical method A as described above.

For analytical data, see Ex. 54, 55, 56 in Table 1.

Example 78 is Shown in Table 1.

The peptide was synthesized according general Method A starting with the amino acid (2S)-3-(4-cyanophenyl)-2-amino)propanoic acid which was grafted to the resin (Fmoc-Phe(4CN)-2-chlorotrityl resin). The linear peptide was synthesized on the solid support according to the procedure described above in the following sequence: Resin-Phe(4CN)-Oic-$^D$Pro-Dab-Trp-Cyp. The product was cleaved from the resin, cyclized, deprotected and purified by preparative reverse phase LC-MS as described above. After lyophilisation the product was obtained as a white powder and characterised by HPLC-MS, analytical method A as described above. For analytical data, see Ex. 78 in Table 1.

Example 88 is Shown in Table 1.

The peptide was synthesized according general Method A starting with the amino acid (2S)-3-(1-benzothiophen-3-yl)-2-amino propanoic acid which was grafted to the resin (Fmoc-Bbta-2-chlorotrityl resin). The linear peptide was synthesized on the solid support according to the procedure described above in the following sequence: Resin-Bbta-Oic-$^D$Pro-Dab-Trp-Cyp. The product was cleaved from the resin, cyclized, deprotected and purified by preparative reverse phase LC-MS as described above. After lyophilisation the product was obtained as a white powder and characterised by HPLC-MS, analytical method A as described above. For analytical data, see Ex. 88 in Table 1.

Example 103 is Shown in Table 1.

The peptides were synthesized according general Method A starting with the amino acid (S)-2,4-diaminobutanoic acid which was grafted to the resin (Fmoc-Dab-2-chlorotrityl resin). The linear peptide was synthesized on the solid support according to the procedure described above in the following sequence: Resin-Dab-Trp-Cyp-Trp-$T^2$-$T^1$. The product was cleaved from the resin, cyclized, deprotected and purified by preparative reverse phase LC-MS as described above.

After lyophilisation the product was obtained as white powders and characterised by HPLC-MS, analytical method A as described above. For analytical data, see Ex. 103 in Table 1.

1.5 Post peptide sequence modifications

Examples 74 and 75 as Shown in Table 1.

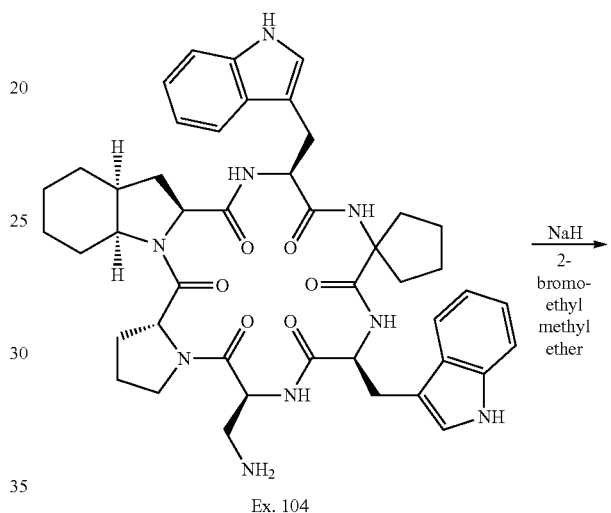

Ex. 104

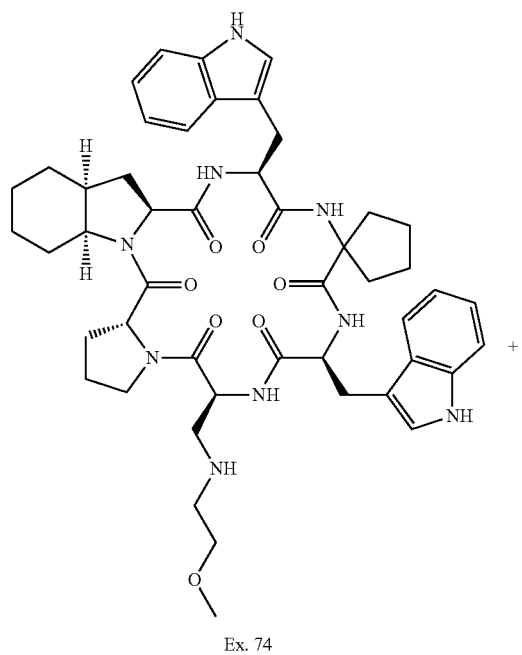

Ex. 74

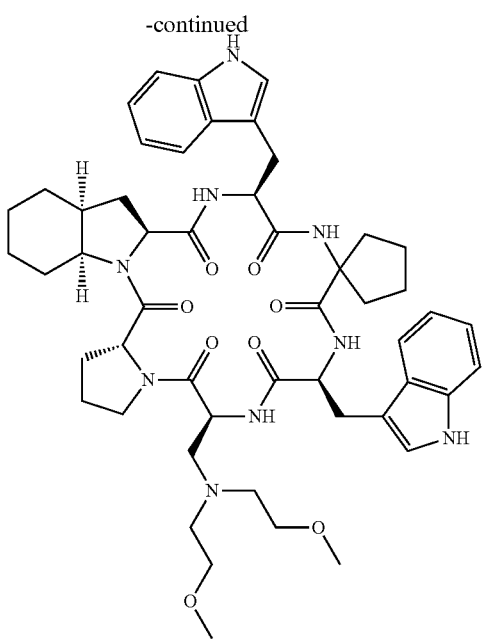

Ex. 75

To a solution of 40 mg Ex. 104 (44 µmol) in 0.5 ml dry DMF was added 4 mg sodium hydride (55% in mineral oil, 87 µmol) at 0° C. The suspension was stirred at 0° C. for 10 min, then sodium iodide (3.3 mg, 22 µmol) and 2-bromoethyl methyl ether (6 µl, 66 µmol) were added. The reaction mixture was stirred overnight at rt. To complete the reaction the above addition sequence was repeated involving another 9 mg sodium hydride and 20 µl 2-bromoethyl methyl ether. Then some drops of water were added, the reaction mixture was concentrated and purified by preparative reverse phase LC-MS as described above. After lyophilisation 1.7 mg of Ex. 74 and 1.8 mg of Ex. 75 was obtained as off-white powders and characterised by HPLC-MS, analytical method A as described above.

For analytical data, see Ex. 74 and Ex. 75 in Table 1.

Example 73 as Shown in Table 1.

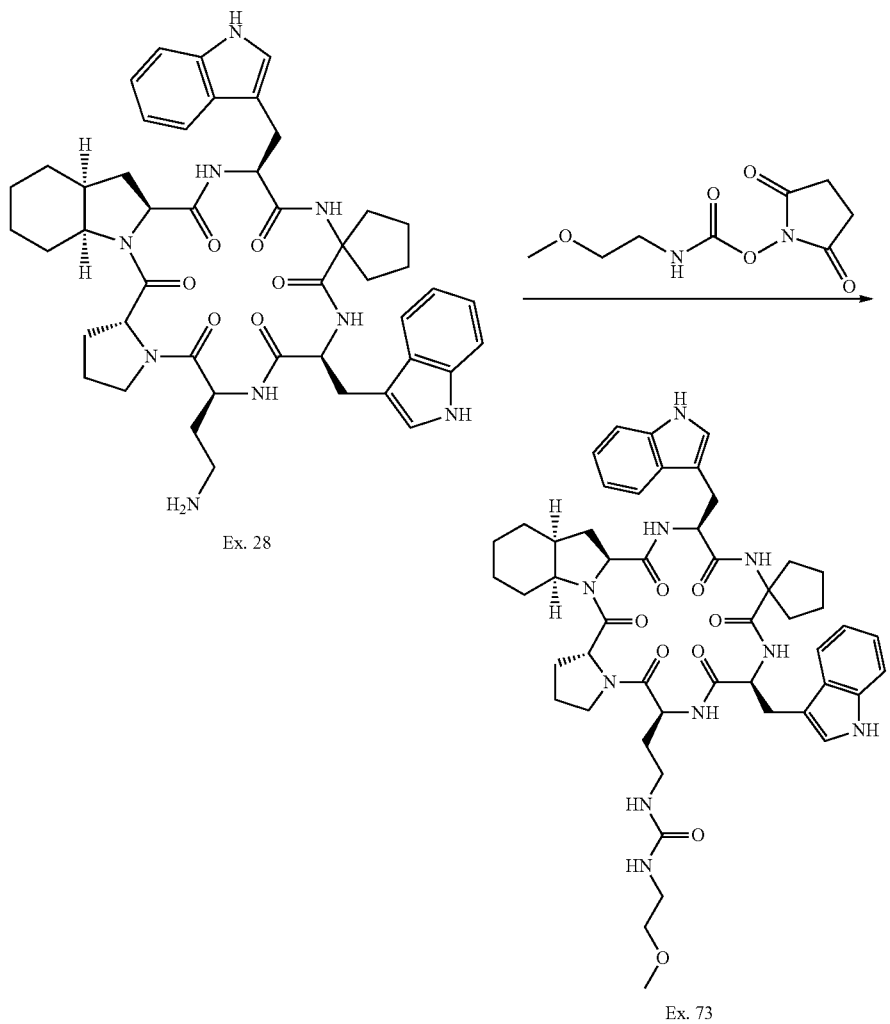

To a solution of 15 mg Ex. 28 (18 μmol) and 9 μl DIPEA (54 μmol) in 0.5 ml dry THF was added 8 mg of N-succinimidyl-N-(2-methoxyethyl)carbamate (36 μmol) and the mixture was stirred overnight at rt. The reaction mixture was concentrated and purified by preparative reverse phase LC-MS as described above. After lyophilisation 2 mg of Ex. 73 was obtained and characterised by HPLC-MS, analytical method A as described above.

For analytical data, see Ex. 73 in Table 1.

Example 71 as Shown in Table 1.

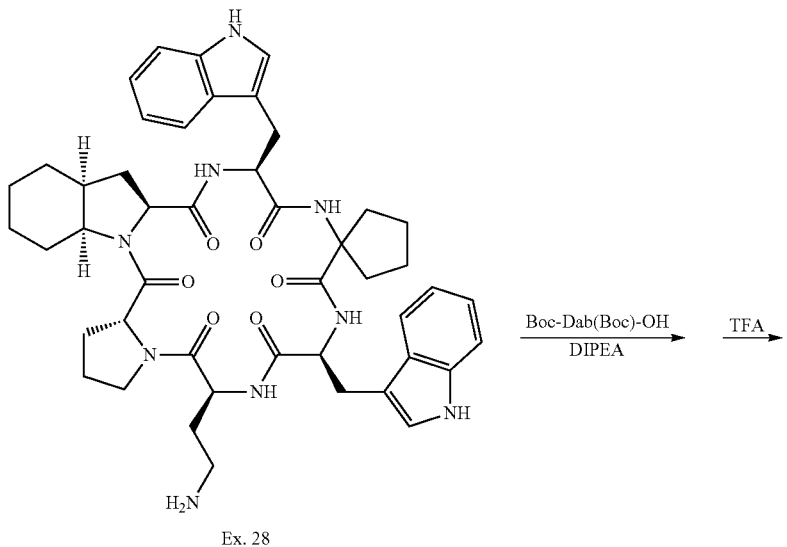

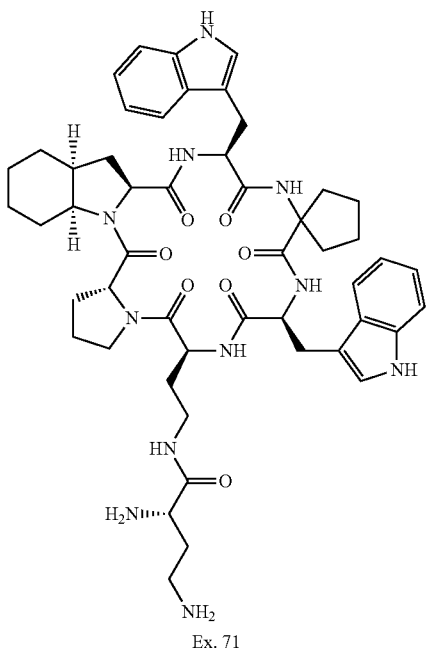

A solution of 20 mg Ex. 28 (24 µmol), 36 mg Boc-Dab (Boc)-OH-DCHA (72 µmol), 38 mg PyBOP (72 µmol) and 25 µl DIPEA (144 µmol) in 0.5 ml dry DMF was stirred overnight at rt. The reaction mixture was concentrated, resuspended in CH$_2$Cl$_2$, washed with water and concentrated again. The crude material was dissolved in 3 ml TFA containing 0.1 ml of water. After 2 h at rt the solution was concentrated and then purified by preparative reverse phase LC-MS as described above. After lyophilisation 2.5 mg of Ex. 71 was obtained and characterised by HPLC-MS, analytical method A as described above.

For analytical data, see Ex. 71 in Table 1.

Example 72 as Shown in Table 1.

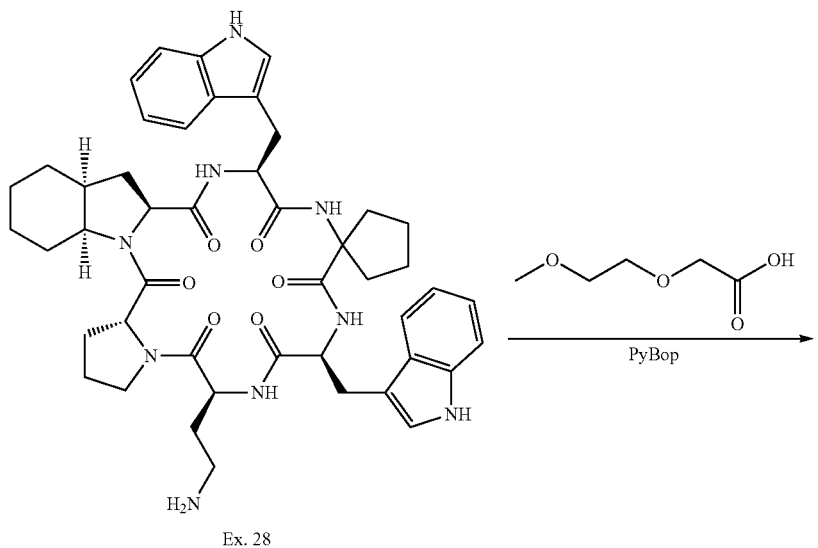

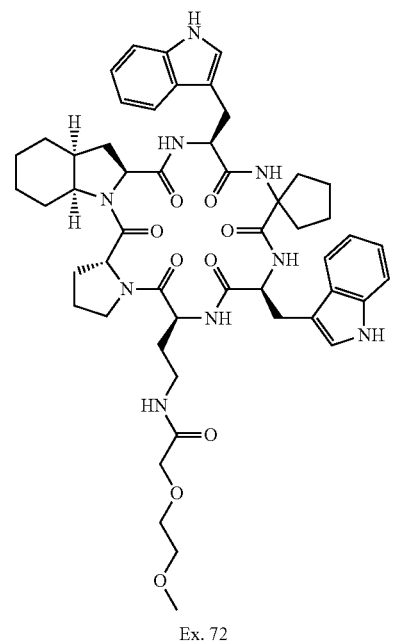

To a solution of 42 mg Ex. 28 (50 µmol) and 26 µl DIPEA (150 µmol) in 1 ml dry DMF was added 14 mg of 2-(2-methoxyethoxy)acetic acid (100 µmol) and 53 mg of PyBOP (100 µmol). The reaction mixture was stirred for 1 h at rt, concentrated and purified by preparative reverse phase LC-MS as described above. After lyophilisation 7 mg of Ex. 72 was obtained and characterised by HPLC-MS, analytical method A as described above.

For analytical data, see Ex. 72 in Table 1.
Example 108 as Shown in Table 1.

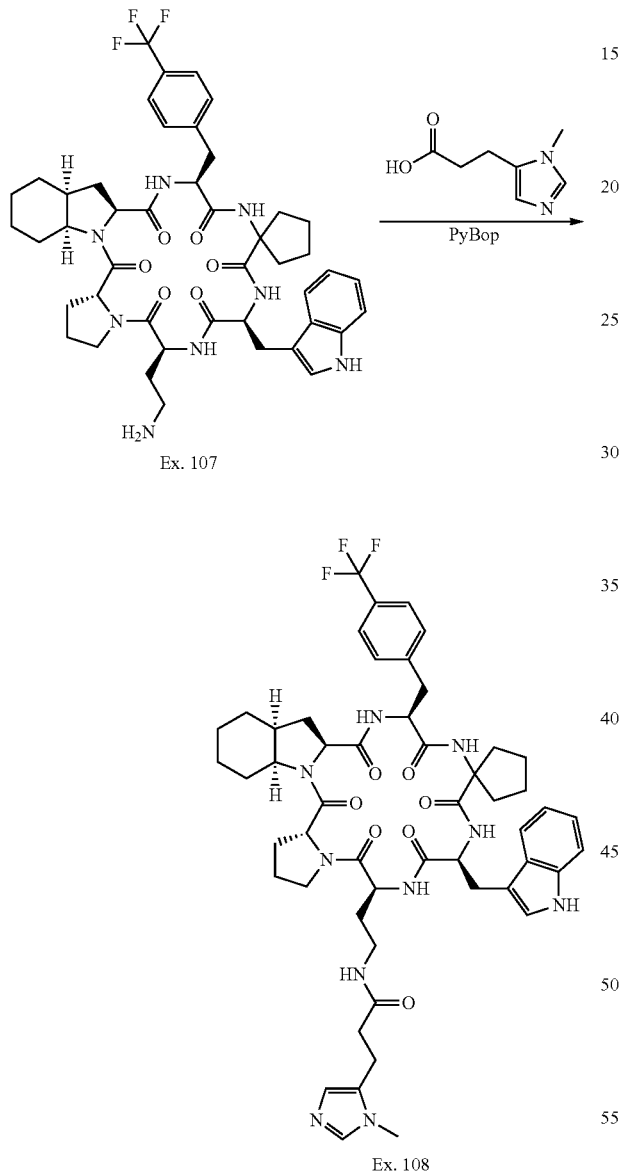

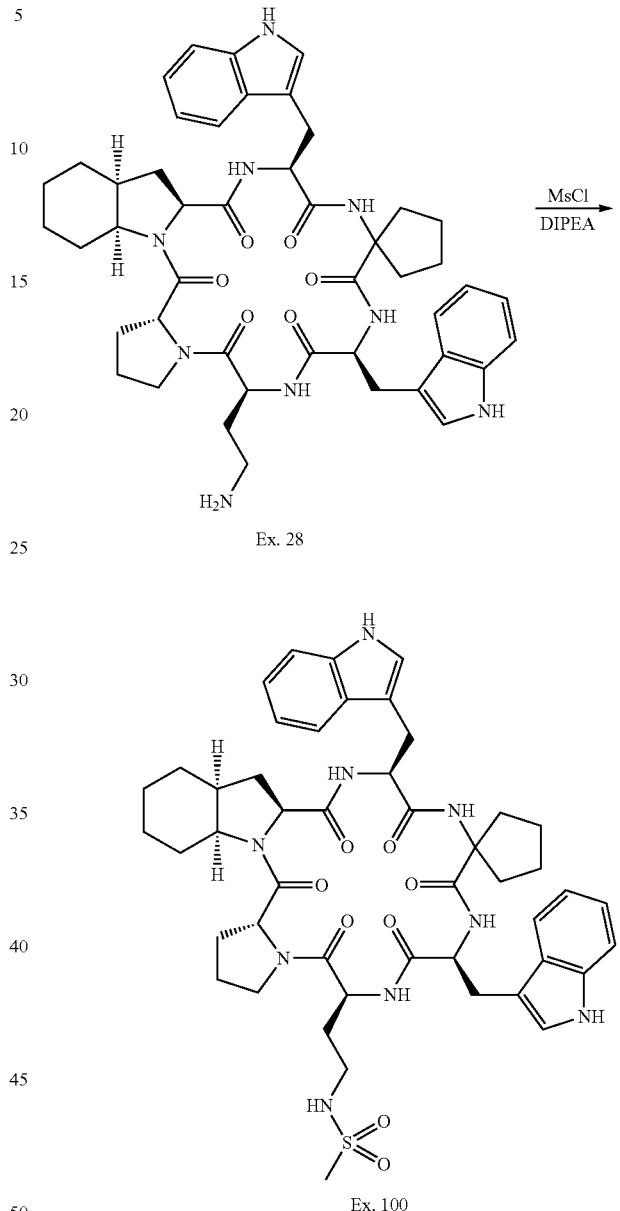

To a solution of 59 mg Ex. 107 (61 µmol) and 41 µl DIPEA (242 µmol) in 1.2 ml dry DMF was added 19 mg of 3-(1-methyl-1H-imidazol-5-yl)propanoic acid (121 µmol) and 63 mg of PyBOP (121 µmol). The reaction mixture was stirred for 1 h at rt, concentrated and purified by preparative reverse phase LC-MS as described above. After lyophilisation 30 mg of Ex. 108 was obtained and characterised by HPLC-MS, analytical method D as described above.

For analytical data, see Ex. 108 in Table 1.
Example 100 as Shown in Table 1.

To a solution of 25 mg Ex. 28 (free base; 28 µmol) and 19 µl DIPEA (112 µmol) in 1 ml dry THF/CHCl$_3$/CH$_2$Cl$_2$ (1:1:2) was added 6.5 µl methansulfonyl chloride (84 µmol) and a catalytic amount of DMAP and the reaction mixture was stirred overnight at rt. Then additional 6.5 µl methansulfonyl chloride (84 µmol) and 19 µl DIPEA (112 µmol) were added, stirred for 4 h at rt, finally concentrated and purified by preparative reverse phase LC-MS as described above. After lyophilisation 3 mg of Ex. 100 was obtained and characterised by HPLC-MS, analytical method A as described above.

For analytical data, see Ex. 100 in Table 1.
Example 101 as Shown in Table 1.
Analogue to the procedure for Ex. 100 but employing 2×18.5 µl of 4-(dimethylamino)-benzene-1-sulfonyl chloride (2×84 µmol). After purification by preparative reverse phase LC-MS and lyophilisation, 10 mg of Ex. 101 was obtained and characterised by HPLC-MS, analytical method A as described above.

For analytical data, see Ex. 101 in Table 1.

Example 105 as Shown in Table 1.

Analogue to the procedure for Ex. 100 but employing 22 mg of Ex. 28 (free base; 25 µmol), 16 mg of sodium carbonate (144 µmol) and 34 mg of 4-methylpiperazine-1-sulfonyl chloride (144 µmol) in THF. After purification by preparative reverse phase LC-MS and lyophilisation, 5 mg of Ex. 105 was obtained and characterised by HPLC-MS, analytical method A as described above.

For analytical data, see Ex. 105 in Table 1.

Preparation of Intermediate (II).

52 mg of N,N"-disuccinimidyl carbonate (free base; 202 µmol) was suspended in 2 ml dry $CH_2Cl_2$, cooled to 0° C. and 32 µl DIPEA (185 µmol) was added. Then a solution of 150 mg Ex. 28 (168 µmol) in 2.5 ml dry acetonitrile/$CH_2Cl_2$ (1:1) was added dropwise over 10 min. The reaction mixture was stirred at rt for 7 h before additional 15 µl DIPEA (84 µmol) and 22 mg of N,N"-disuccinimidyl carbonate (84 µmol) was added. The suspension was stirred overnight at rt, then concentrated, precipitated and washed twice with diethylether to yield 177 mg crude (II) as a white solid.

Example 97 as Shown in Table 1.

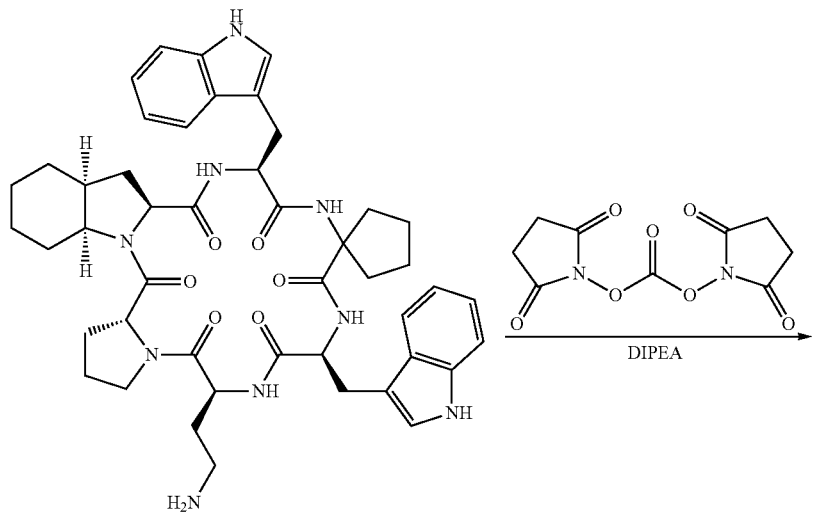

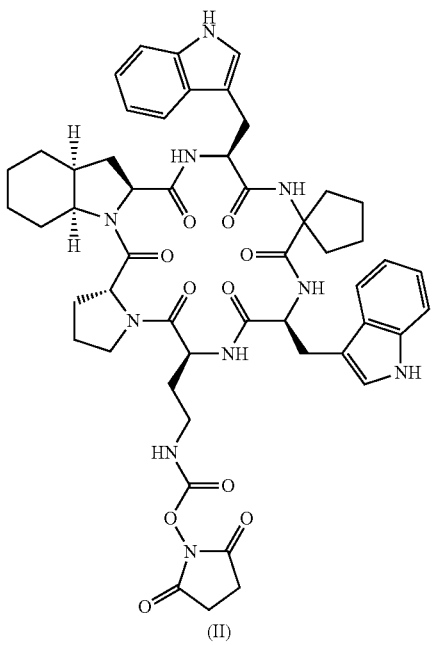

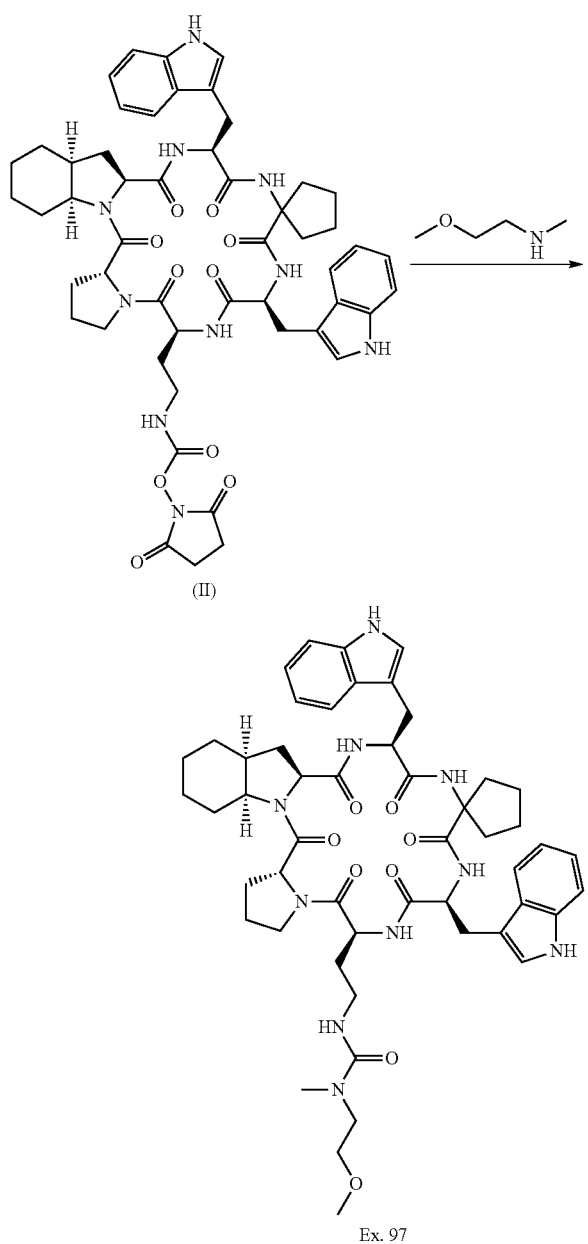

Ex. 97

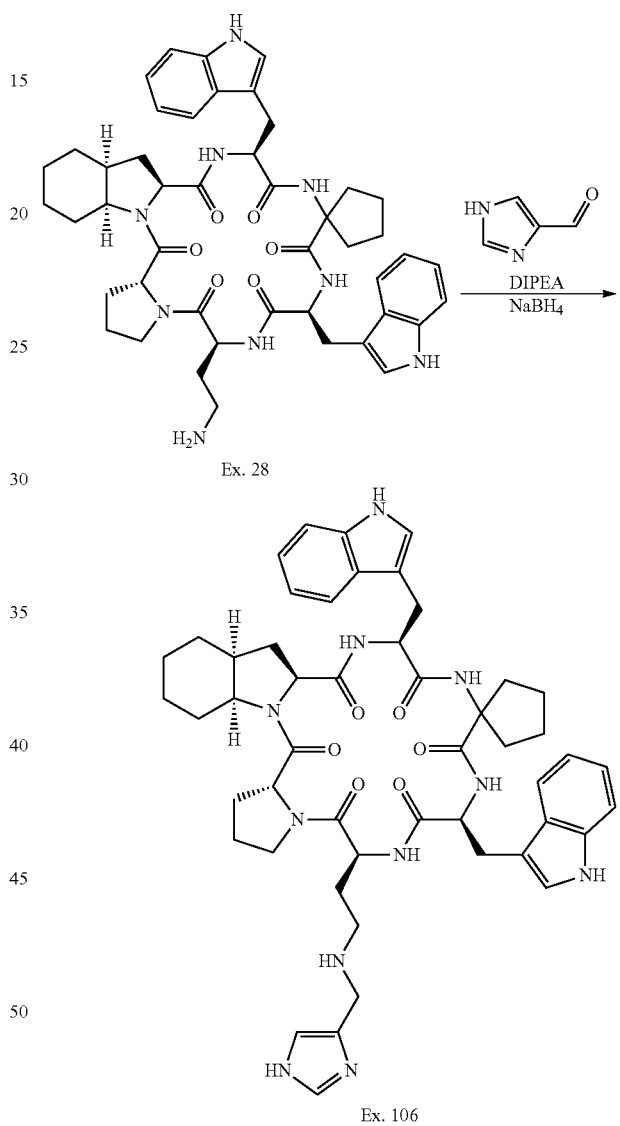

Ex. 106

25 mg of succinimidyl carbamate (II) (26 μmol) and 9 μl 2-methoxy-N-methylethylamine (77 μmol) were combined in 1 ml dry THF. The reaction mixture was stirred for 2 h at rt, concentrated and purified by preparative reverse phase LC-MS as described above. After lyophilisation 8 mg of Ex. 97 was obtained and characterised by HPLC-MS, analytical method A as described above. For analytical data, see Ex. 97 in Table 1.

Example 98 as Shown in Table 1.

Analogue to the procedure for Ex. 97 but employing 20 mg of (II) (21 μmol) and 6 μl morpholine (62 μmol). After purification by preparative reverse phase LC-MS and lyo-philisation, 3 mg of Ex. 98 was obtained and characterised by HPLC-MS, analytical method A as described above. For analytical data, see Ex. 98 in Table 1.

Example 99 as Shown in Table 1.

Analogue to the procedure for Ex. 97 but employing 20 mg of (II) (21 μmol) and 7 μl N-methylpiperazine (62 μmol). After purification by preparative reverse phase LC-MS and lyophilisation, 7 mg of Ex. 99 was obtained and characterised by HPLC-MS, analytical method A as described above. For analytical data, see Ex. 99 in Table 1.

Example 106 as Shown in Table 1.

To a solution of 40 mg Ex. 28 (42 μmol) and 22 μl DIPEA (127 μmol) in 1.0 ml dry THF was added 6.1 mg 1H-imida-zole-4-carbaldehyde (63 μmol). After 5 h at rt, 3.2 mg sodium borohydride (85 μmol) was added and the reaction mixture monitored for completion (ca. 15 min). A few drops of water were added and the mixture was concentrated and purified by preparative reverse phase LC-MS as described above. After lyophilisation 13 mg of Ex. 106 was obtained as a white solid and characterised by HPLC-MS, analytical method D as described above.

For analytical data, see Ex. 106 in Table 1.

1.6 Sequence Data

TABLE 1

| | | | | Examples | | |
|---|---|---|---|---|---|---|
| Ex. | Sequence ID | P1 [a] | P2 [a] | P3 [a] | P4 [a] | T1 [a] |
| 1 | SEQ ID NO: 1 | Trp | Aib | Trp | Arg | [D]Pro |
| 2 | SEQ ID NO: 2 | Trp | Aib | Trp | Dab | [D]Pro |
| 3 | SEQ ID NO: 3 | Trp | Cyp | Trp | Arg | [D]Pro |
| 4 | SEQ ID NO: 4 | Trp | Cyp | Trp | Dab | [D]Pro |
| 5 | SEQ ID NO: 5 | Trp | Cyp | Trp | Arg | [D]Pro |
| 6 | SEQ ID NO: 6 | Trp | Cyp | Trp | Dab | [D]Pro |
| 7 | SEQ ID NO: 7 | Trp(5OH) | Cyp | Trp | Gln | [D]Pro |
| 8 | SEQ ID NO: 8 | Trp(5OH) | Cyp | Trp | Arg | [D]Pro |
| 9 | SEQ ID NO: 9 | 2Nal | Cyp | Trp | Gln | [D]Pro |
| 10 | SEQ ID NO: 10 | 2Nal | Cyp | Trp | Dab | [D]Pip |
| 11 | SEQ ID NO: 11 | Trp(5OH) | Chx | Trp(5OH) | Arg | [D]Pro |
| 12 | SEQ ID NO: 12 | Trp(5OH) | Cyp | Trp(5OH) | Dap | [D]Pro |
| 13 | SEQ ID NO: 13 | Trp | Cyp | Trp | Dab | [D]Pip |
| 14 | SEQ ID NO: 14 | Trp | Cyp | 2Nal | Dab | [D]Pip |
| 15 | SEQ ID NO: 15 | Trp | Cyp | 2Nal | Gln | [D]Pro |
| 16 | SEQ ID NO: 16 | OctG | Cyp | Trp | Dab | [D]Pro |
| 17 | SEQ ID NO: 17 | Trp | Cyp | Trp | Gln | [D]Pro |
| 18 | SEQ ID NO: 18 | Trp | Chx | Trp | Dab | [D]Pro |
| 19 | SEQ ID NO: 19 | Trp | Ac3c | Trp | Dab | [D]Pro |
| 20 | SEQ ID NO: 20 | Trp | Ac4c | Trp | Dab | [D]Pro |
| 21 | SEQ ID NO: 21 | Trp | 4,4-AC-ThioTHP | Trp | Dab | [D]Pro |
| 22 | SEQ ID NO: 22 | Trp | Cyp | Phe(4F) | Dab | [D]Pro |
| 23 | SEQ ID NO: 23 | Trp | Cyp | Tyr(Me) | Dab | [D]Pro |
| 24 | SEQ ID NO: 24 | Trp | Cyp | Ala(2Quin) | Dab | [D]Pro |
| 25 | SEQ ID NO: 25 | Trp | Cyp | Trp | Arg | [D]Aze |
| 26 | SEQ ID NO: 26 | Trp | Cyp | Trp | Dab | [D]Aze |
| 27 | SEQ ID NO: 27 | Cha | Cyp | Trp | Dab | [D]Pro |
| 28 | SEQ ID NO: 28 | Trp | Cyp | Trp | Dab | [D]Pro |
| 29 | SEQ ID NO: 29 | Trp(5OH) | Cyp | Trp | Arg | [D]Pro |
| 30 | SEQ ID NO: 30 | Trp | [DL]Atc | Trp | Dab | [D]Pro |
| 31 | SEQ ID NO: 31 | Trp | Cyp | Ala(2Furyl) | Dab | [D]Pro |
| 32 | SEQ ID NO: 32 | Trp | Cyp | Phe(4F) | Ser | [D]Pro |
| 33 | SEQ ID NO: 33 | Trp | Cyp | Phe(4Cl) | Ser | [D]Pro |
| 34 | SEQ ID NO: 34 | Trp | Cyp | Phe(4CF$_3$) | Dab | [D]Pro |
| 35 | SEQ ID NO: 35 | Trp | Cyp | [DL]Trp(7Aza) | Dab | [D]Pro |
| 36 | SEQ ID NO: 36 | Trp | Cyp | Tyr(Ph) | Dab | [D]Pro |
| 37 | SEQ ID NO: 37 | Phe(4CF$_3$) | Cyp | Trp | Dab | [D]Pip |
| 38 | SEQ ID NO: 38 | Trp | Cyp | Trp | Dab | [D]Pro |
| 39 | SEQ ID NO: 39 | Trp | Cyp | Trp | Dab | [D]Pro |
| 40 | SEQ ID NO: 40 | Trp | Cyp | Trp | Dab | [D]Pro |
| 41 | SEQ ID NO: 41 | Trp | Cyp | Trp | Dab | [D]Pro |
| 42 | SEQ ID NO: 42 | Trp | Cyp | Trp | Dab | [D]Pro |
| 43 | SEQ ID NO: 43 | Trp | Cyp | Phe(4Cl) | Dab | [D]Pro |
| 44 | SEQ ID NO: 44 | Phe(4CN) | Cyp | Phe(4F) | Ser | [D]Pro |
| 45 | SEQ ID NO: 45 | Trp | Cyp | Trp | Dab | [D]Pro |
| 46 | SEQ ID NO: 46 | Trp | Cyp | Trp | Ser | [D]Pro |
| 47 | SEQ ID NO: 47 | Phe(4CN) | Cyp | Trp | Gln | [D]Pro |
| 48 | SEQ ID NO: 48 | Trp(6Cl) | Cyp | Trp | Dab | [D]Pro |
| 49 | SEQ ID NO: 49 | Phe(4CN) | Cyp | Trp | Dab | [D]Pro |
| 50 | SEQ ID NO: 50 | Phe(4CN) | Cyp | Trp | Ser | [D]Pip |
| 51 | SEQ ID NO: 51 | Trp | Cyp | Trp | Dab | [D]Pro |
| 52 | SEQ ID NO: 52 | Trp | Cyp | Trp | Dab | [D]Pro |
| 53 | SEQ ID NO: 53 | Trp | Cyp | Trp | Dab | [D]Pro |
| 54 | SEQ ID NO: 54 | Phe(4CF$_3$) | Cyp | Trp | Dab | [D]Pro |
| 55 | SEQ ID NO: 55 | Phe(4CN) | Cyp | Trp | Ser | [D]Pro |
| 56 | SEQ ID NO: 56 | Trp | Cyp | Trp | Dab | [D]Pro |
| 57 | SEQ ID NO: 57 | Trp | Cyp | Trp | Dab | [D]Pro |
| 58 | SEQ ID NO: 58 | Trp | Cyp | Trp | alloThr | [D]Pro |
| 59 | SEQ ID NO: 59 | Trp | Cyp | Trp | hArg | [D]Pro |
| 60 | SEQ ID NO: 60 | Trp | Cyp | Trp | hCis | [D]Pro |
| 61 | SEQ ID NO: 61 | Trp | Cyp | Trp | Gln(iPr) | [D]Pro |
| 62 | SEQ ID NO: 62 | Trp | Cyp | Trp | hSer(Me) | [D]Pro |
| 63 | SEQ ID NO: 63 | Trp | Cyp | Trp | Lys(Ac) | [D]Pro |
| 64 | SEQ ID NO: 64 | Trp | Cyp | Trp | Lys(Bz) | [D]Pro |
| 65 | SEQ ID NO: 65 | Trp | Cyp | Trp | Lys(Me) | [D]Pro |
| 66 | SEQ ID NO: 66 | Trp | Cyp | Trp | Lys((5R)OH) | [D]Pro |
| 67 | SEQ ID NO: 67 | Trp | Cyp | Trp | Lys(Nic) | [D]Pro |
| 68 | SEQ ID NO: 68 | Trp | Cyp | Trp | Met(O$_2$) | [D]Pro |
| 69 | SEQ ID NO: 69 | Trp | Cyp | Trp | Ala(Ppz) | [D]Pro |
| 70 | SEQ ID NO: 70 | Trp | Cyp | Trp | Dap(CONH$_2$) | [D]Pro |
| 71 | SEQ ID NO: 71 | Trp | Cyp | Trp | Dab(Dab) | [D]Pro |
| 72 | SEQ ID NO: 72 | Trp | Cyp | Trp | Dab(MEMCO) | [D]Pro |
| 73 | SEQ ID NO: 73 | Trp | Cyp | Trp | Dab(MeO(CH$_2$)$_2$NCO) | [D]Pro |

TABLE 1-continued

Examples

| | | | | | | |
|---|---|---|---|---|---|---|
| 74 | SEQ ID NO: 74 | Trp | Cyp | Trp | Dap(MeO(CH$_2$)$_2$) | $^D$Pro |
| 75 | SEQ ID NO: 75 | Trp | Cyp | Trp | Dap((MeO (CH$_2$)$_2$)$_2$) | $^D$Pro |
| 76 | SEQ ID NO: 76 | Phe(4CO OMe) | Cyp | Trp | Dab | $^D$Pro |
| 77 | SEQ ID NO: 77 | Trp | Cyp | Trp | Dab | $^D$Pro |
| 78 | SEQ ID NO: 78 | Phe(4CN) | Cyp | Trp | Dab | $^D$Pro |
| 79 | SEQ ID NO: 79 | Trp | Cyp | Trp | Ser | $^D$Pro |
| 80 | SEQ ID NO: 80 | Trp | Cyp | Trp | Ser | $^D$Pip |
| 81 | SEQ ID NO: 81 | Trp(6Cl) | Cyp | Trp | Ser | $^D$Pro |
| 82 | SEQ ID NO: 82 | Phe(4CN) | Cyp | Trp | Ser | $^D$Pro |
| 83 | SEQ ID NO: 83 | Trp | Cyp | Trp | Lys(4Oxa) | $^D$Pro |
| 84 | SEQ ID NO: 84 | Trp | Cyp | Trp | Ser(Me) | $^D$Pro |
| 85 | SEQ ID NO: 85 | Trp | Cyp | Trp | Thr | $^D$Pro |
| 86 | SEQ ID NO: 86 | Bip | Cyp | Trp | Dab | $^D$Pro |
| 87 | SEQ ID NO: 87 | hTyr | Cyp | Trp | Dab | $^D$Pro |
| 88 | SEQ ID NO: 88 | Bbta | Cyp | Trp | Dab | $^D$Pro |
| 89 | SEQ ID NO: 89 | Nle(6OBn) | Cyp | Trp | Dab | $^D$Pro |
| 90 | SEQ ID NO: 90 | Phe(4OHPh) | Cyp | Trp | Dab | $^D$Pro |
| 91 | SEQ ID NO: 91 | Tyr(Ph) | Cyp | Trp | Dab | $^D$Pro |
| 92 | SEQ ID NO: 92 | Tyr(4MeO COBn) | Cyp | Trp | Dab | $^D$Pro |
| 93 | SEQ ID NO: 93 | Trp | Deg | Trp | Dab | $^D$Pro |
| 94 | SEQ ID NO: 94 | Trp | Ac7c | Trp | Dab | $^D$Pro |
| 95 | SEQ ID NO: 95 | Trp | Chx(4oxo) | Trp | Dab | $^D$Pro |
| 96 | SEQ ID NO: 96 | Trp | Ac8c | Trp | Dab | $^D$Pro |
| 97 | SEQ ID NO: 97 | Trp | Cyp | Trp | Dab((MeO(CH$_2$)$_2$) (Me)NCO) | $^D$Pro |
| 98 | SEQ ID NO: 98 | Trp | Cyp | Trp | Dab(morphCO) | $^D$Pro |
| 99 | SEQ ID NO: 99 | Trp | Cyp | Trp | Dab(MePpzCO) | $^D$Pro |
| 100 | SEQ ID NO: 100 | Trp | Cyp | Trp | Dab(MeSO$_2$) | $^D$Pro |
| 101 | SEQ ID NO: 101 | Trp | Cyp | Trp | Dab(4Me$_2$N PhSO$_2$) | $^D$Pro |
| 102 | SEQ ID NO: 102 | Trp | Cyp | Trp | Dab(Ac) | $^D$Pro |
| 103 | SEQ ID NO: 103 | Trp | Cyp | Trp | Dab | $^D$Pro |
| 104 | SEQ ID NO: 104 | Trp | Cyp | Trp | Dap | $^D$Pro |
| 105 | SEQ ID NO: 105 | Trp | Cyp | Trp | Dab(SN13) | $^D$Pro |
| 106 | SEQ ID NO: 106 | Trp | Cyp | Trp | Dab(A55) | $^D$Pro |
| 107 | SEQ ID NO: 107 | Phe(4CF$_3$) | Cyp | Trp | Dab | $^D$Pro |
| 108 | SEQ ID NO: 108 | Phe(4CF$_3$) | Cyp | Trp | Dab(A56) | $^D$Pro |
| 109 | SEQ ID NO: 109 | Phe(3CF$_3$) | Cyp | Trp | Dab | $^D$Pro |
| 110 | SEQ ID NO: 110 | Phe(4CF$_3$) | Cyp | Trp | 3Pal | $^D$Pic |

| Ex. | T2 $^{a)}$ | Synth. Method | Purity % $^{b)}$ | [M + H]$^+$ | RT [min] | Anal. Method |
|---|---|---|---|---|---|---|
| 1 | Tic | A | 94 | 870.3 | 1.79 | A |
| 2 | Tic | A | 96 | 814.3 | 1.78 | A |
| 3 | Tic(7OH) | A | 98 | 912.7 | 1.75 | A |
| 4 | Pro((4S)F) | A | >98 | 796.3 | 1.66 | A |
| 5 | Thz | A | 95 | 852.4 | 1.74 | A |
| 6 | Thz | A | >98 | 796.3 | 1.71 | A |
| 7 | Thz | A | 95 | 840.2 | 1.71 | A |
| 8 | Tic | A | 93 | 912.7 | 1.71 | A |
| 9 | Tic | A | 92 | 879.5 | 2.14 | A |
| 10 | Pip | A | 91 | 817.4 | 1.92 | A |
| 11 | Oic | A | 88 | 934.7 | 1.64 | A |
| 12 | Oic | A | 96 | 850.3 | 1.56 | A |
| 13 | Oic | A | >98 | 846.4 | 1.88 | A |
| 14 | Oic | A | 94 | 857.3 | 1.99 | A |
| 15 | Oic | A | 79 | 871.3 | 2.13 | A |
| 16 | Oic | A | 98 | 815.4 | 2.08 | A |
| 17 | Oic | A | 91 | 860.5 | 1.99 | A |
| 18 | Oic | A | 96 | 846.3 | 1.86 | A |
| 19 | Oic | A | 97 | 804.4 | 1.75 | A |
| 20 | Oic | A | 96 | 818.3 | 1.79 | A |
| 21 | Oic | A | 97 | 864.3 | 1.82 | A |
| 22 | Oic | A | 72 | 811.4 | 1.86 | A |
| 23 | Oic | A | 88 | 823.3 | 1.83 | A |
| 24 | Oic | A | 97 | 844.5 | 1.61 | A |
| 25 | Tic | A | 97 | 882.4 | 1.84 | A |
| 26 | Tic | A | 95 | 826.8 | 3.23 | C |
| 27 | Oic | A | 95 | 799.2 | 3.66 | C |
| 28 | Oic | A | 90 | 832.2 | 3.38 | C |
| 29 | Thz(5,5Me$_2$) | A | 92 | 896.3 | 1.69 | A |
| 30 | Oic | A | >98 | 894.4 | 3.77; 3.82 $^{c)}$ | C |
| 31 | Oic | B | 84 | 783.4 | 2.17 | B |
| 32 | Oic | B | >98 | 798.4 | 2.10 | A |
| 33 | Oic | B | 98 | 814.4 | 2.17 | A |
| 34 | Oic | B | 91 | 861.4 | 1.97 | A |
| 35 | Oic | A | 93 | 833.3 | 1.58 | A |
| 36 | Oic | B | 93 | 885.3 | 2.02 | A |
| 37 | Pro((4R)Ph) | B | 92 | 897.3 | 2.02 | A |

TABLE 1-continued

| | Examples | | | | | |
|---|---|---|---|---|---|---|
| 38 | Pro((4R)Bn) | B | 89 | 868.4 | 1.91 | A |
| 39 | Pro((4R)4BrBn) | B | 90 | 948.4 | 1.99 | A |
| 40 | Pro((4R)3CNBn) | B | 96 | 893.5 | 1.86 | A |
| 41 | Pro((4S)cHex) | B | 93 | 860.4 | 1.98 | A |
| 42 | Pro(5,5Me$_2$) | B | 98 | 806.3 | 1.76 | A |
| 43 | Hyp(Bn) | B | 96 | 879.4 | 1.98 | A |
| 44 | Hyp(Bn) | B | 92 | 836.4 | 2.16 | A |
| 45 | Hyp(Bn) | B | >98 | 884.7 | 1.87 | A |
| 46 | Hyp(Bn) | B | 98 | 871.5 | 2.10 | A |
| 47 | Hyp(Bn) | B | 93 | 898.3 | 2.02 | A |
| 48 | Hyp(Bn) | B | 97 | 918.4 | 1.96 | A |
| 49 | Hyp(Bn) | B | 96 | 870.3 | 1.84 | A |
| 50 | Hyp(Bn) | B | 93 | 871.5 | 2.19 | A |
| 51 | (4S)-Hyp(Bn) | B | 96 | 884.3 | 1.84 | A |
| 52 | Hyp(Ph) | B | 95 | 870.4 | 1.88 | A |
| 53 | Hyp(4CNBn) | B | 95 | 909.5 | 1.85 | A |
| 54 | Hyp(4BrBn) | B | 97 | 991.5 | 2.09 | A |
| 55 | Hyp(4BrBn) | B | 93 | 937.4 | 2.22 | A |
| 56 | Hyp(4BrBn) | B | 93 | 962.5 | 1.99 | A |
| 57 | Hyp(CONHPh) | B | 98 | 913.4 | 1.87 | A |
| 58 | Oic | B | 95 | 833.3 | 2.11 | A |
| 59 | Oic | B | 94 | 902.4 | 1.86 | A |
| 60 | Oic | B | 96 | 903.4 | 2.00 | A |
| 61 | Oic | B | 97 | 902.4 | 2.17 | A |
| 62 | Oic | B | 97 | 847.3 | 2.19 | A |
| 63 | Oic | B | 93 | 902.4 | 2.06 | A |
| 64 | Oic | B | 94 | 964.4 | 2.27 | A |
| 65 | Oic | B | 90 | 874.3 | 1.83 | A |
| 66 | Oic | B | 89 | 876.4 | 1.78 | A |
| 67 | Oic | B | 95 | 965.4 | 1.91 | A |
| 68 | Oic | B | 98 | 895.3 | 2.10 | A |
| 69 | Oic | B | 85 | 887.3 | 1.74 | A |
| 70 | Oic | B | 95 | 861.3 | 1.97 | A |
| 71 | Oic | d) | 83 | 932.4 | 1.69 | A |
| 72 | Oic | d) | >98 | 948.7 | 2.10 | A |
| 73 | Oic | d) | 81 | 933.4 | 2.08 | A |
| 74 | Oic | d) | 98 | 876.4 | 1.93 | A |
| 75 | Oic | d) | 98 | 934.5 | 2.02 | A |
| 76 | Oic | B/d) | 96 | 851.3 | 1.81 | A |
| 77 | Hyp(3CNBn) | d) | 90 | 909.4 | 1.83 | A |
| 78 | Oic | A | 86 | 818.4 | 1.76 | A |
| 79 | Oic | B | >98 | 819.5 | 2.07 | A |
| 80 | Oic | B | 96 | 833.4 | 2.16 | A |
| 81 | Oic | B | >98 | 853.0 | 2.13 | A |
| 82 | Oic | B | 97 | 805.3 | 2.00 | A |
| 83 | Oic | B | 94 | 862.3 | 1.79 | A |
| 84 | Oic | B | 98 | 833.3 | 2.19 | A |
| 85 | Oic | B | 97 | 833.3 | 2.13 | A |
| 86 | Oic | B | 98 | 869.3 | 2.02 | A |
| 87 | Oic | B | >98 | 823.3 | 1.74 | A |
| 88 | Oic | A | 95 | 849.3 | 1.93 | A |
| 89 | Oic | B | 93 | 865.3 | 1.96 | A |
| 90 | Oic | B | 94 | 901.3 | 1.85 | A |
| 91 | Oic | B | 98 | 885.3 | 2.03 | A |
| 92 | Oic | B | 94 | 957.4 | 2.00 | A |
| 93 | Oic | B | >98 | 834.3 | 1.82 | A |
| 94 | Oic | B | 95 | 860.3 | 1.90 | A |
| 95 | Oic | B | 95 | 860.3 | 1.90 | A |
| 96 | Oic | B | 94 | 874.4 | 1.92 | A |
| 97 | Oic | d) | 96 | 947.4 | 2.12 | A |
| 98 | Oic | d) | 98 | 945.4 | 2.08 | A |
| 99 | Oic | d) | 98 | 958.4 | 1.81 | A |
| 100 | Oic | d) | 91 | 910.3 | 2.08 | A |
| 101 | Oic | d) | 95 | 1015.4 | 2.28 | A |
| 102 | Oic | d) | 95 | 874.3 | 2.04 | A |
| 103 | Hyp | A | 97 | 794.4 | 1.59 | A |
| 104 | Oic | A | 98 | 818.4 | 1.84 | A |
| 105 | Oic | d) | 90 | 994.5 | 1.86 | A |
| 106 | Oic | d) | 97 | 912.4 | 2.17 | D |
| 107 | Oic | B | 94 | 861.4 | 1.95 | A |
| 108 | Oic | d) | 91 | 997.3 | 2.69 | D |
| 109 | Oic | B | 99 | 861.3 | 2.65 | D |
| 110 | Oic | B | 99 | 923.2 | 2.90 | D | a) Abbreviations of amino acid see listing above.
b) %-purity of compounds after prep. HPLC.
c) Double peak.
d) Post peptide sequence modifications.

2. Biological Methods

2.1 Preparation of the Peptide Samples.

Lyophilized peptides were weighed on a Microbalance (Mettler MX5) and dissolved in aqueous 90% DMSO to a final concentration of 10 mM unless otherwise stated. Stock solutions were kept at +4° C., and protected from light.

2.2 CCR10 Antagonism Assays

Peptides were assayed for CCR10 antagonism in a calcium flux assay and in a chemotaxis assay using a mouse pre-B cell line 300-19 stably transfected with human CCR10, and with human CCL27 as agonist.

Calcium Flux Assay

The calcium flux release was assessed using CCR10 transfected 300-19 murine pre-B cells. These cells were labeled as a batch with Calcium4 Reagent (Molecular Devices, Sunnyvale, Calif.) in HBSS buffer for 60 min.

After dispensing $8 \times 10^4$ cells in each well of a 384-well black plate, a concentrated solution of the β-hairpin peptidomimetics of this invention in HBSS+0.1% BSA+0.1% DMSO (final concentration) was added to the cells. The entire plate was centrifuged and placed in a Flexstation II (Molecular Devices) automated plate reader. After reading a 20 s baseline, the Flexstation dispensed CCL27 (RnD systems) at a final concentration of 30 nM in HBSS+0.1% BSA onto the cells and calcium flux was measured for an additional 70 s.

Alternatively a FlipR384 (Molecular Devices) was used for read out of the 384-well plates. In this case about $8 \times 10^4$ cells were placed in each well, centrifuged, placed in the FlipR and after 5 s of baseline reading, the β-hairpin peptidomimetics in HBSS+0.1% BSA+0.1% DMSO (final concentration) were added. After an incubation time of 5 min, the CCL27 solution was added to the mixture and the calcium flux was measured for 200 s.

The maximum signal was determined from control wells without inhibitor. Percentage of inhibition was calculated from a range of compound concentrations, which were subsequently used to calculate $IC_{50}$ values (Softmax Pro, Molecular Devices). All steps were carried out at room temperature.

Chemotaxis Assay

The chemotactic response of CCR10-transfected 300-19 murine pre-B cells to a gradient of CCL27 (CTACK) was measured using disposable Transwell® assay plates from Costar (5 µm pore size) according to the protocol of the manufacturer. Briefly, cells were grown under sterile conditions at 37° C. with 5% $CO_2$ in flasks containing RPMI+5% FCS, glutamine, penicillin/streptomycin (all media components were from Life Technologies) and the appropriate selection antibiotics (Puromycin, G418 or Tetracycline). For the assay, cells were pelleted by centrifugation, washed once in Dulbecco's phosphate buffered saline (DPBS), and resuspended to give $1 \times 10^6$ cells/ml in RPMI+0.5% bovine serum albumin (BSA). 100 µl of cell suspension was applied to the top of the assay filter. The β-hairpin peptidomimetics, diluted in the same assay medium, were added to both top and bottom chambers. The cells were allowed to migrate for 4-6 hours at 37° C. into the bottom chamber of the assay plate containing 30 nM of CCL27 (RnD systems). Migrated cells were counted using a FACS cytometer (Cytomics FC500, Beckman Coulter). Data normalization was performed using the number of any cells that had migrated in the absence of the β-hairpin peptidomimetic and the number of cells that have randomly migrated in absence of CCL27 [these values were taken as 100% (no inhibitory activity) and 0%, respectively]. From a range of compound concentrations $IC_{50}$ were determined using Prism5 (GraphPad software).

2.3 Results

TABLE 2

Biological Results

| Ex. | Sequence ID | $IC_{50}$ (nM) Calcium Flux Assay | $IC_{50}$ (nM) Chemotaxis Assay |
|---|---|---|---|
| 1 | SEQ ID NO: 1 | 225.8 ± 186.5 | 94.0 |
| 2 | SEQ ID NO: 2 | 199.9 ± 56.5 | 21.6 |
| 3 | SEQ ID NO: 3 | 78.5 ± 38.6 | nd |
| 4 | SEQ ID NO: 4 | 860.5 ± 381.8 | 42.0 |
| 5 | SEQ ID NO: 5 | 70.6 ± 20.1 | nd |
| 6 | SEQ ID NO: 6 | 133.7 ± 73.3 | 19.6 |
| 7 | SEQ ID NO: 7 | 144.5 ± 84.1 | 3.1 |
| 8 | SEQ ID NO: 8 | 52.5 ± 3.5 | nd |
| 9 | SEQ ID NO: 9 | 9.2 ± 3.6 | 2.0 |
| 10 | SEQ ID NO: 10 | 43.2 ± 44.9 | 9.7 |
| 11 | SEQ ID NO: 11 | 548.0 ± 82.5 | 11.6 |
| 12 | SEQ ID NO: 12 | 246.4 ± 79.0 | nd |
| 13 | SEQ ID NO: 13 | 26.0 ± 18.0 | 17.0 |
| 14 | SEQ ID NO: 14 | 70.5 ± 70.2 | nd |
| 15 | SEQ ID NO: 15 | 35.3 ± 14.3 | nd |
| 16 | SEQ ID NO: 16 | 40.4 ± 24.4 | 4.2 |
| 17 | SEQ ID NO: 17 | 44.3 ± 11.0 | nd |
| 18 | SEQ ID NO: 18 | 332.9 ± 149.0 | 3.1 |
| 20 | SEQ ID NO: 20 | 353.4 ± 282.8 | 1.7 |
| 21 | SEQ ID NO: 21 | 823.1 ± 407.5 | 21.9 |
| 22 | SEQ ID NO: 22 | 119.8 ± 63.6 | nd |
| 23 | SEQ ID NO: 23 | 214.3 ± 54.0 | 3.8 |
| 24 | SEQ ID NO: 24 | 283.3 ± 103.5 | 30.3 |
| 25 | SEQ ID NO: 25 | 70.4 ± 19.2 | nd |
| 26 | SEQ ID NO: 26 | 57.0 ± 26.4 | nd |
| 27 | SEQ ID NO: 27 | 242.8 ± 101.4 | nd |
| 28 | SEQ ID NO: 28 | 122.8 ± 86.3 | 29.0 |
| 29 | SEQ ID NO: 29 | 214.0 ± 105.9 | 109.0 |
| 30 | SEQ ID NO: 30 | 608.2 ± 188.5 | nd |
| 31 | SEQ ID NO: 31 | 131.9 ± 30.8 | nd |
| 32 | SEQ ID NO: 32 | 8.8 ± 5.0 | 12.0 |
| 33 | SEQ ID NO: 33 | 6.1 ± 0.8 | 2.7 |
| 34 | SEQ ID NO: 34 | 58.6 ± 5.7 | 38.7 |
| 36 | SEQ ID NO: 36 | 602.0 ± 96.2 | 208.5 |
| 37 | SEQ ID NO: 37 | 14.8 ± 12.0 | 22.0 |
| 38 | SEQ ID NO: 38 | 26.1 ± 8.1 | 2.3 |
| 39 | SEQ ID NO: 39 | 15.8 ± 10.3 | 9.0 |
| 40 | SEQ ID NO: 40 | 27.9 ± 10.5 | 3.8 |
| 41 | SEQ ID NO: 41 | 54.3 ± 22.0 | 140.0 |
| 42 | SEQ ID NO: 42 | 82.5 ± 30.4 | 14.2 |
| 43 | SEQ ID NO: 43 | 39.9 ± 34.8 | nd |
| 44 | SEQ ID NO: 44 | 1.9 ± 2.1 | 13.5 |
| 45 | SEQ ID NO: 45 | 65.8 ± 19.6 | 14.0 |
| 46 | SEQ ID NO: 46 | 12.6 ± 9.0 | 35.4 |
| 47 | SEQ ID NO: 47 | 21.7 ± 3.9 | nd |
| 48 | SEQ ID NO: 48 | 8.5 ± 3.5 | 8.6 |
| 49 | SEQ ID NO: 49 | 181.0 ± 109.6 | 5.3 |
| 50 | SEQ ID NO: 50 | 0.5 ± 0.2 | 1.8 |
| 51 | SEQ ID NO: 51 | 259.9 ± 153.7 | 60.1 |
| 52 | SEQ ID NO: 52 | 42.0 ± 25.1 | 37.0 |
| 53 | SEQ ID NO: 53 | 48.9 ± 40.0 | 143.0 |
| 54 | SEQ ID NO: 54 | 22.6 ± 13.6 | nd |
| 55 | SEQ ID NO: 55 | 5.3 ± 3.9 | 0.6 |
| 56 | SEQ ID NO: 56 | 11.6 ± 9.2 | 2.5 |
| 57 | SEQ ID NO: 57 | 149.9 ± 109.6 | 183.5 |
| 58 | SEQ ID NO: 58 | 11.6 ± 15.4 | 1.2 |
| 59 | SEQ ID NO: 59 | 25.0 ± 11.3 | 3.7 |
| 60 | SEQ ID NO: 60 | 54.9 ± 35.5 | 8.7 |
| 61 | SEQ ID NO: 61 | 25.1 ± 17.7 | 1.0 |
| 62 | SEQ ID NO: 62 | 12.0 ± 7.9 | 1.8 |
| 63 | SEQ ID NO: 63 | 28.0 ± 5.7 | 2.3 |
| 64 | SEQ ID NO: 64 | 3.0 ± 2.0 | 2.7 |
| 65 | SEQ ID NO: 65 | nd | 4.4 |
| 66 | SEQ ID NO: 66 | 333.0 ± 7.1 | 7.0 |
| 67 | SEQ ID NO: 67 | 49.5 ± 19.1 | 8.8 |
| 68 | SEQ ID NO: 68 | 4.8 ± 0.3 | 1.2 |
| 69 | SEQ ID NO: 69 | 1055.7 ± 106.8 | 16.4 |
| 70 | SEQ ID NO: 70 | 20.0 ± 4.2 | 4.7 |
| 71 | SEQ ID NO: 71 | 566.8 ± 154.8 | 50.2 |
| 72 | SEQ ID NO: 72 | 62.8 ± 41.6 | 11.5 |
| 73 | SEQ ID NO: 73 | 24.2 ± 24.5 | 5.3 |
| 74 | SEQ ID NO: 74 | 56.8 ± 99.8 | 6.9 |

TABLE 2-continued

Biological Results

| Ex. | Sequence ID | IC$_{50}$ (nM) Calcium Flux Assay | IC$_{50}$ (nM) Chemotaxis Assay |
|---|---|---|---|
| 75 | SEQ ID NO: 75 | 399.2 ± 178.4 | 15.2 |
| 76 | SEQ ID NO: 76 | 476.0 ± 70.7 | 14.7 |
| 77 | SEQ ID NO: 77 | 127.4 ± 73.0 | 50.7 |
| 78 | SEQ ID NO: 78 | 279.6 ± 193.4 | 48.0 |
| 79 | SEQ ID NO: 79 | 61.6 ± 30.9 | 1.4 |
| 80 | SEQ ID NO: 80 | 6.9 ± 12.3 | 9.6 |
| 81 | SEQ ID NO: 81 | 6.3 ± 2.0 | 5.0 |
| 82 | SEQ ID NO: 82 | 80.3 ± 64.6 | nd |
| 83 | SEQ ID NO: 83 | 106.7 ± 9.0 | 5.9 |
| 84 | SEQ ID NO: 84 | 46.4 ± 30.7 | 10.1 |
| 85 | SEQ ID NO: 85 | 20.4 ± 1.6 | 5.4 |
| 86 | SEQ ID NO: 86 | 8.1 ± 3.7 | 1.8 |
| 87 | SEQ ID NO: 87 | 516.5 ± 246.8 | 13.0 |
| 88 | SEQ ID NO: 88 | 220.2 ± 129.3 | 18.9 |
| 89 | SEQ ID NO: 89 | nd | 16.6 |
| 90 | SEQ ID NO: 90 | 48.9 ± 64.3 | 6.6 |
| 91 | SEQ ID NO: 91 | 1.1 ± 0.3 | 1.7 |
| 92 | SEQ ID NO: 92 | 16.7 ± 1.1 | 2.3 |
| 93 | SEQ ID NO: 93 | 145.8 ± 76.4 | 76.1 |
| 94 | SEQ ID NO: 94 | 392.7 ± 218.2 | 7.2 |
| 95 | SEQ ID NO: 95 | 262.0 ± 215.0 | 17.8 |
| 96 | SEQ ID NO: 96 | 706.0 ± 73.5 | 256.8 |
| 97 | SEQ ID NO: 97 | 8.1 ± 9.1 | 5.6 |
| 98 | SEQ ID NO: 98 | 3.0 ± 1.3 | 11.1 |
| 99 | SEQ ID NO: 99 | 53.9 ± 33.4 | 5.3 |
| 100 | SEQ ID NO: 100 | 0.2 ± 0.1 | 3.4 |
| 101 | SEQ ID NO: 101 | 6.4 ± 4.6 | nd |
| 102 | SEQ ID NO: 102 | 30.3 ± 23.1 | 4.8 |
| 103 | SEQ ID NO: 103 | 190.0 ± 89.8 | nd |
| 104 | SEQ ID NO: 104 | 52.7 ± 38.2 | nd |
| 105 | SEQ ID NO: 105 | 390.1 ± 228.0 | 1.2 |
| 106 | SEQ ID NO: 106 | 12.2 ± 3.8 | 4.8 |
| 107 | SEQ ID NO: 107 | 58.1 ± 33.9 | 13.4 |
| 108 | SEQ ID NO: 108 | 34.5 ± 17.3 | 2.5 |
| 109 | SEQ ID NO: 109 | 41.1 ± 9.7 | 3.2 |
| 110 | SEQ ID NO: 110 | 63.2 ± 25.6 | 2.7 | nd = not determined

The invention claimed is:

1. Compounds of the general formula (I)

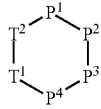

(I)

wherein the single elements T or P are connected in either direction from the carbonyl (C=O) point of attachment to the nitrogen (N) of the next element and wherein T$^1$ and T$^2$ are independently an L or D α-amino acid of one of the formulae

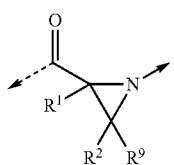

AA1

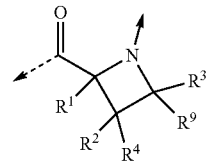

AA2

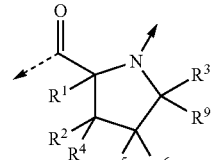

AA3

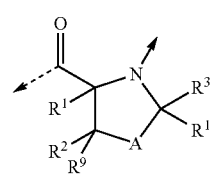

AA4

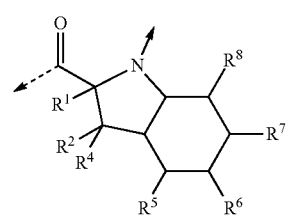

AA5

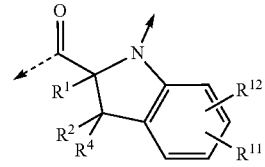

AA6

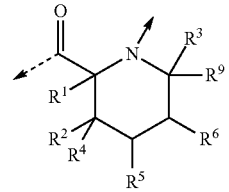

AA7

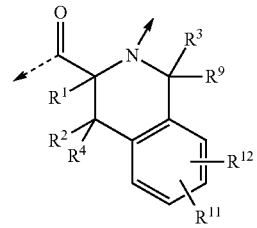

AA8

P$^1$ and P$^3$ are independently

—NR$^1$CH(R$^{19}$)CO—;

P$^2$ is —NR$^1$C(R$^{20}$)(R$^{21}$)CO—; or —NR$^1$C(Z)CO—;

P$^4$ is —NR$^1$CH(R$^{24}$)CO—;

A is O; NR$^9$; S; SO; or SO$_2$

R$^1$, R$^2$ and R$^3$ are independently

H; CF$_3$; lower alkyl; lower alkenyl; aryl-lower alkyl; or heteroaryl-lower alkyl;

$R^4$, $R^5$, $R^6$, $R^7$ and $R^8$ are independently

H; F; $CF_3$; lower alkyl; lower alkenyl; cycloalkyl; heterocycloalkyl; aryl; heteroaryl; aryl-lower alkyl; heteroaryl-lower alkyl; $-(CHR^{13})_oOR^{15}$; $-(CHR^{13})_o SR^{15}$; $-(CHR^{13})_oNR^{15}R^{16}$; $-(CHR^{13})_o OCONR^{15}R^{16}$; $-(CHR^{13})_oNR^1CONR^{15}R^{16}$; $-(CHR^{13})_oNR^1COR^{15}$; $-(CHR^{13})_oCOOR^{15}$; $-(CHR^{13})_oCONR^{15}R^{16}$; $-(CHR^{13})_oPO(OR^1)_2$; $-(CHR^{13})_oSO_2R^{15}$; $-(CHR^{13})_oNR^1SO_2R^{15}$; $-(CHR^{13})_oSO_2NR^{15}R^{16}$; $-(CR^{13})_oR^{30}$; or $-(CHR^1)_nO(CHR^2)_mR^{30}$; or $R^4$ and $R^2$ taken together can form:

=O; $-(CHR^{19})_p-$; $-(CH_2)_nO(CH_2)_m-$; $-(CH_2)_nS(CH_2)_m-$; or $-(CH_2)_nNR^1(CH_2)_m-$; or $R^4$ and $R^5$; $R^5$ and $R^6$; $R^6$ and $R^7$; $R^7$ and $R^8$; or $R^6$ and $R^9$ taken together can form:

$-(CHR^{19})_p-$; $-(CH_2)_nO(CH_2)_m-$; $-(CH_2)_nS(CH_2)_m-$; or $-(CH_2)_nNR^1(CH_2)_m-$;

$R^9$ and $R^{10}$ are independently

H; F; $CF_3$; lower alkyl; lower alkenyl; cycloalkyl; heterocycloalkyl; aryl; heteroaryl; aryl-lower alkyl; heteroaryl-lower alkyl; $-(CHR^{13})_rOR^{15}$; $-(CHR^{13})_r SR^{15}$; $-(CHR^{10})_rNR^{15}R^{16}$; $-(CHR^{13})_r OCONR^{15}R^{16}$; $-(CHR^{13})_rNR^1CONR^{15}R^{16}$; $-(CHR^{13})_rNR^1COR^{15}$; $-(CHR^{13})_rCOOR^{15}$; $-(CHR^{13})_rCONR^{15}R^{16}$; $-(CHR^{13})_rPO(OR^1)_2$; $-(CHR^{13})_rSO_2R^{15}$; $-(CHR^{13})_rNR^{15}SO_2R^{15}$; $-(CHR^{13})_rR^{13}SO_2NR^{15}R^{16}$; $-(CR^1R^{13})_oR^{30}$; or $-(CHR^1)_rO(CHR^1)_oR^{30}$;

$R^{11}$ and $R^{12}$ are independently

H; F; Cl; Br; $CF_3$; $OCF_3$; $OCHF_2$; CN; $NO_2$; lower alkyl; lower alkenyl; aryl; heteroaryl; aryl-lower alkyl; heteroaryl-lower alkyl; $-(CHR^{13})_oOR^{15}$; $-(CHR^{13})_o SR^{15}$; $-(CHR^{13})_oNR^{15}R^{16}$; $-(CHR^{13})_o OCONR^{15}R^{16}$; $-(CHR^{13})_oNR^1CONR^{15}R^{16}$; $-(CHR^{13})_oNR^1COR^{15}$; $-(CHR^{13})_oCOOR^{15}$; $-(CHR^{13})_oCONR^{15}R^{16}$; $-(CHR^{13})_oPO(OR^1)_2$; $-(CHR^{13})_oSO_2R^{15}$; $-(CHR^{13})_oNR^1SO_2R^{15}$; $-(CHR^{13})_oSO_2NR^{15}R^{16}$; or $-(CR^1R^{13})_oR^{30}$;

$R^{13}$ is H; F; $CF_3$; lower alkyl; lower alkenyl; cycloalkyl; heterocycloalkyl; cycloalkyl-lower alkyl; heterocycloalkyl-lower alkyl; aryl; heteroaryl; aryl-lower alkyl; heteroaryl-lower alkyl; $-(CHR^1)_oOR^{15}$; $-(CHR^1)_o SR^{15}$; $-(CHR^1)_oNR^{15}R^{16}$; $-(CHR^1)_oNC(=NR^{17})NR^{15}R^{16}$; $-(CHR^1)_oCOOR^{15}$; $-(CHR^1)_o CONR^{15}R^{16}$; $-(CHR^1)_oSO_2R^{15}$; or $-(CHR^1)_o SO_2NR^{15}R^{16}$;

$R^{14}$ is H; $CF_3$; lower alkyl; lower alkenyl; cycloalkyl; heterocycloalkyl; cycloalkyl-lower alkyl; heterocycloalkyl-lower alkyl; aryl; heteroaryl; aryl-lower alkyl; heteroaryl-lower alkyl; cycloalkyl-aryl; heterocycloalkyl-aryl; cycloalkyl-heteroaryl; heterocycloalkyl-heteroaryl; aryl-cycloalkyl; aryl-heterocycloalkyl; heteroaryl-cycloalkyl; heteroaryl-heterocycloalkyl; $-(CHR^1)_oOR^{15}$; $-(CHR^1)_oSR^{15}$; $-(CHR^1)_o NR^{15}R^{16}$; $-(CHR^1)_oCOOR^{15}$; $-(CHR^1)_o CONR^{15}R^{16}$; or $-(CHR^1)_oSO_2R^{15}$;

$R^{15}$, $R^{16}$, $R^{17}$ and $R^{18}$ are independently

H; lower alkyl; lower alkenyl; lower alkoxy; cycloalkyl; heterocycloalkyl; cycloalkyl-lower alkyl; heterocycloalkyl-lower alkyl; aryl; heteroaryl; aryl-lower alkyl; heteroaryl-lower alkyl; cycloalkyl-aryl; heterocycloalkyl-aryl; cycloalkyl-heteroaryl; heterocycloalkyl-heteroaryl; aryl-cycloalkyl; aryl-heterocycloalkyl; heteroaryl-cycloalkyl; or heteroaryl-heterocycloalkyl; or the structural elements $-NR^{15}R^{16}$ and $-NR^{17}R^{18}$ can independently form:

heterocycloalkyl; aryl-heterocycloalkyl; or heteroaryl-heterocycloalkyl;

or a group of one of the following formulae

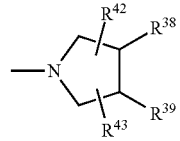

C1

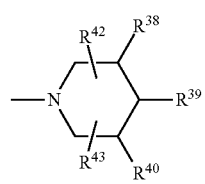

C2

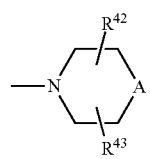

C3

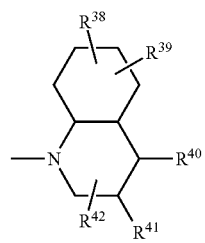

C4

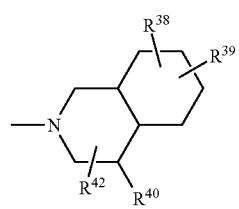

C5

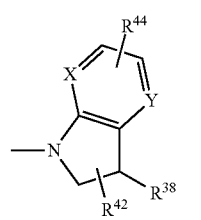

C6

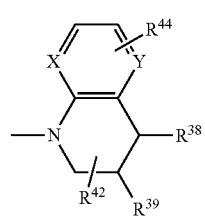

C7

-continued

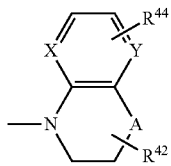
C8

X and Y are independently
—CR$^{45}$; or N;
R$^{19}$ is alkyl; alkenyl; cycloalkyl-lower alkyl; heterocycloalkyl-lower alkyl; —(CR$^1$R$^4$)$_n$R$^{30}$; —(CH$_2$)$_n$O (CH$_2$)$_m$R$^{30}$; —(CH$_2$)$_n$S(CH$_2$)$_m$R$^{30}$; or —(CH$_2$)$_n$NR$^{14}$ (CH$_2$)$_m$R$^{30}$;
R$^{20}$ and R$^{21}$ are independently
alkyl; alkenyl; —(CHR$^4$)$_o$OR$^{15}$; —(CHR$^4$)$_o$SR$^{15}$; or —(CHR$^4$)$_n$NR$^{15}$R$^{16}$;
Z is —(CR$^{22}$R$^{23}$)$_{(n+m+1)}$—; —(CR$^{22}$R$^{23}$)$_n$NR$^{15}$ (CR$^{22}$R$^{23}$)$_m$—; —(CR$^{22}$R$^{23}$)$_n$O(CR$^{22}$R$^{23}$)$_m$—; —(CR$^{22}$R$^{23}$)$_n$S(CR$^{22}$R$^{23}$)$_m$—; —O(CR$^{22}$R$^{23}$)$_r$O —;
or a group of one of the formulae

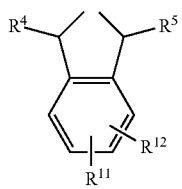
Z1

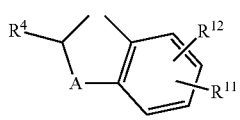
Z2

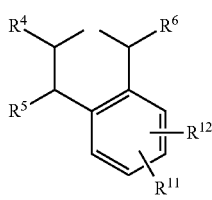
Z3

R$^{22}$ and R$^{23}$ are independently
H; F; CF$_3$; alkyl; alkenyl; cycloalkyl; heterocycloalkyl; aryl; heteroaryl; aryl-lower alkyl; or heteroaryl-lower alkyl; —(CR$^1$R$^{13}$)$_o$OR$^{15}$; —(CR$^1$R$^{13}$)$_o$SR$^{15}$; —(CR$^1$R$^{13}$)$_o$NR$^{15}$R$^{16}$; —(CR$^1$R$^{13}$)$_o$COOR$^{15}$R$^{16}$; —(CR$^1$R$^{13}$)$_o$CONR$^{15}$R$^{16}$; or —(CR$^1$R$^{13}$)$_o$SO$_2$R$^{15}$; or
R$^{22}$ and R$^{23}$ taken together can form:
=O; =NR$^1$; =NOR$^1$; =NOCF$_3$; —(CHR$^1$)$_p$—; or —O(CR$^1$R$^2$)$_r$O—;
R$^{24}$ is alkyl; alkenyl; —(CR$^1$R$^{13}$)$_q$NR$^{15}$R$^{16}$; —(CR$^1$R$^{13}$)$_q$NR$^{25}$R$^{26}$; —(CR$^1$R$^{13}$)$_q$NR$^{14}$R$^{27}$; —(CH$_2$)$_q$C(=NR$^{13}$) NR$^{15}$R$^{16}$; —(CH$_2$)$_q$C(=NOR$^{17}$)NR$^{15}$R$^{16}$; —(CH$_2$)$_q$C (=NNR$^{15}$R$^{16}$)NR$^{17}$R$^{18}$; —(CR$^1$R$^{13}$)$_q$NR$^2$C(=NR$^{17}$) NR$^{15}$R$^{16}$; —(CR$^1$R$^{13}$)$_q$N=C(NR$^{15}$R$^{16}$)NR$^{17}$R$^{18}$; —(CR$^1$R$^{13}$)$_q$OR$^{14}$; —(CR$^1$R$^{13}$OR$^{25}$; —(CR$^1$R$^{13}$)$_q$ OR$^{27}$; —(CR$^1$R$^{13}$)$_q$SR$^{15}$; —(CR$^1$R$^{13}$)$_q$SO$_2$R$^{15}$; —(CR$^1$R$^{13}$)$_q$NR$^{14}$SO$_2$R$^{15}$; —(CR$^1$R$^{13}$)$_q$SO$_2$NR$^1$R$^{14}$; —(CR$^1$R$^{13}$)$_q$NR$^{14}$SO$_2$NR$^{15}$R$^{16}$; —(CR$^1$R$^{13}$)$_q$ SO$_2$NR$^{15}$R$^{16}$; —(CR$^1$R$^{13}$)$_q$PO(OR$^1$)$_2$; —(CH$_2$)$_n$O (CH$_2$)$_m$NR$^{15}$R$^{16}$; —(CH$_2$)$_n$O(CH$_2$)$_m$C(=NR$^{17}$) NR$^{15}$R$^{16}$; —(CH$_2$)$_n$O(CH$_2$)$_m$C(=NOR$^{17}$)NR$^{15}$R$^{16}$; —(CH$_2$)$_n$O(CH$_2$)$_m$C(=NNR$^{15}$R$^{16}$)NR$^{17}$R$^{18}$; —(CH$_2$)$_n$O(CH$_2$)$_m$NR$^1$C(=NR$^{17}$)NR$^{15}$R$^{16}$; —(CH$_2$)$_n$O(CH$_2$)$_m$N=C(NR$^{15}$R$^{16}$)NR$^{17}$R$^{18}$; —(CH$_2$)$_n$S(CH$_2$)$_m$NR$^{15}$R$^{16}$; —(CH$_2$)$_n$S(CH$_2$)$_m$C(=NR$^{17}$)NR$^{15}$R$^{16}$; —(CH$_2$)$_n$S(CH$_2$)$_m$C(=NOR$^{17}$)NR$^{15}$R$^{16}$; —(CH$_2$)$_n$S (CH$_2$)$_m$C(=NNR$^{15}$R$^{16}$)NR$^{17}$R$^{18}$; —(CH$_2$)$_n$S(CH$_2$)$_m$ NR$^1$C(=NR$^{17}$)NR$^{15}$R$^{16}$; —(CH$_2$)$_n$S(CH$_2$)$_m$N=C (NR$^{15}$R$^{16}$)NR$^{17}$R$^{18}$; —(CR$^1$R$^{13}$)$_q$COOR$^{15}$; —(CR$^1$R$^{13}$)$_q$COOR$^{25}$; —(CR$^1$R$^{13}$)$_q$COOR$^{28}$; —(CR$^1$R$^{13}$)$_q$CONR$^{15}$R$^{16}$; or —(CR$^1$R$^{13}$)$_q$ CONR$^{25}$R$^{26}$;
or alternatively heteroaryl; or heteroarylalkyl;
R$^{25}$ and R$^{26}$ are independently
H; —CH$_3$; —[(CH$_2$)$_2$O]$_r$CH$_3$; or —[(CH$_2$)$_2$O]$_r$CF$_3$
R$^{27}$ is —COR$^{19}$; —CO(CR$^1$R$^{13}$)$_o$R$^{15}$; —CO(CR$^1$R$^{13}$)$_o$ OR$^{14}$; —CO(CR$^1$R$^{13}$)$_o$NR$^{15}$R$^{16}$; —CO(CR$^1$R$^{13}$)$_o$ NR$^2$R$^{14}$; —CO(CR$^1$R$^{19}$)NR$^{15}$R$^{16}$; —CO(CR$^1$R$^{29}$) NR$^{15}$R$^{16}$; —CO(CHR$^1$)$_o$CONR$^{15}$R$^{16}$; —CO(CHR$^1$)$_o$ CONR$^2$SO$_2$R$^{15}$; —CO(CR$^1$R$^{13}$)$_o$NR$^2$SO$_2$R$^{15}$; —CONR$^1$(CHR$^{15}$)$_n$NR$^2$(CHR$^{13}$)$_m$R$^{14}$; —CO (CHR$^{15}$)$_n$O(CHR$^{13}$)$_m$R$^{14}$; —CONR$^1$(CHR$^{15}$)$_n$O (CHR$^{13}$)$_m$R$^{14}$; —SO$_2$R$^{19}$; —SO$_2$(CR$^1$R$^{13}$)$_o$R$^{15}$; —SO$_2$(CR$^1$R$^{13}$)$_o$NR$^{15}$R$^{16}$; or —SO$_2$(CR$^1$R$^{13}$)$_o$ NR$^1$R$^{25}$;
R$^{28}$ is —NR$^1$C(R$^2$)(R$^{19}$)COOR$^{15}$; —NR$^1$C(R$^2$)(R$^{19}$) CONR$^{15}$R$^{16}$; —NR$^1$C(R$^2$)(R$^{29}$)COOR$^{15}$; —NR$^1$C(R$^2$) (R$^{29}$)CONR$^{15}$R$^{16}$;
R$^{29}$ is —(CR$^1$R$^{13}$)$_1$NR$^{15}$R$^{16}$; —(CH$_2$)$_q$C(=NR$^{17}$) NR$^{15}$R$^{16}$; —(CH$_2$)$_q$C(=NOR$^{17}$)NR$^{15}$R$^{16}$; —(CH$_2$)$_q$C (=NNR$^{15}$R$^{16}$)NR$^{17}$R$^{18}$; —(CR$^1$R$^{13}$)$_q$NR$^2$C(=NR$^{16}$) NR$^{14}$R$^{15}$; —(CR$^1$R$^{13}$)$_q$N=C(NR$^{15}$R$^{16}$)NR$^{17}$R$^{18}$; —(CR$^1$R$^{13}$)$_q$OR$^{14}$; —(CR$^1$R$^{13}$)$_q$SR$^{15}$; —(CR$^1$R$^{13}$)$_q$ SO$_2$R$^{15}$; —(CR$^1$R$^{13}$)$_q$NR$^{14}$SO$_2$R$^{15}$; —(CR$^1$R$^{13}$)$_q$ SO$_2$NR$^1$R$^{14}$; —(CR$^1$R$^{13}$SO$_2$NR$^{15}$R$^{16}$; —(CR$^1$R$^{13}$)$_q$ NR$^2$SO$_2$NR$^{15}$R$^{16}$; —(CR$^1$R$^{13}$)$_q$PO(OR$^1$)$_2$; —(CH$_2$)$_n$O (CH$_2$)$_m$NR$^{15}$R$^{16}$; —(CH$_2$)$_n$O(CH$_2$)$_m$C(=NR$^{17}$) NR$^{15}$R$^{16}$; —(CH$_2$)$_n$O(CH$_2$)$_m$C(=NOR$^{17}$)NR$^{15}$R$^{16}$; —(CH$_2$)$_n$O(CH$_2$)$_m$C(=NNR$^{15}$R$^{16}$)NR$^{17}$R$^{18}$; —(CH$_2$)$_n$O(CH$_2$)$_m$NR$^{14}$C(=NR$^{17}$)NR$^{15}$R$^{16}$; —(CH$_2$)$_n$O(CH$_2$)$_m$N=C(NR$^{15}$R$^{16}$)NR$^{17}$R$^{18}$; —(CH$_2$)$_n$S(CH$_2$)$_m$NR$^{15}$R$^{16}$; —(CH$_2$)$_n$S(CH$_2$)$_m$ NR$^{15}$R$^{16}$; —(CH$_2$)S(CH$_2$)$_m$C(=NR$^{17}$)NR$^{15}$R$^{16}$; —(CH$_2$)$_n$S(CH$_2$)$_m$C(=NOR$^{17}$)NR$^{15}$R$^{16}$; —(CH$_2$)$_n$S (CH$_2$)$_m$C(=NNR$^{15}$R$^{16}$)NR$^{17}$R$^{18}$; —(CH$_2$)$_n$S(CH$_2$)$_m$ NR$^{14}$C(=NR$^{17}$)NR$^{15}$R$^{16}$; —(CH$_2$)$_n$S(CH$_2$)$_m$N=C (NR$^{15}$R$^{16}$)NR$^{17}$R$^{18}$; —(CR$^1$R$^{13}$)$_q$COOR$^{15}$; or —(CR$^1$R$^{13}$)$_q$CONR$^{15}$R$^{16}$;
R$^{30}$ is an aryl group of one of the formulae

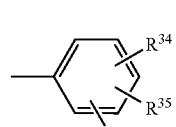
AR1

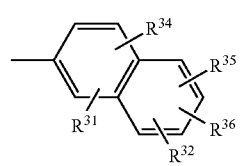
AR2

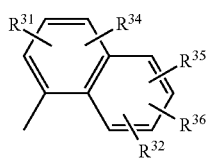
or a heteroaryl group of one of the formulae
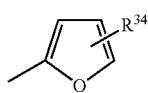 H1
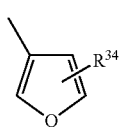 H2
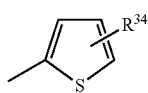 H3
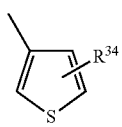 H4
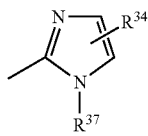 H5
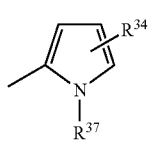 H6
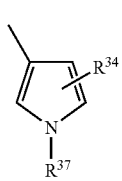 H7
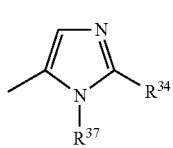 H8
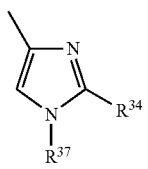 H9
AR3
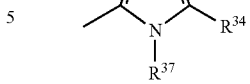 H10
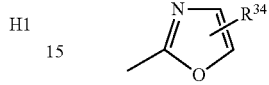 H11
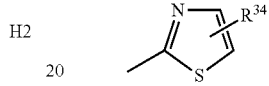 H12
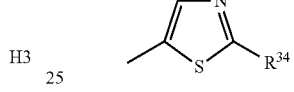 H13
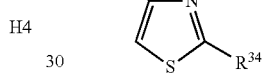 H14
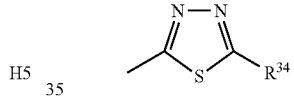 H15
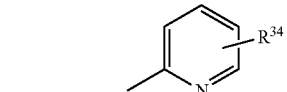 H16
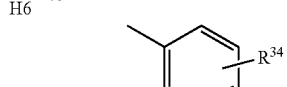 H17
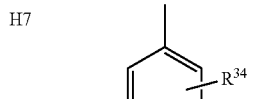 H18
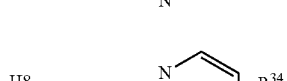 H19
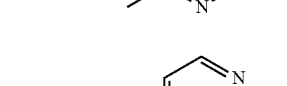 H20
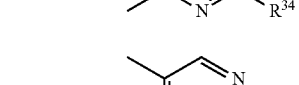 H21
 H22

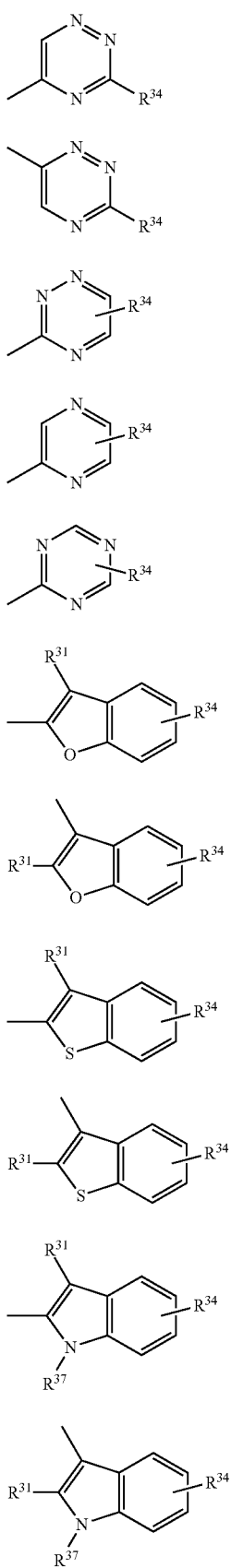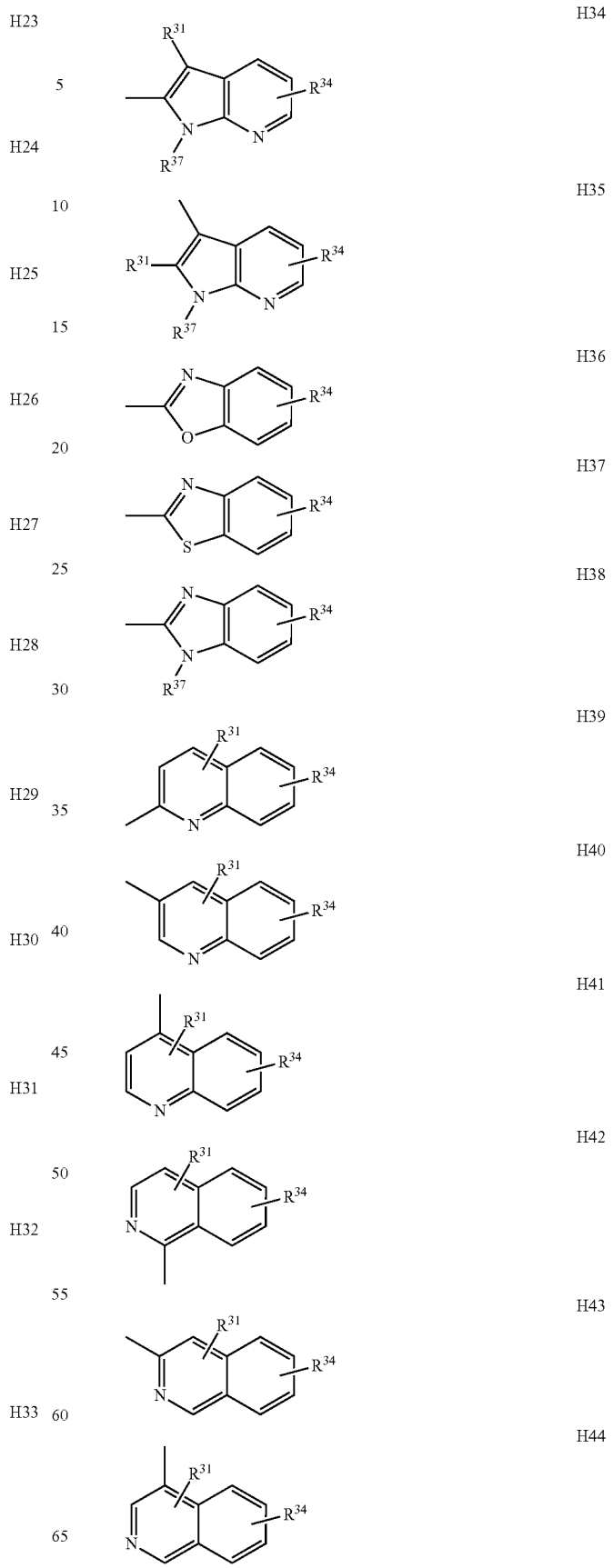

-continued

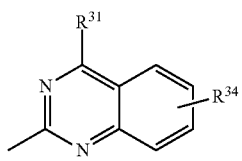
H45

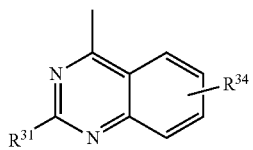
H46

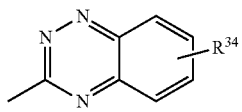
H47

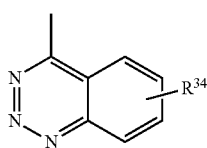
H48

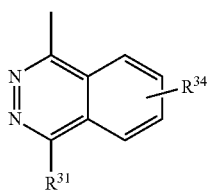
H49

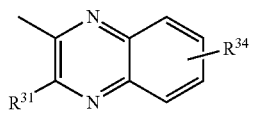
H50

$R^{31}$ and $R^{32}$ are independently
H; F; Cl; Br; $NO_2$; CN; $CF_3$; $OCHF_2$; $OCF_3$; lower alkyl; lower alkenyl; aryl-lower alkyl; aryl; heteroaryl; —$(CH_2)_oR^{33}$; —$(CH_2)_oOR^{15}$; —$O(CH_2)_oR^{33}$; —$(CH_2)_oSR^{15}$; —$(CH_2)_oNR^{15}R^{16}$; —$(CH_2)_o$CONR$^{15}R^{16}$; —$(CH_2)_oNR^1CONR^{15}R^{16}$; —$(CH_2)_o$NR$^1COR^{15}$; —$(CH_2)_oCOOR^{15}$; —$(CH_2)_o$CONR$^{15}R^{16}$; —$(CH_2)_oPO\ (OR^1)_2$; —$(CH_2)_o$SO$_2R^{14}$; or —$(CH_2)_oCOR^{15}$;

$R^{33}$ is an aryl group of the formula

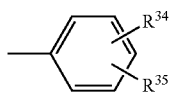
AR4

$R^{34}$, $R^{35}$ and $R^{36}$ are independently
H; F; Cl; Br; OH; $NH_2$; $NO_2$; CN; $CF_3$; $OCHF_2$; $OCF_3$; —$NR^1R^{15}$; —$(CH_2)_oCOOR^{15}$; —$(CH_2)_o$CONR$^1R^{15}$; lower alkyl; lower alkoxy; or lower alkenyl;

$R^{37}$ is H; lower alkyl; or aryl-lower alkyl;
$R^{38}$, $R^{39}$, $R^{40}$ and $R^{41}$ are independently
H; F; $CF_3$; lower alkyl; lower alkenyl; cycloalkyl; heterocycloalkyl; aryl; heteroaryl; aryl-lower alkyl; heteroaryl-lower alkyl; —$(CHR^1)_oOR^{15}$; —$(CHR^1)_o$ $SR^{15}$; —$(CHR^1)_oNR^2R^{15}$; —$(CHR^1)_oOCONR^2R^{15}$; —$(CHR^1)_oNR^2CONR^3R^{15}$; —$(CHR^1)_oNR^2COR^{15}$; —$(CHR^1)_oCOOR^{15}$; —$(CHR^1)_oCONR^2R^{15}$; —$(CHR^1)_oPO(OR^2)_2$; —$(CHR^1)_oSO_2R^{15}$; —$(CHR^1)_oNR^2SO_2R^{15}$; —$(CHR^1)_oSO_2NR^2R^{15}$; —$(CR^1R^2)_oR^{33}$; or —$(CHR^1)_nO(CHR^2)_mR^{33}$;

$R^{42}$ and $R^{43}$ are independently
H; F; $CF_3$; lower alkyl; lower alkenyl; cycloalkyl; heterocycloalkyl; aryl; heteroaryl; aryl-lower alkyl; heteroaryl-lower alkyl; —$(CHR^1)_rOR^{15}$; —$(CHR^1)_r$ $SR^{15}$; —$(CHR^1)_rNR^2R^{15}$; —$(CHR^1)_rOCONR^2R^{15}$; —$(CHR^1)_rNR^2CONR^3R^{15}$; —$(CHR^1)_rNR^2COR^{15}$; —$(CHR^1)_oCOOR^{15}$; —$(CHR^1)_oCONR^2R^{15}$; —$(CHR_1)_rPO(OR^2)_2$; $(CHR^1)_rSO_2R^{15}$; —$(CHR^1)_r$ $NR^2SO_2R^{15}$; —$(CHR^1)_rSO_2NR^2R^{15}$; —$(CR^1R^2)_o$ $R^{33}$; or —$(CHR^1)_oO(CHR^2)_oR^{33}$;

$R^{44}$ and $R^{45}$ are independently
H; F; Cl; Br; $CF_3$; $OCF_3$; $OCHF_2$; CN; $NO_2$; lower alkyl; lower alkenyl; aryl; heteroaryl; aryl-lower alkyl; heteroaryl-lower alkyl; —$(CHR^1)_oOR^{15}$; —$(CHR^1)_o$ $SR^{15}$; —$(CHR^1)_oNR^2R^{15}$; —$(CHR^1)_oOCONR^2R^{15}$; —$(CHR^1)_oNR^2CONR^3R^{15}$; —$(CHR)_oNR^2COR^{15}$; —$(CHR^1)_oCOOR^{15}$; —$(CHR^1)_oCONR^2R^{15}$; —$(CHR^1)_oPO(OR^2)_2$; —$(CHR^1)_oSO_2R^{15}$; —$(CHR^1)_oNR^2SO_2R^{15}$; —$(CHR^1)_oSO_2NR^2R^{15}$; or —$(CR^1R^2)_oR^{33}$;

n and m are independently an integer of 0-5 with the proviso that n+m ≤6;
o is 0-4; p is 2-6; q is 1-6; r is 1-3;
or pharmaceutically acceptable salts thereof.

2. Compounds according to claim 1 wherein $R^{24}$ is other than heteroaryl or heteroarylalkyl.

3. Compounds according to claim 1 or 2 wherein
$T^1$ is $^DPro$; $^DPip$; $^DAze$;
$T^2$ is an L or D α-amino acid of one of the formulae

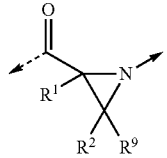
AA1

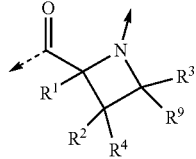
AA2

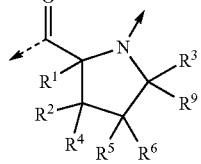
AA3

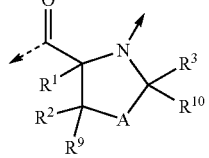
AA4

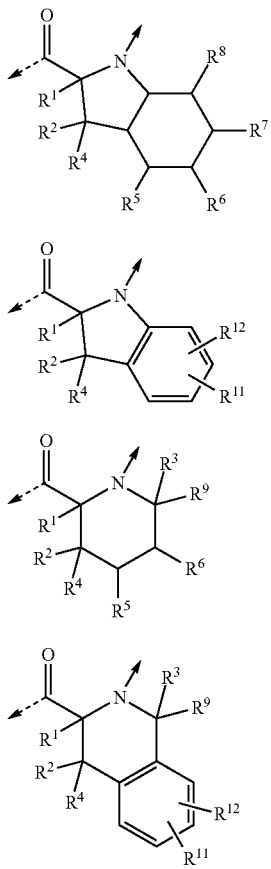

AA5

AA6

AA7

AA8

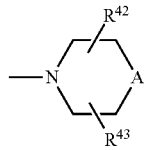

C3

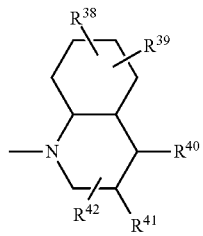

C4

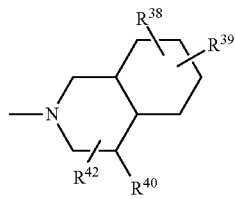

C5

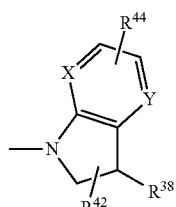

C6

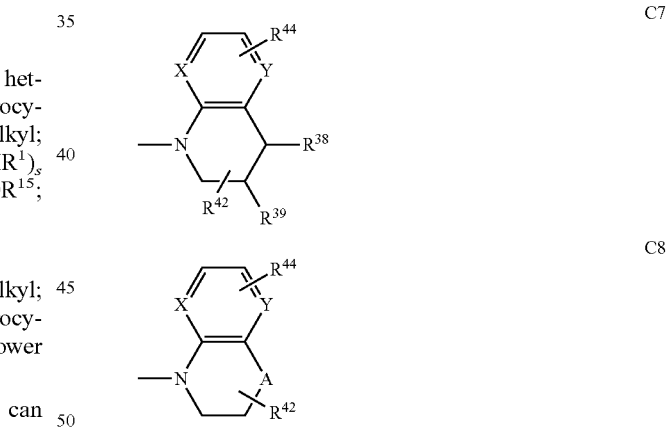

C7

C8

$R^{14}$ is H; $CF_3$; lower alkyl; lower alkenyl; cycloalkyl; heterocycloalkyl; cycloalkyl-lower alkyl; heterocycloalkyl-lower alkyl; aryl; heteroaryl; aryl-lower alkyl; heteroaryl-lower alkyl; —$(CHR^1)_sOR^{15}$; —$(CHR^1)_sSR^{15}$; —$(CHR^1)_sNR^{15}R^{16}$; —$(CHR^1)_oCOOR^{15}$; —$(CHR^1)_oCONR^{15}R^{16}$;or —$(CHR^1)_oSO_2R^{15}$;

$R^{15}$, $R^{16}$, $R^{17}$ and $R^{18}$ are indepentently

H; lower alkyl; lower alkenyl; lower alkoxy; cycloalkyl; heterocycloalkyl; cycloalkyl-lower alkyl; heterocycloalkyl-lower alkyl; aryl; heteroaryl; aryl-lower alkyl; or heteroaryl-lower alkyl; or the structural elements —$NR^{15}R^{16}$ and —$NR^{17}R^{18}$ can independently form a group of one of the formulae

C1

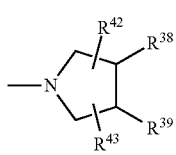

C2

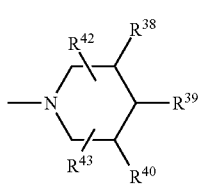

$R^{24}$ is alkyl; alkenyl; —$(CR^1R^{13})_qNR^{15}R^{16}$; —$(CR^1R^{13})_q$ $NR^{25}R^{26}$; —$(CR^1R^{13})_qNR^{14}R^{27}$; —$(CH_2)_qC(=NR^{17})$ $NR^{15}R^{16}$; —$(CR^1R^{13})_qNR^2C(=NR^{17})NR^{15}R^{16}$; —$(CR^1R^{13})_qOR^{15}$; —$(CR^1R^{13})_qOR^{25}$; —$(CR^1R^{13})_q$ $OR^{27}$; —$(CR^1R^{13})_qSR^{15}$; —$(CR^1R^{13})_qSO_2R^{15}$; —$(CR^1R^{13})_qNR^{15}SO_2R^{16}$; —$(CR^1R^{13})_qSO_2NR^1R^{14}$; —$(CR^1R^{13})_qSO_2NR^{15}R^{16}$; —$(CH_2)_qO(CH_2)_m$ $NR^{15}R^{16}$; —$(CH_2)_nO(CH_2)_mC(=NR^{17})NR^{15}R^{16}$; —$(CH_2)_nO(CH_2)_mNR^1C(=NR^{17})NR^{15}R^{16}$; —$(CH_2)_m$ $O(CH_2)_mN=C(NR^{15}R^{16})NR^{17}R^{18}$; —$(CH_2)_nS(CH_2)_m$ $NR^{15}R^{16}$; —$(CR^1R^{13})_qCOOR^{15}$; —$(CR^1R^{13})_q$ $COOR^{25}$; —$(CR^1R^{13})_qCOOR^{28}$; —$(CR^1R^{13})_q$ $CONR^{15}R^{16}$; or —$(CR^1R^{13})_qCONR^{25}R^{26}$;

or alternatively heteroaryl; or heteroarylalkyl;

s is 2-4 or pharmaceutically acceptable salts thereof.

4. Compounds according to claim 3 wherein

T¹ is ᴰPro; ᴰPip; or ᴰAze;

T² is an L or D α-amino acid of one of the formulae

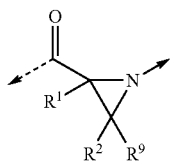
AA1

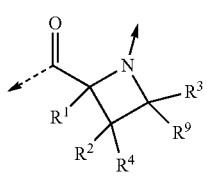
AA2

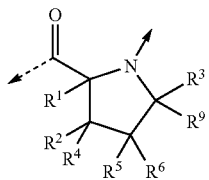
AA3

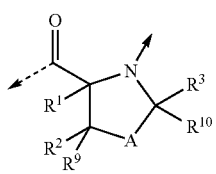
AA4

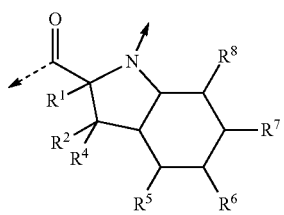
AA5

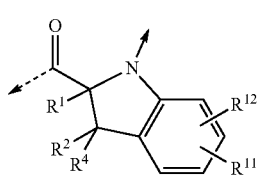
AA6

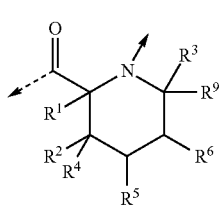
AA7

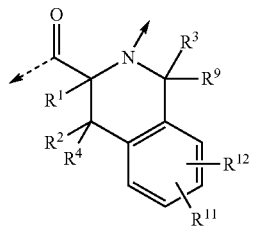
AA8

P¹ and P³ are independently
His; His(Me); His(Bn); hHis; Phe; Phe(2Cl); Phe(3Cl); Phe(4Cl); Phe(3,4Cl₂); Phe(2F); Phe(3F); Phe(4F); Phe(3,⁴F₂); Phe(3CN); Phe(4CN); Phe(2CF₃); Phe(3CF₃); Phe(4CF₃); Phe(3,4(CF₃)₂); Phe(4COOMe); hPhe; Thi; Tza; Trp; Trp(5OH); Trp(5Cl); Trp(6Cl); Trp(5,6Cl₂); Trp(5Br); Trp(6Br); Trp(6CF₃); Trp(7Aza); hTrp; Tyr; Tyr(Me); Tyr(Ph); Tyr(Bn); Tyr(4OHPh); Tyr(4MeOCOBn); hTyr; Thr(Bn); Ser(Bn); 2Pal; 3Pal; 4Pal; Phg; Ala(2Furyl); Ala(3Furyl); Ala(2Quin); Ala(3Quin); Ala(4Quin); Ala(tBu); Gly(tBu); 1Nal; 2Nal; Nle(6OBn); Cha; hCha; Bip; Bbta; or OctG;

P² is Aib; Ac3c; Ac4c; Cyp; Chx; Chx(4oxo); Ac7c; Ac8c; ᴰAtc; ᴸAtc; ᴰᴸAtc; Deg; or 4,4-AC-ThioTHP;

P⁴ is Arg; hArg; Ala (Ppz); Thr; alloThr; Gln; Gln(Me); Gln(Me₂); Gln(iPr); Gln(cPr); Gln(iBu); Glu(Ala); Glu(ᴰAla); Glu(Arg); Glu(ᴰArg); Glu(Glu); Glu(Gly); Glu(His); Glu(Leu); Glu(ᴰLeu); Glu(2Nal); Glu(Sar); Glu(Trp); Glu(ᴰTrp); Cys; hCys; Ser; hSer; Ser(Me); hSer(Me); Thr; Met; Met(O₂); Lys; hLys; Lys(Ac); Lys(Me); Lys(Bz); Lys(Nic); Lys(4Oxa); Lys((5R)OH); Orn; Dap; Dap(MeO(CH₂)₂); Dap(CONH₂); Dap((MeO(CH₂)₂)₂); Dab(Sar); Dab; Dab(Ac); Dab(Ala); Dab(ᴰAla); Dab(Arg); Dab(ᴰArg); Dab(Dab); Dab(Glu); Dab(Gly); Dab(His); Dab(Leu); Dab(ᴰLeu); Dab(MEMCO); Dab(4Me₂NPhSO₂); Dab(MeO(CH₂)₂NHCO); Dab((MeO(CH₂)₂)(Me)NCO); Dab(MePpzCO); Dab(MeSO₂); Dab(morphCO); Dab(2Na1); Dab(Trp); Dab(ᴰTrp); Dab(Sar); Gln(Alk1); Gln(Alk2); Gln(Alk3); Gln(Alk4); Gln(Alk5); Gln(Alk6); Gln(Alk7); Gln(Alk8); Gln(Alk9); Gln(Alk10); Gln(Alk11); Gln(Alk12); Gln(Alk13); Gln(Alk14); Gln(Alk15); Gln(Alk16); Gln(Alk17); Gln(Alk18); Gln(Alk19); Gln(Alk20); Gln(Alk21); Gln(Alk22); Gln(Alk23); Gln(Alk24); Gln(Alk25); Gln(Alk26); Gln(Alk27); Gln(Alk28); Gln(Alk29); Gln(Alk30); Gln(Alk31); Gln(Alk32); Gln(Alk33); Gln(Alk34); Glu(cN1); Glu(cN2); Glu(cN3); Glu(cN4); Glu(cN5); Glu(cN6); Glu(cN7); Glu(cN8); Glu(cN9); Glu(cN 10); Glu(cN11); Glu(cN 12); Glu(cN 13); Glu(cN 14); Glu(cN 15); Glu(cN 16); Glu(cN17); Sab(N1); Sab(N2); Sab(N3); Sab(N4); Sab(N5); Sab(N6); Sab(N7); Sab(N8); Sab(N9); Sab(N10); Sab(N11); Sab(N12); Sab(N13); Sab(N14); Sab(N15); Sab(N16); Sab(N17); Sab(N18); Sab(N19); Sab(N20); Sab(N21); Sab(N22); Sab(N23); Sab(N24); Sab(N25); Sab(N26); Sab(N27); Sab(N28); Sab(N29); Sab(N30); Sab(N31); Sab(N32); Sab(N33); Sab(N34); Sab(N35); Sab(N36); Sab(N37); Sab(N38); Sab(N39); Sab(N40); Sab(N41); Sab(N42); Sab(N43); Sab(N44); Sab(N45); Sab(N46); Sab(N47); Sab(N48); Sab(N49); Sab(N50); Sab(N51); Sab(N52); Sab(N53); Sab(N54); Sab(N55); Sab(N56); Sab(N57); Sab(N58); Sab(N59); Sab(N60); Sab(N61); Dab(SN1); Dab(SN2); Dab(SN3); Dab(SN4); Dab(SN5); Dab(SN6); Dab (SN7); Dab(SN8); Dab(SN9); Dab(SN10); Dab(SN11); Dab(SN12); Dab(SN13); Dab(SN14); Dab(SN15); Dab(SN16); Dab(SN17); Dab(SN18); Dab(SN19); Dab(SN20); Dab(SN21); Dab(SN22); Dab(SN23); Dab(SN24); Dab(SN25); Dab(SN26); Dab(SN27); Dab(SN28); Dab(SN29); Dab(SN30); Dab(SN31); Dab(SN32); Dab(SN33); Dab(SN34); Dab(SN35); Dab(SN36); Dab(SN37); Dab(SN38); Dab(SN39); Dab(SN40); Dab(SN41); Dab(SN42); Dab(SN43); Dab(SN44); Dab(SN45); Dab(SN46); Dab(SN47); Dab(SN48); Dab(SN49); Dab(SN50); Dab(SN51); Dab(SN52); Dab(SN53); Dab(SN54); Dab(SN55); Dab(SN56); Dab(SN57); Dab(SN58); Dab(SN59); Dab(SN60); Dab(SN61); Dab(UN1); Dab(UN2); Dab(UN3); Dab(UN4); Dab(UN5); Dab(UN6); Dab(UN7); Dab(UN8); Dab(UN9); Dab(UN10); Dab(UN11); Dab(UN12); Dab(UN13); Dab(UN14); Dab(UN15); Dab(UN16); Dab(UN17); Dab(UN18); Dab(UN19); Dab(UN20); Dab(UN21); Dab(UN22); Dab(UN23); Dab(UN24); Dab(UN25); Dab(UN26); Dab(UN27); Dab(UN28); Dab(UN29); Dab(UN30); Dab(UN31); Dab(UN32); Dab(UN33); Dab(UN34); Dab(UN35); Dab(UN36); Dab(UN37); Dab(UN38); Dab(UN39); Dab(UN40); Dab(UN41); Dab(UN42); Dab(UN43); Dab(UN44); Dab(UN45); Dab(UN46); Dab(UN47); Dab(UN48); Dab(UN49); Dab(UN50); Dab(UN51); Dab(UN52); Dab(UN53); Dab(UN54); Dab(UN55); Dab(UN56); Dab(UN57); Dab(UN58); Dab(UN59); Dab(UN60); Dab(UN61); Dab(S1); Dab(S2); Dab(S3); Dab(S4); Dab(S5); Dab(S6); Dab(S7); Dab(S8); Dab(S9); Dab(S10); Dab(S11); Dab(S12); Dab(S13); Dab(S14); Dab(S15); Dab(S16); Dab(S17); Dab(S18); Dab(A1); Dab(A2); Dab(A3); Dab(A4); Dab(A5); Dab(A6); Dab(A7); Dab(A8); Dab(A9); Dab(A10); Dab(A11); Dab(A12); Dab(A13); Dab(A14); Dab(A15); Dab(A16); Dab(A17); Dab(A18); Dab(A19); Dab(A20); Dab(A21); Dab(A22); Dab(A23); Dab(A24); Dab(A25); Dab(A26); Dab(A27); Dab(A28); Dab(A29); Dab(A30); Dab(A31); Dab(A32); Dab(A33); Dab(A34); Dab(A35); Dab(A36); Dab(A37); Dab(A38); Dab(A39); Dab(A40); Dab(A41); Dab(A42); Dab(A43); Dab(A44); Dab(A45); Dab(A46); Dab(A47); Dab(A48); Dab(A49); Dab(A50); Dab(A51); Dab(A52); Dab(A53); Dab(A54); Dab(A55); Dab(A56); Dab(Suc1); Dab(Suc2); Dab(Suc3); Dab(Suc4); Dab(Suc5); Dab(Suc6); Dab(Suc7); Dab(Suc8); Dab(Suc9); Dab(Suc10); Asn(Alk1); Asn(Alk2); Asn(Alk3); Asn(Alk4); Asn(Alk5); Asn(Alk6); Asn(Alk7); Asn(Alk8); Asn(Alk9); Asn(Alk10); Asn(Alk11); Asn(Alk12); Asn(Alk13); Asn(Alk14); Asn(Alk15); Asn(Alk16); Asn(Alk17); Asn(Alk18); Asn(Alk19); Asn(Alk20); Asn(Alk21); Asn(Alk22); Asn(Alk23); Asn(Alk24); Asn(Alk25); Asn(Alk26); Asn(Alk27); Asn(Alk28); Asn(Alk29); Asn(Alk30); Asn(Alk31); Asn(Alk32); Asn(Alk33); Asn(Alk34); Asp(cN1); Asp(cN2); Asp(cN3); Asp(cN4); Asp(cN5); Asp(cN6); Asp(cN7); Asp(cN8); Asp(cN9); Asp(cN10); Asp(cN11); Asp(cN12); Asp(cN13); Asp(cN14); Asp(cN15); Asp(cN16); Asp(cN17); Sap(N1); Sap(N2); Sap(N3); Sap(N4); Sap(N5); Sap(N6); Sap(N7); Sap(N8); Sap(N9); Sap(N10); Sap(N11); Sap(N12); Sap(N13); Sap(N14); Sap(N15); Sap(N16); Sap(N17); Sap(N18); Sap(N19); Sap(N20); Sap(N21); Sap(N22); Sap(N23); Sap(N24); Sap(N25); Sap(N26); Sap(N27); Sap(N28); Sap(N29); Sap(N30); Sap(N31); Sap(N32); Sap(N33); Sap(N34); Sap(N35); Sap(N36); Sap(N37); Sap(N38); Sap(N39); Sap(N40); Sap(N41); Sap(N42); Sap(N43); Sap(N44); Sap(N45); Sap(N46); Sap(N47); Sap(N48); Sap(N49); Sap(N50); Sap(N51); Sap(N52); Sap(N53); Sap(N54); Sap(N55); Sap(N56); Sap(N57); Sap(N58); Sap(N59); Sap(N60); Sap(N61); Dap(SN1); Dap(SN2); Dap(SN3); Dap(SN4); Dap(SN5); Dap(SN6); Dap(SN7); Dap(SN8); Dap(SN9); Dap(SN10); Dap(SN11); Dap(SN12); Dap(SN13); Dap(SN14); Dap(SN15); Dap(SN16); Dap(SN17); Dap(SN18); Dap(SN19); Dap(SN20); Dap(SN21); Dap(SN22); Dap(SN23); Dap(SN24); Dap(SN25); Dap(SN26); Dap(SN27); Dap(SN28); Dap(SN29); Dap(SN30); Dap(SN31); Dap(SN32); Dap(SN33); Dap(SN34); Dap(SN35); Dap(SN36); Dap(SN37); Dap(SN38); Dap(SN39); Dap(SN40); Dap(SN41); Dap(SN42); Dap(SN43); Dap(SN44); Dap(SN45); Dap(SN46); Dap(SN47); Dap(SN48); Dap(SN49); Dap(SN50); Dap(SN51); Dap(SN52); Dap(SN53); Dap(SN54); Dap(SN55); Dap(SN56); Dap(SN57); Dap(SN58); Dap(SN59); Dap(SN60); Dap(SN61); Dap(UN1); Dap(UN2); Dap(UN3); Dap(UN4); Dap(UN5); Dap(UN6); Dap(UN7); Dap(UN8); Dap(UN9); Dap(LTN10); Dap(UN11); Dap(UN12); Dap(UN13); Dap(UN14); Dap(UN15); Dap(UN16); Dap(UN17); Dap(UN18); Dap(UN19); Dap(UN20); Dap(UN21); Dap(UN22); Dap(UN23); Dap(UN24); Dap(UN25); Dap(UN26); Dap(UN27); Dap(UN28); Dap(UN29); Dap(UN30); Dap(UN31); Dap(UN32); Dap(UN33); Dap(UN34); Dap(UN35); Dap(UN36); Dap(UN37); Dap(UN38); Dap(UN39); Dap(UN40); Dap(UN41); Dap(UN42); Dap(UN43); Dap(UN44); Dap(UN45); Dap(UN46); Dap(UN47); Dap(UN48); Dap(UN49); Dap(UN50); Dap(UN51); Dap(UN52); Dap(UN53); Dap(UN54); Dap(UN55); Dap(UN56); Dap(UN57); Dap(UN58); Dap(UN59); Dap(UN60); Dap(UN61); Dap(S1); Dap(S2); Dap(S3); Dap(S4); Dap(S5); Dap(S6); Dap(S7); Dap(S8); Dap(S9); Dap(S10); Dap(S11); Dap(S12); Dap(S13); Dap(S14); Dap(S15); Dap(S16); Dap(S17); Dap(S18); Dap(A1); Dap(A2); Dap(A3); Dap(A4); Dap(A5); Dap(A6); Dap(A7); Dap(A8); Dap(A9); Dap(A10); Dap(A11); Dap(Al12); Dap(A13); Dap(A14); Dap(A15); Dap(A16); Dap(A17); Dap(A18); Dap(A19); Dap(A20); Dap(A21); Dap(A22); Dap(A23); Dap(A24); Dap(A25); Dap(A26); Dap(A27); Dap(A28); Dap(A29); Dap(A30); Dap(A31); Dap(A32); Dap(A33); Dap(A34); Dap(A35); Dap(A36); Dap(A37); Dap(A38); Dap(A39); Dap(A40); Dap(A41); Dap(A42); Dap(A43); Dap(A44); Dap(A45); Dap(A46); Dap(A47); Dap(A48); Dap(A49); Dap(A50); Dap(A51); Dap(A52); Dap(A53); Dap(A54); Dap(Suc1); Dap(Suc2); Dap(Suc3); Dap(Suc4); Dap(SucS); Dap(Suc6); Dap(Suc7); Dap(Suc8); Dap(Suc9); or Dap(Suc10);

or alternatively His; His(Me); His(Bn); hHis; Lat; Trp; Trp(5OH); Trp(5Cl); Trp(6Cl); Trp(5,6Cl$_2$); Trp(5Br); Trp(6Br); Trp(6CF$_3$); Trp(7Aza); hTrp; Tza; 2Pal; 3Pal; 4Pal; h2Pal; h3Pal; h4Pal; Ala(1Im); Ala(2Im); hAla(1Im); hAla(2Im); Ala(Pyrazinyl); Ala(1Pyrazolyl); Ala(3Pyrazolyl); Ala(2Pyrimidin); Ala(4Pyrimidin); Ala(5Pyrimidin); Ala(2Quin); Ala(3Quin); or Ala(4Quin);

or pharmaceutically acceptable salts thereof.

5. Compounds according to claim 4 wherein P$^{13}$ and P$^3$ are independently His; His(Me); His(Bn); hHis; Phe; Phe(2Cl); Phe(3Cl); Phe(4Cl); Phe(3,4Cl$_2$); Phe(2F); Phe(3F); Phe(4F); Phe(3,4F$_2$); Phe(3CN); Phe(4CN); Phe(2CF$_3$); Phe(3CF$_3$); Phe(4CF$_3$); Phe(3,4(CF$_3$)$_2$); Phe(4COOMe); hPhe; Thi; Tza; Trp; Trp(5OH); Trp(5Cl); Trp(6Cl);

Trp(5,6Cl₂); Trp(5Br); Trp(6Br); Trp(6CF₃); Trp(7Aza); hTrp; Tyr; Tyr(Me); Tyr(Ph); Tyr(Bn); Tyr(4OHPh); Tyr(4MeOCOBn); hTyr; Thr(Bn); Ser(Bn); 2Pal; 3Pal; 4Pal; Phg; Ala(2Furyl); Ala(3Furyl); Ala(2Quin); Ala(3Quin); Ala(4Quin); Ala(tBu); Gly(tBu); 1Nal; 2Nal; Nle(6OBn); Cha; hCha; Bip; Bbta; or OctG;

P² is Aib; Ac3c; Ac4c; Cyp; Chx; Chx(4oxo); Ac7c; Ac8c; ᴰAtc; ᴸAtc; ᴰᴸAtc; Deg; or 4,4-AC-ThioTHP;

P⁴ is Arg; hArg; Ala(Ppz); Thr; alloThr; Gln; Gln(Me); Gln(Me₂); Gln(iPr); Gln(cPr); Gln(iBu); Glu(Ala); Glu(ᴰAla); Glu(Arg); Glu(ᴰArg); Glu(Glu); Glu(Gly); Glu(His); Glu(Leu); Glu(ᴰLeu); Glu(2Nal); Glu(Sar); Glu(Trp); Glu(ᴰTrp); Cys; hCys; Ser; hSer; Ser(Me); hSer(Me); Thr; Met; Met(O₂); Lys; hLys; Lys(Ac); Lys(Me); Lys(Bz); Lys(Nic); Lys(4Oxa); Lys((5R)OH); Orn; Dap; Dap(MeO(CH₂)₂); Dap(CONH₂); Dap((MeO(CH₂)₂)₂); Dab(Sar); Dab; Dab(Ac); Dab(Ala); Dab(ᴰAla); Dab(Arg); Dab(ᴰArg); Dab(Dab); Dab(Glu); Dab(Gly); Dab(His); Dab(Leu); Dab(ᴰLeu); Dab(MEMCO); Dab(4Me₂NPhSO₂); Dab(MeO(CH₂)₂NHCO); Dab((MeO(CH₂)₂)(Me)NCO); Dab(MePpzCO); Dab(MeSO₂); Dab(morphCO); Dab(2Nal); Dab(Trp); Dab(ᴰTrp); Dab(Sar); or Dab(SN13);
or alternatively His; His(Me); hHis; 2Pal; 3Pal; 4Pal; h2Pal; h3Pal; h4Pal; Trp; Ala(1Im); Ala(2Im); hAla(1Im); hAla(2Im); or Ala(2Pyrimidin);

or pharmaceutically acceptable salts thereof.

6. Compounds according to claim 5 wherein

T¹ is ᴰPro; ᴰPip; or ᴰAze;

T² is Pro; ᴰPro; Oic; Pip; Tic; Tic(7OH); Thz; Thz(5,5Me₂); Pro((4S)F); Pro(5,5Me₂); Pro((4S)cHex); Pro((4R)Ph); Pro((4R)Bn); Pro((4R)4BrBn); Pro((4R)3CNBn); Hyp(Ph); Hyp(Bn); Hyp(4BrBn); Hyp(3CNBn); Hyp(4CNBn); Hyp(CONHPh); or (4S)-Hyp(Bn);

P¹ and P³ are independently
Phe; Phe(4Cl); Phe(4F); Phe(4CN); Phe(3CF₃); Phe(4CF₃); Phe(4COOMe); Trp; Trp(5OH); Trp(6Cl); Tyr; Tyr(Me) Tyr(Ph); Tyr(4OHPh); Tyr(4MeOCOBn); hTyr; Ala(2Furyl); Ala(2Quin); 2Nal; Nle(6OBn); ᴰᴸTrp(7Aza); Cha; Bip; Bbta; or OctG;

P² is Aib; Ac3c; Ac4c; Cyp; Chx; Chx(4oxo); Ac7c; Ac8c; ᴰᴸAtc; Deg; or 4,4-AC-ThioTHP;

P⁴ is Arg; hArg; Ala(Ppz); Thr; alloThr; Gln; Gln(iPr); Gln(cPr); Glu(Ala); Glu(ᴰAla); Glu(Arg); Glu(ᴰArg); Glu(Glu); Glu(Gly); Glu(His); Glu(Leu); Glu(ᴰLeu); Glu(2Nal); Glu(Sar); Glu(Trp); Glu(ᴰTrp); Cys; hCys; Ser; hSer; Ser(Me); hSer(Me); Thr; Met; Met(O₂); Lys; hLys; Lys(Ac); Lys(Me); Lys(Bz); Lys(Nic); Lys(4Oxa); Lys((5R)OH); Dap; Dap(MeO(CH₂)₂); Dap(CONH₂); Dap((MeO(CH₂)₂)₂); Dab; Dab(Ac); Dab(morphCO); Dab(MePzCO); Dab(MEMCO); Dab(MeO(CH₂)₂NHCO); Dab((MeO(CH₂)₂)(Me)NCO); Dab(MeSO₂); Dab(4Me₂NPhSO₂); Dab(Dab); or Dab(SN13);

or alternatively His; hHis; 2Pal; 3Pal; or 4Pal;

or pharmaceutically acceptable salts thereof.

7. Compounds according to claim 2 which are selected from cyclo(-Trp-Aib-Trp-Arg-ᴰPro-Tic-); cyclo(-Trp-Aib-Trp-Dab-ᴰPro-Tic-); cyclo(-Trp-Cyp-Trp-Arg-ᴰPro-Tic(7OH)-); cyclo(-Trp-Cyp-Trp-Dab-ᴰPro-Pro((4S)F)-); cyclo(-Trp-Cyp-Trp-Arg-ᴰPro-Thz-); cyclo(-Trp-Cyp-Trp-Dab-ᴰPro-Thz-); cyclo(-Trp(5OH)-Cyp-Trp-Gln-ᴰPro-Thz-); cyclo(-Trp(5OH)-Cyp-Trp-Arg-ᴰPro-Tic-); cyclo(-2Nal-Cyp-Trp-Gln-ᴰPro-Tic-); cyclo(-2Nal-Cyp-Trp-Dab-ᴰPro-Pip-); cyclo(-Trp(5OH)-Chx-Trp(5OH)-Arg-ᴰPro-Oic-); cyclo(-Trp(5OH)-Cyp-Trp(5OH)-Dap-ᴰPro-Oic-); cyclo(-Trp-Cyp-Trp-Dab-ᴰPip-Oic-); cyclo(-Trp-Cyp-2Nal-Dab-ᴰPro-Oic-); cyclo(-Trp-Cyp-Cyp-2Nal-Gln-ᴰPro-Oic-); cyclo(-OctG-Cyp-Trp-Dab-ᴰPro-Oic-); cyclo(-Trp-Cyp-Trp-Gln-ᴰPro-Oic-); cyclo(-Trp-Chx-Trp-Dab-ᴰPro-Oic-); cyclo(-Trp-Ac3c-Trp-Dab-ᴰPro-Oic-); cyclo(-Trp-Ac4c-Trp-Dab-ᴰPro-Oic-); cyclo(-Trp-4,4-AC-ThioTHP-Trp-Dab-ᴰPro-Oic-); cyclo(-Trp-Cyp-Phe(4F)-Dab-ᴰPro-Oic-); cyclo(-Trp-Cyp-Tyr(Me)-Dab-ᴰPro-Oic-); cyclo(-Trp-Cyp-Ala(2Quin)-Dab-ᴰPro-Oic-); cyclo(-Trp-Cyp-Trp-Arg-ᴰAze-Tic-); cyclo(-Trp-Cyp-Trp-Dab-ᴰAze-Tic-); cyclo(-Cha-Cyp-Trp-Dab-ᴰPro-Oic-); cyclo(-Trp-Cyp-Trp-Dab-ᴰPro-Oic-); cyclo(-Trp(5OH)-Cyp-Trp-Arg-ᴰPro-Thz(5,5Me₂)-); cyclo(-Trp-Atc-Trp-Dab-ᴰPro-Oic-); cyclo(-Trp-Cyp-Ala(2Furyl)-Dab-ᴰPro-Oic-); cyclo(-Trp-Cyp-Phe(4F)-Ser-ᴰPro-Oic-); cyclo(-Trp-Cyp-Phe(4Cl)-Ser-ᴰPro-Oic-); cyclo(-Trp-Cyp-Phe(4CF3)-Dab-ᴰPro-Oic-); cyclo(-Trp-Cyp-DLTrp(7Aza)-Dab-ᴰPro-Oic-); cyclo(-Trp-Cyp-Tyr(Ph)-Dab-ᴰPro-Oic-); cyclo(-Phe(4CF₃)-Cyp-Trp-Dab-ᴰPip-Pro((4R)Ph)-); cyclo(-Trp-Cyp-Trp-Dab-ᴰPro-Pro((4R)Bn)-); cyclo(-Trp-Cyp-Trp-Dab-ᴰPro-Pro((4R)4BrBn)-); cyclo(-Trp-Cyp-Trp-Dab-ᴰPro-Pro((4R)3CNBn)-); cyclo(-Trp-Cyp-Trp-Dab-ᴰPro-Pro((4S)cHex)-); cyclo(-Trp-Cyp-Trp-Dab-ᴰPro-Pro(5,5Me₂)-); cyclo(-Trp-Cyp-Phe(4Cl)-Dab-ᴰPro-Hyp(Bn)-); cyclo(-Phe(4CN)-Cyp-Phe(4F)-Ser-ᴰPro-Hyp(Bn)-); cyclo(-Trp-Cyp-Trp-Dab-ᴰPro-Hyp(Bn)-); cyclo(-Trp-Cyp-Trp-Ser-ᴰPro-Hyp(Bn)-); cyclo(-Phe(4CN)-Cyp-Trp-Gln-ᴰPro-Hyp(Bn)-); cyclo(-Trp(6Cl)-Cyp-Trp-Dab-ᴰPro-Hyp(Bn)-); cyclo(-Phe(4CN)-Cyp-Trp-Dab-ᴰPro-Hyp(Bn)-); cyclo(-Phe(4CN)-Cyp-Trp-Ser-ᴰPip-Hyp(Bn)-); cyclo(-Trp-Cyp-Trp-Dab-ᴰPro-(4S)-Hyp(Bn)-); cyclo(-Trp-Cyp-Trp-Dab-ᴰPro-Hyp(Ph)-); cyclo(-Trp-Cyp-Trp-Dab-ᴰPro-Hyp(4CNBn)-); cyclo(-Phe(4CF₃)-Cyp-Trp-Dab-ᴰPro-Hyp(4BrBn)-); cyclo(-Phe(4CN)-Cyp-Trp-Ser-ᴰPro-Hyp(4BrBn)-); cyclo(-Trp-Cyp-Trp-Dab-ᴰPro-Hyp(4BrBn)-); cyclo(-Trp-Cyp-Trp-Dab-ᴰPro-Hyp(CONHPh)-); cyclo(-Trp-Cyp-Trp-alloThr-ᴰPro-Oic-); cyclo(-Trp-Cyp-Trp-hArg-ᴰPro-Oic-); cyclo(-Trp-Cyp-Trp-hCys-ᴰPro-Oic-); cyclo(-Trp-Cyp-Trp-Gln(iPr)-ᴰPro-Oic-); cyclo(-Trp-Cyp-Trp-hSer(Me)-ᴰPro-Oic-); cyclo(-Trp-Cyp-Trp-Lys(Ac)-ᴰPro-Oic-); cyclo(-Trp-Cyp-Trp-Lys(Bz)-ᴰPro-Oic-); cyclo(-Trp-Cyp-Trp-Lys(Me)-ᴰPro-Oic-); cyclo(-Trp-Cyp-Trp-Lys((5R)OH)-ᴰPro-Oic-); cyclo(-Trp-Cyp-Trp-Lys(Nic)-ᴰPro-Oic-); cyclo(-Trp-Cyp-Trp-Met(O₂)-ᴰPro-Oic-); cyclo(-Trp-Cyp-Trp-Ala(Ppz)-ᴰPro-Oic-); cyclo(-Trp-Cyp-Trp-Dap(CONH₂)-ᴰPro-Oic-); cyclo(-Trp-Cyp-Trp-Dab(Dab)-ᴰPro-Oic-); cyclo(-Trp-Cyp-Trp-Dab(MEMCO)-ᴰPro-Oic-); cyclo(-Trp-Cyp-Trp-Dab(MeO(CH₂)₂NHCO)-ᴰPro-Oic-; cyclo(-Trp-Cyp-Trp-Dap(MeO(CH₂)₂)-ᴰPro-Oic-); cyclo(-Trp-Cyp-Trp-Dap((MeO(CH₂)₂)₂)-ᴰPro-Oic-); cyclo(-Ph(4COOMe)-Cyp-Trp-Dab-ᴰPro-Oic-); cyclo(-Trp-Cyp-Trp-Dab-ᴰPro-Hyp(3 CNBn)-); cyclo(-Phe(4CN)-Cyp-Trp-Dab-ᴰPro-Oic-); cyclo(-Trp-Cyp-Trp-Ser-ᴰPro-Oic-); cyclo(-Trp-Cyp-Trp-Ser-ᴰPip-Oic-); cyclo(-Trp(6Cl)-Cyp-Trp-Ser-ᴰPro-Oic-); cyclo(-Phe(4CN)-Cyp-Trp-Ser-ᴰPro-Oic-); cyclo(-Trp-Cyp-Trp-Lys(4Oxa)-ᴰPro-Oic-); cyclo(-Trp-Cyp-Trp-Ser(Me)-ᴰPro-Oic-); cyclo(-Trp-Cyp-Trp-Thr-ᴰPro-Oic-); cyclo(-Bip-Cyp-Trp-Dab-ᴰPro-Oic-); cyclo(-hTyr-Cyp-Trp-Dab-ᴰPro-Oic-); cyclo(-Bbta-Cyp-Trp-Dab-ᴰPro-Oic-); cyclo(-Nle(6OBn)-Cyp-Trp-Dab-DPro-Oic-); cyclo(-Tyr(4OHPh)-Cyp-Trp-Dab-ᴰPro-Oic-); cyclo(-Tyr(Ph)-Cyp-Trp-Dab-ᴰPro-Oic-); cyclo(-Tyr(4MeOCOBn)-Cyp-Trp-Dab-ᴰPro-Oic-); cyclo(-Trp-Deg-Trp-Dab-ᴰPro-Oic-); cyclo(-Trp-Ac7c-Trp-Dab-ᴰPro-Oic-); cyclo(-Trp-Chx(4oxo)-Trp-Dab-ᴰPro-Oic-); cyclo(-Trp-Ac8c-Trp-Dab-ᴰPro-Oic-); cyclo (-Trp-Cyp-Trp-DabaMeO(CH$_2$)$_2$)(Me)NCO)-$^D$Pro-Oic-); cyclo(-Trp-Cyp-Trp-Dab(morphCO)-$^D$Pro-Oic-); cyclo (-Trp-Cyp-Trp-Dab(MePpzCO)-$^D$Pro-Oic-); cyclo(-Trp-Cyp-Trp-Dab(MeSO$_2$)-$^D$Pro-Oic-) cyclo(-Trp-Cyp-Trp-Dab (4Me$_2$NPhSO$_2$)-$^D$Pro-Oic-); cyclo(-Trp-Cyp-Trp-Dab(Ac)-$^D$Pro-Oic-); cyclo(-Trp-Cyp-Trp-Dab-$^D$Pro-Hyp-); cyclo (-Trp-Cyp-Trp-Dap-$^D$Pro-Oic-); cyclo(-Trp-Cyp-Trp-Dab (SN13)-$^D$Pro-Oic-);

or pharmaceutically acceptable salts thereof.

8. Compounds according to claim 7 which are selected from cyclo(-Cha-Cyp-Trp-Dab-$^D$Pro-Oic-); cyclo(-Trp-Cyp-Trp-Dab-$^D$Pro-Oic-); cyclo(-Phe(4CF$_3$)-Cyp-Trp-Dab-$^D$Pip-Pro((4R)Ph)-); cyclo(-Trp-Cyp-Trp-Dab-$^D$Pro-Pro(5, 5Me$_2$)-); cyclo(-Phe(4CN)-Cyp-Trp-Dab-$^D$Pro-Hyp(Bn)-); cyclo(-Trp-Cyp-Trp-Met(O$_2$)-$^D$Pro-Oic-); cyclo(-Trp-Cyp-Trp-Dap(CONH$_2$)-$^D$Pro-Oic-); cyclo(-Phe(4CN)-Cyp-Trp-Dab-$^D$Pro-Oic-); cyclo(-Trp-Cyp-Trp-Lys(4Oxa)-$^D$Pro-Oic-); cyclo(-Trp-Cyp-Trp-Dab(MePpzCO)-$^D$Pro-Oic-);

or pharmaceutically acceptable salts thereof.

9. Compounds according to claim 1 which are selected from cyclo(-Trp-Cyp-Trp-Dab(A55)-$^D$Pro-Oic-); cyclo(-Phe (4CF$_3$)-Cyp-Trp-Dab-$^D$Pro-Oic-); cyclo(-Phe(4CF$_3$)-Cyp-Trp-Dab(A56)-$^D$Pro-Oic-); cyclo(-Phe(3CF$_3$)-Cyp-Trp-Dab-$^D$Pro-Oic-); cyclo(-Phe(4CF$_3$)-Cyp-Trp-3Pal-$^D$Pic-Oic-);

or pharmaceutically acceptable salts thereof.

10. Diastereomers, epimers and enantiomers of the compounds of formula (I) as defined in claim 1.

11. Compounds according to claim 1 for use as therapeutically active substances.

12. Compounds according to claim 1 having antagonizing activity against the CCR10 receptor.

13. Compounds according to claim 1 selectively interfering with the natural activity of the CCR10 receptor and its natural ligands CCL27 and/or CCL28.

14. A pharmaceutical composition containing a compound or a mixture of compounds according to claim 1 and a pharmaceutically inert carrier.

15. Compositions according to claim 14 in a form suitable for oral, topical, transdermal, injection, buccal, transmucosal, rectal, pulmonary or inhalation administration, especially in the form of tablets, dragees, capsules, solutions, liquids, gels, plaster, creams, ointments, syrup, slurries, suspensions, spray, nebuliser or suppositories.

16. A method of treating a disease or disorder selected from the group consisting of dermatological disorders, metabolic diseases, inflammatory diseases, neurological diseases, respiratory diseases, gastro-intestinal tract disorders, ophthalmic diseases, haematological diseases and cancer, comprising the step of:

administering a therapeutically effective amount of the compounds according to claim 1 to a patient in need thereof.

17. A process for the preparation of compounds according to claim 1 which comprises
(a) coupling an appropriately functionalized solid support with an appropriately N-protected derivative of that amino acid which in the desired end-product is in position $T^1$ or $T^2$ or $P^1$ to $P^4$ as defined above; any functional group which may be present in said N-protected amino acid derivative being likewise appropriately protected;
(b) removing the N-protecting group from the product obtained in step (a);
(c) coupling the product thus obtained with an appropriately N-protected derivative of that amino acid which in the desired end-product is in the position of the next element (T or P), following counterclockwise or clockwise the sequence according to general formula (I) in COOH to NH$_2$ orientation; any functional group which may be present in said N-protected amino acid derivative being likewise appropriately protected;
(d) removing the N-protecting group from the product thus obtained;
(e) repeating steps (c) and (d) until all amino acid residues have been introduced;
(f) if desired, selectively deprotecting one or several protected functional group(s) present in the molecule and chemically transforming the reactive group(s) thus liberated;
(g) detaching the product thus obtained from the solid support;
(h) cyclizing the product cleaved from the solid support;
(i) removing any protecting groups present on functional groups of any members of the chain of amino acid residues and, if desired, any protecting group(s) which may in addition be present in the molecule; and
(j) if desired, implementing additional chemical transformations of one or more reactive group(s) present in the molecule;
(k) if desired, converting the product thus obtained into a pharmaceutically acceptable salt or converting a pharmaceutically acceptable, or unacceptable, salt thus obtained into the corresponding free compound of formula (I) or into a different, pharmaceutically acceptable salt.

18. The process of claim 17, wherein the compounds of formula (I) comprise one or more diastereomers, epimers or enantiomers.

19. The method of claim 16, wherein the disease or disorder is psoriasis, atypical dermatitis, contact sensitivity, allergic dermatitis, Stevens-Johnson syndrome, bullous cutaneous diseases, systemic lupus erythematosis, systemic and multiple sclerosis, allergic asthma, arthritis, graft versus host disease, certain melanoma and cutaneous lymphoma, or inflammatory processes of the gastro-intestinal tract and the eye.

* * * * *